(12) United States Patent
Sutton et al.

(10) Patent No.: US 12,076,383 B2
(45) Date of Patent: Sep. 3, 2024

(54) COMPOSITIONS AND METHODS FOR INDUCING HUMORAL AND CELLULAR IMMUNITIES AGAINST TUMORS AND CANCER

(71) Applicant: Cancer Advances Inc., Durham, NC (US)

(72) Inventors: Lynda Sutton, Durham, NC (US); Jill P. Smith, Camp Hill, PA (US); Nicholas Osborne, Durham, NC (US); Brian E. Huber, Durham, NC (US); Allen Cato, Durham, NC (US)

(73) Assignee: Cancer Advances Inc., Durham, NC (US)

( * ) Notice: Subject to any disclaimer, the term of this patent is extended or adjusted under 35 U.S.C. 154(b) by 0 days.

(21) Appl. No.: 18/056,843

(22) Filed: Nov. 18, 2022

(65) Prior Publication Data
US 2023/0086898 A1 Mar. 23, 2023

Related U.S. Application Data

(62) Division of application No. 16/622,841, filed as application No. PCT/US2018/037737 on Jun. 15, 2018, now Pat. No. 11,583,576.

(60) Provisional application No. 62/520,267, filed on Jun. 15, 2017.

(51) Int. Cl.
| A61K 39/00 | (2006.01) |
| A61K 39/39 | (2006.01) |
| A61K 39/395 | (2006.01) |
| A61P 35/00 | (2006.01) |
| C07K 16/28 | (2006.01) |

(52) U.S. Cl.
CPC ...... *A61K 39/001102* (2018.08); *A61K 39/39* (2013.01); *A61K 39/39541* (2013.01); *A61P 35/00* (2018.01); *C07K 16/2869* (2013.01); *A61K 2039/505* (2013.01); *A61K 2039/575* (2013.01); *A61K 2039/6037* (2013.01); *A61K 2039/627* (2013.01); *A61K 2039/852* (2018.08)

(58) Field of Classification Search
CPC ......... C07K 14/375; A61P 31/20; A61P 35/00
See application file for complete search history.

(56) References Cited

U.S. PATENT DOCUMENTS

| 3,391,141 A | 7/1968 | Gottstein et al. |
| 4,069,313 A | 1/1978 | Woodhour et al. |
| 4,196,265 A | 4/1980 | Koprowski et al. |
| 4,201,770 A | 5/1980 | Stevens |
| 4,384,995 A | 5/1983 | Stevens |
| 4,526,716 A | 7/1985 | Stevens |
| 4,565,805 A | 1/1986 | Smirnov |
| 4,687,759 A | 8/1987 | Martinez et al. |
| 4,691,006 A | 9/1987 | Stevens |
| 4,713,366 A | 12/1987 | Stevens |
| 4,762,913 A | 8/1988 | Stevens |
| 4,794,103 A | 12/1988 | Bertolini |
| 4,803,170 A | 2/1989 | Stanton et al. |
| 4,816,567 A | 3/1989 | Cabilly et al. |
| 4,840,939 A | 6/1989 | Leveen et al. |
| 4,894,443 A | 1/1990 | Greenfield et al. |
| 4,923,819 A | 5/1990 | Fernandez et al. |
| 4,925,922 A | 5/1990 | Byers et al. |
| 4,971,792 A | 11/1990 | Steplewski et al. |
| 4,978,683 A | 12/1990 | Rovati et al. |
| 4,997,950 A | 3/1991 | Murphy et al. |
| 5,006,334 A | 4/1991 | Stevens |
| 5,023,077 A | 6/1991 | Gevas et al. |
| 5,035,988 A | 7/1991 | Nakamura et al. |
| 5,055,404 A | 10/1991 | Ueda et al. |
| 5,110,911 A | 5/1992 | Samuel et al. |
| 5,120,829 A | 6/1992 | Pierschbacher et al. |
| 5,162,504 A | 11/1992 | Horoszewicz |
| 5,164,299 A | 11/1992 | Lambert |
| 5,256,542 A | 10/1993 | Chang |
| 5,319,073 A | 6/1994 | Wank |

(Continued)

FOREIGN PATENT DOCUMENTS

| CA | 2359180 | 8/2000 |
| CN | 101050236 A | 10/2007 |

(Continued)

OTHER PUBLICATIONS

Meirmont et al. Chemistry. 2008; 14(16): 4939-4947.*
National Institute of Cancer—understanding and related topics, accessed Aug. 18, 2019 at URL: https://www.cancer.gov/about-cancer/ understanding/what-is-cancer.*
"Clinical Study Report: G17DT," Aphton Corporation, 107 pages (Sep. 19, 2003).
"Clinical Trial Initiated with Chemorefractory Patients," Cancer Weekly, The Gale Group, (Jan. 9, 2001).

(Continued)

*Primary Examiner* — Jeanette M Lieb
(74) *Attorney, Agent, or Firm* — Jenkins, Taylor & Hunt, P.A.

(57) ABSTRACT

Provided are methods for sensitizing gastrin-associated tumors and/or cancers in subjects to inducers of humoral and cellular immune responses. In some embodiments, the methods relate to administering compositions that have anti-gastrin antibodies, gastrin peptides, and/or nucleic acids that inhibit expression of gastrin gene products to subjects. Also provided are methods for preventing, reducing, and/or eliminating the formation of fibroses associated with tumors and/or cancers, and methods for treating gastrin-associated tumors and/or cancers that include administering to subjects in need thereof a first agent that provides and/or induces an anti-gastrin humoral or cellular immune response in the subject and a second agent that includes one or more stimulators of cellular immune responses against the tumors and/or cancers.

9 Claims, 11 Drawing Sheets

Specification includes a Sequence Listing.

(56) References Cited

U.S. PATENT DOCUMENTS

| | | | |
|---|---|---|---|
| 5,468,494 A | 11/1995 | Gevas et al. |
| 5,484,596 A | 1/1996 | Hanna, Jr. et al. |
| 5,580,563 A | 12/1996 | Tam et al. |
| 5,585,474 A | 12/1996 | Iwaki et al. |
| 5,607,676 A | 3/1997 | Gevas et al. |
| 5,639,613 A | 6/1997 | Shay et al. |
| 5,643,735 A | 7/1997 | Yokoi et al. |
| 5,665,864 A | 9/1997 | Quaranta et al. |
| 5,668,117 A | 9/1997 | Shapiro |
| 5,683,695 A | 11/1997 | Shen et al. |
| 5,688,504 A | 11/1997 | Morgan, Jr. |
| 5,688,506 A | 11/1997 | Grimes et al. |
| 5,703,213 A | 12/1997 | Wands et al. |
| 5,712,369 A | 1/1998 | Old et al. |
| 5,723,718 A | 3/1998 | Berens |
| 5,731,159 A | 3/1998 | Waldman |
| 5,733,790 A | 3/1998 | Potter et al. |
| 5,736,146 A | 4/1998 | Cohen et al. |
| 5,750,119 A | 5/1998 | Srivastava |
| 5,759,551 A | 6/1998 | Ladd et al. |
| 5,759,791 A | 6/1998 | Kuhajda et al. |
| 5,767,242 A | 6/1998 | Zimmerman et al. |
| 5,770,576 A | 6/1998 | Morozov et al. |
| 5,786,213 A | 7/1998 | Singh et al. |
| 5,788,964 A | 8/1998 | Baral et al. |
| 5,827,691 A | 10/1998 | Iwaki et al. |
| 5,866,617 A | 2/1999 | Hausheer et al. |
| 5,869,045 A | 2/1999 | Hellstrom et al. |
| 5,869,058 A | 2/1999 | Cohen et al. |
| 5,879,898 A | 3/1999 | Tarin et al. |
| 5,932,412 A | 8/1999 | Dillner et al. |
| 5,955,504 A | 9/1999 | Wechter et al. |
| 5,981,167 A | 11/1999 | Taremi et al. |
| 6,169,173 B1 | 1/2001 | Wank |
| 6,180,370 B1 | 1/2001 | Queen et al. |
| 6,187,536 B1 | 2/2001 | Weinberg et al. |
| 6,191,290 B1 | 2/2001 | Safavy |
| 6,251,581 B1 | 6/2001 | Ullman et al. |
| 6,303,123 B1 | 10/2001 | Grimes et al. |
| 6,320,022 B1 | 11/2001 | Cutitta et al. |
| 6,359,114 B1 | 3/2002 | Grimes et al. |
| 6,391,299 B1 | 5/2002 | Blackburn et al. |
| 6,444,207 B1 | 9/2002 | Schoemaker et al. |
| 6,472,506 B1 | 10/2002 | Moreau et al. |
| 6,548,066 B1 | 4/2003 | Michaeli et al. |
| 6,565,813 B1 | 5/2003 | Garyantes |
| 6,613,530 B1 | 9/2003 | Wienhues et al. |
| 6,627,196 B1 | 9/2003 | Baughman et al. |
| 6,639,055 B1 | 10/2003 | Carter et al. |
| 6,689,869 B2 | 2/2004 | Waldmann et al. |
| 6,696,262 B2 | 2/2004 | Harkonen |
| 6,699,974 B2 | 3/2004 | Ono et al. |
| 6,780,969 B2 | 8/2004 | Wang |
| 6,815,414 B2 | 11/2004 | Chowers et al. |
| 6,835,543 B2 | 12/2004 | Saitoh et al. |
| 6,872,543 B1 | 3/2005 | Sipponen et al. |
| 7,074,761 B1 | 7/2006 | Hinuma et al. |
| 7,078,493 B1 | 7/2006 | Greene et al. |
| 7,192,582 B2 | 3/2007 | Hudson et al. |
| RE39,586 E | 4/2007 | Dagan |
| 7,235,376 B2 | 6/2007 | Grimes et al. |
| 7,291,721 B2 | 11/2007 | Giles-Komar et al. |
| 7,300,918 B2 | 11/2007 | Rath |
| 7,438,907 B2 | 10/2008 | Schuurman et al. |
| 7,662,926 B2 | 2/2010 | Chan et al. |
| 7,854,932 B2 | 12/2010 | Singh |
| 8,013,115 B1 | 9/2011 | Garric et al. |
| 8,158,128 B2 | 4/2012 | Grimes |
| 8,343,930 B2 | 1/2013 | Gevas et al. |
| 8,388,966 B2 | 3/2013 | Gevas et al. |
| 11,583,576 B2 | 2/2023 | Sutton et al. |
| 2002/0058040 A1 | 5/2002 | Grimes et al. |
| 2003/0021786 A1 | 1/2003 | Gevas et al. |
| 2003/0049698 A1 | 3/2003 | Wang |
| 2003/0068326 A1 | 4/2003 | Gevas et al. |
| 2003/0138860 A1 | 7/2003 | Robertson et al. |
| 2003/0232399 A1 | 12/2003 | Robertson et al. |
| 2004/0001842 A1 | 1/2004 | Michaeli et al. |
| 2004/0266682 A1 | 12/2004 | Cruz |
| 2005/0025770 A1 | 2/2005 | Gevas et al. |
| 2005/0169979 A1 | 8/2005 | Michaeli et al. |
| 2005/0187152 A1 | 8/2005 | Gevas et al. |
| 2006/0020119 A1 | 1/2006 | Grimes et al. |
| 2006/0110383 A1 | 5/2006 | Honjo et al. |
| 2007/0031511 A1 | 2/2007 | Baldwin et al. |
| 2007/0065454 A1 | 3/2007 | Michaeli et al. |
| 2007/0066809 A1 | 3/2007 | Grimes |
| 2007/0082043 A1 | 4/2007 | Michaeli et al. |
| 2016/0129096 A1 | 5/2016 | Mudde |
| 2016/0228561 A1 | 8/2016 | Xia et al. |
| 2016/0271239 A1 | 9/2016 | Foy et al. |
| 2020/0206332 A1 | 7/2020 | Sutton et al. |
| 2021/0275649 A1 | 9/2021 | Sutton et al. |

FOREIGN PATENT DOCUMENTS

| | | |
|---|---|---|
| EP | 1 579 863 | 9/2005 |
| EP | 3624841 A4 | 3/2020 |
| JP | 06107564 A | 4/1994 |
| WO | WO 1994/000590 | 1/1994 |
| WO | WO 1994/007530 | 4/1994 |
| WO | WO 1995/019568 | 7/1995 |
| WO | WO 1995/021380 | 8/1995 |
| WO | WO 1997/028821 | 8/1997 |
| WO | WO 1999/059628 | 11/1999 |
| WO | WO 2001/034192 | 5/2001 |
| WO | WO 2001/077685 | 10/2001 |
| WO | WO 02/076499 A2 | 10/2002 |
| WO | WO 2004/023148 | 3/2004 |
| WO | WO 2006/008649 | 1/2006 |
| WO | WO 2007/062531 | 6/2007 |
| WO | WO 2013/088141 A1 | 6/2013 |
| WO | WO 2016/196935 A1 | 12/2016 |
| WO | WO 2018/232230 A1 | 12/2018 |
| WO | WO 2022/155320 A1 | 7/2022 |

OTHER PUBLICATIONS

"Clinical trials update," Scrip, Informa UK Ltd., No. 2547 p. 25 (Jun. 9, 2000).

"Development and Activity of 5-FU," CancerQuest, http://www.cancerquest.org/index.cfm?page=443 (accessed on Aug. 13, 2004) 1 pg.

"Gastrin 17 immunogen Aphton begins combination study," R&D Focus Drug News, IMS World Publications (2000).

"Other News to Note," Bioworld Today, American Health Consultants Inc., vol. 11, No. 82 pp. 1-8 (Apr. 27, 2000).

"ADAP drugs: leucovorin," Access Project, http://www.aegis.com/factshts/network/access/drugs/leuc.html (1996) (accessed on Aug. 13, 2004), 1 page.

"Prilosec OTC Review: Two Advisory Committee Members Weigh in Without Voting," The Pink Sheet. pp. 22-23 (2002).

Abbruzzese et al., "Phase I Trial of Recombinant Human—Interferon and Recombinant Human Tumor Necrosis Factor in Patients with Advanced Gastrointestinal Cancer," Cancer Research. Vol. 49 pp. 4057-4061 (1989).

Abdalla et al., "Gastrin-Induced Cyclooxygenase-2 Expression in Barrett's Carcinogenesis," Clinical Cancer Research. Vol. 10 pp. 4784-4792 (2004).

Abrahm et al., "Development and Evaluation of a High Affinity Species and Region Specific Monoclonal Antibody to Human Gastrin," Gastroenterology. vol. 86, No. 5, Part 2 p. 1012 (1984).

Ajani et al., "Phase I and II Studies of the Combination of Recombinant Human Interferon-( and 5-Fluorouracil in Patients with Advanced Colorectal Carcinoma," Journal of Biological Response Modifiers. vol. 8, No. 2 pp. 140-146 (1989).

Ajani et al., "An Open-Label, Multinational, Multicenter Study of G17DT Vaccination Combined with Cisplatin and 5-Fluorouracil in Patients with Untreated, Advanced Gastric or Gastroesophageal Cancer: The GC4 Study," Cancer. vol. 106, No. 9 pp. 1908-1916 (2006).

(56) References Cited

OTHER PUBLICATIONS

Akai, "Co-Existence and Co-Release of Gastrin 34 N-Terminal Fragment With Gastrin 17 in Rat Stomach," Folla endocrinol. vol. 64 pp. 1065-1080 (1988) [Abstract].
Aphton Biopharma BIO2005 Presentation, Jun. 19-22, Philadelphia, PA (2005), 26 pages.
Ardill et al., "Autoantibodies to gastrin in patients with pernicious anaemia—a novel antibody," Q. J. Med. vol. 91 pp. 739-742 (1998).
Adis R&D Profile, "Gastrin 17 vaccine—Aphton: Anti-gastrin 17 immunogen, G17DT," Biodrugs. vol. 17, No. 3 pp. 223-225 (2003).
Asao et al., "Eradication of Hepatic Metastases of Carcinome H-59 by Combination Chemimmunotherapy with Liposomal Muramyl Tripeptide, 5-Fluorouracil, and Leucovorin," Cancer Research. vol. 52 pp. 6254-6257 (1992).
Ausubel, ed., "Current Protocols in Molecular Biology," John Wiley & Sons, New York, pp. 11.15.1-11.15.9. (2002).
Azuma et al. "Effects of Bombesin on the Release of Glycine-Extended Progastrin (Gastrin G) in Rat Antral Tissue Culture" Gastroenterology 1987;93:322-9.
Azuma et al., "Immunocytochemical Evidence for Differential Distribution of Gastrin Forms Using Region-Specific Antibodies," Gastroenterologia Japonica. vol. 21, No. 4 pp. 319-324 (1986).
Baba et al., "Glycine-Extended Gastrin Induces Matrix Metalloproteinase-1-and-3-Mediated Invasion of Human Colon Cancer Cells Through Type 1 Collagen Gel and Matrigel," International Journal of Cancer. vol. 111, No. 1 pp. 23-31 (2004).
Bailey, "Radioimmunoassay of Peptides and Proteins," Methods in Molecular Biology. vol. 32 pp. 449-459 (1994).
Baldwin et al., "Binding of the progastrin fragments to the 78 κDa gastrin-binding protein," FEBS Lett. vol. 359 pp. 97-100 (1995).
Baldwin, G.S., and Zhang, Q., "Measurement of Gastrin and Transforming Growth Factor αMessenger RNA Levels in Colonic Carcinoma Cell Lines by Quantitative Polymerase Chain Reaction," Cancer Research. vol. 52 pp. 2261-2267(1992).
Baldwin, G.S. and Shulkes, A., "Gastrin, gastrin receptors and colorectal carcinoma," Gut. vol. 42 pp. 581-584 (1998).
Ballantyne, G.H., and Quin, J., "Surgical Treatment of Liver Metastasis in Patients with Colorectal Cancer," Cancer. vol. 71, No. 12 pp. 4252-4266 (1993).
Bardram, "Progastrin in Serum from Zollinger-Ellison Patients: An Indicator of Malignancy?" Gastroenterology. vol. 98, No. 6 pp. 1420-1426 (1990).
Beacham et al., "Human Gastrin: Isolation, Structure and Synthesis: Synthesis of Human Gastrin I," Nature. Vol. 209, No. 5023 pp. 585-586 (1966).
Beauchamp et al., "Proglumide, A Gastrin Receptor Antagonist, Inhibits Growth of Colon Cancer and Enhances Survival in Mice," Ann. Surg. vol. 202, No. 3 pp. 303-308 (1985).
Behr et al., "Cholecystokinin-B/Gastrin Receptor Binding Peptides: Preclinical Development and Evaluation of Their Diagnostic and Therapeutic Potential," Clinical Cancer Research. vol. 5 pp. 3124s-3138s (1999).
Beinborn et al., "A single amino acid of the cholecystokinin-B/gastrin receptor determines specificity for non-peptide antagonists," Nature. vol. 362 pp. 348-350 (1993).
Belani, C., "Paclitaxel and Docetaxel Combinations in Non-Small Cell Lung Cancer," Chest. vol. 117 pp. 144S-151S (2000).
Bentley et al., "Human Gastrin: Isolation, Structure and Synthesis," Nature. Vol. 209, No. 5023 pp. 583-585 (1966).
Berg et al. in "Biochemistry," New York: W.H. Freeman and Co., 4.3.1-4.3.3 and Figure 4.35 (2002).
Berna et al., "Role of CCK/gastrin receptors in gastrointestinal/metabolic diseases and results of human studies using gastrin/CCK receptor agonists/antagonists in these diseases." Curr. Top. Med. Chem., vol. 7, pp. 1211-1231 (2007).
Biagini et al., "The Human Gastrin/Cholecystokinin Receptors: Type B and Type C Expression in Colonic Tumours and Cell Lines," Life Sciences. vol. 61, No. 10 pp. 1009-1018 (1997).

Bian et al., "Pancreatic Cancer and Immune Checkpoint Inhibitors—still a long way to go." Transl. Gastroenterol. Hepatol., vol. 6 (5 pages) (2021).
Blackmore et al. "Autocrine Growth Stimulation of Human Renal Wilms' Tumour G401 Cells by a Gastrin-Like Peptide," International Journal of Cancer. Vol. 57 pp. 385-391 (1994).
Bock et al., "Benzodiazepine Gastrin and Brain Cholecystokinin Receptor Ligands: L-365,260," Journal of Medicinal Chemistry. vol. 32, No. 1 pp. 13-16 (1989).
Bodey, "The significance of immunohistochemistry in the diagnosis and therapy of neoplasms," Expert Opin. Biol. Ther. vol. 2, No. 4 pp. 371-393 (2002).
Boland, "Editorial: Gastrin and Colorectal Neoplasia-Chicken or Egg, or Both?" J. Clin. Gastroenterology. vol. 13, No. 5 pp. 497-499 (1991).
Bold et al., "Gastrin Stimulates Growth of Human Colon Cancer Cells Via A Receptor Other Than CCK-A or CCK-B," Biochemical and Biophysical Research Communications. vol. 202, No. 3 pp. 1222-1226 (1994).
Boon, "Toward a Genetic Analysis of Tumor Rejection Antigens," Advances in Cancer Research. vol. 58 pp. 177-210 (1992).
Bowie et al., "Deciphering the Message in Protein Sequences: Tolerance to Amino Acid Substitutions," Science. vol. 247 pp. 1306-1310 (1990).
Brahmer et al., "Safety and activity of anti-PD-L1 antibody in patients with advanced cancer." N. Engl. J. Med., vol. 366, pp. 2455-2465 (2012).
Brett et al., "Phase II study of anti-gastrin-17 antibodies, raised to G17DT, in advanced pancreatic cancer." J. Clin. Oncol., vol. 20, pp. 4225-4231 (2002).
Brett et al., "Lymphocyte Expression of the CCK-B/Gastrin Receptor (CCK-BR) in Gastric Lymphomas, Helicobacter pylori Gastritis and Normal Gastric Biopsies," Gastroenterology. vol. 114, No. 4, Suppl. 1 p. A570 (1998) [Abstract # G2333].
Brett et al., "The Effect of Antibodies Raised Against Gastrimmune On the Proliferation of Human Pancreatic Carcinoma Cell Lines," Gut. vol. 42 p. A26 (1998) [Abstract # W190].
Brinton et al., "Cancer risk following pernicious anaemia," Br. J. Cancer. vol. 59, No. 5 pp. 810-813 (1989).
Bruns et al., "Therapy of Human Pancreatic Carcinoma Implants by Irinotecan and the Oral Immunomodulator JBT 3002 Is Associated with Enhanced Expression of Inducible Nitric Oxide Synthase in Tumor-infiltrating Macrophages," Cancer Research. vol. 60 pp. 2-7 (2000).
Buchan et al., "Regulatory Peptides in Barrett's Esophagus," Journal of Pathology. vol. 146, No. 3 pp. 227-234 (1985).
Burkitt et al., "Importance of gastrin in the pathogenesis and treatment of gastric tumors," World J. Gastroenterol. vol. 15, No. 1 pp. 1-16 (2009).
Burks et al., "Cholecystokinin Receptor-Targeted Polyplex Nanoparticle Inhibits Growth and Metastasis of Pancreatic Cancer." Cell. Mol. Gastroent. Hepatol., vol. 6(1), pp. 17-32 (2018).
Burris III et al., "Improvements in survival and clinical benefit with gemcitabine as first-line therapy for patients with advanced pancreas cancer: a randomized trial," Journal of Clinical Oncology. vol. 15, No. 6 pp. 2403-2413 (1997).
Bystryn, J., "Tumor vaccines," Cancer and Metastasis Reviews. vol. 9 pp. 81-91 (1990).
Caplin et al., "Effect of Gastrin and Anti-Gastrin Antibodies on Proliferation of Hepatocyte Cell Lines," Digestive Diseases and Sciences. vol. 46, No. 7 pp. 1356-1366 (2001).
Caplin et al., "Expression and processing of gastrin in hepatocellular carcinoma, fibromellar carcinoma and cholangiocarcinoma," Journal of Hepatology. vol. 30, No. 3 pp. 519-526 (1999).
Caplin et al., "Expression and processing of gastrin in pancreatic adenocarcinoma," Brit. J. Surgery. vol. 87 pp. 1035-1040 (2000).
Caplin et al., "Expression and Processing of Gastrin in Patients with Pancreatic Carcinoma," Gastroenterology. vol. 114, Suppl. 1 p. A445 (1998) [Abstract # G1809].
Caplin et al., "Serum Gastrin Levels and Identification of CCK-B/gastrin Receptor Following Partial Hepatectomy for Liver Tumours in Man," Gastroenterology. vol. 110, Suppl. 4 p. A1162 (1996) [Abstract].

(56) References Cited

OTHER PUBLICATIONS

Caplin et al., "The CCK-B/Gastrin Receptor In Hepatocellular Carcinoma," Gastroenterology. vol. 110, No. 4 p. A1162 (1996) [Abstract].
Caplin et al. "Demonstration of new sites of expression of the CCK-B/gastrin receptor in pancreatic acinar AR42J cells using immunoelectron microscopy," Regulatory Peptides. vol. 84, No. 1-3 pp. 81-89 (1999).
Caplin et al., "Expression and Processing of Gastrin in Patients with Hepatocellular Carcinoma, Fibrolamellar Carcinoma and Cholangiocarcinoma," Gastroenterology. vol. 114, Suppl. I p. A1219 (1998) [Abstract # L0083].
Casper et al., "Phase II trial of gemcitabine (2,2'-difluorodeoxycitidine) in patients with adenocarcinoma of the pancreas," Investigational New Drugs. vol. 12, No. 1 pp. 29-34 (1994) [Abstract].
Certificate of Patent corresponding to Japanese Patent Application No. 2006-509465 dated Feb. 25, 2011.
Certified English Translation of PCT Patent Application No. WO 2001/13114, "Use of stabilized synthetic compounds in immunoassay." Publication date: Feb. 22, 2001.
Chaudhry et al., "Phase I and Imaging Trial of a Monoclonal Antibody Directed Against Gastrin-releasing Peptide in Patients with Lung Cancer," Clinical Cancer Researc. vol. 5 pp. 3385-3393 (1999).
Choudhury et al., "N-Terminal Sequence of Human Big Gastrin: Sequence, Synthetic and Immunochemical Studies," A76 Hoppe-Seyler's Z. Physiol. Chem. vol. 361 pp. 1719-1733 (1980).
Ciccotosto et al., "Expression, Processing, and Secretion of Gastrin in Patients With Colorectal Carcinoma," Gastroenterology. vol. 109, No. 4 pp. 1142-1153 (1995).
Clerc et al., "Differential Expression of the CCK-A and CCK-B/Gastrin Receptor Genes in Human Cancers of the Esophagus, Stomach, and Colon," International Journal of Cancer. vol. 72 pp. 931-936 (1997).
Cole, "Immunoassay of human chorionic gonadotropin, its free subunits, and metabolites," Clinical Chemistry. vol. 43, No. 12 pp. 2233-2243 (1997).
Decision to Grant a European Patent Pursuant to Article 97(1) EPC corresponding to European Patent Application No. 05 784 499.5-2406 / 1794586 dated Jan. 7, 2013.
Decision to Grant corresponding to Japanese Patent Application No. 2006-310647 dated Dec. 18, 2012. [Translation].
Decision to Grant corresponding to Japanese Patent Application No. 2011-034753 dated Dec. 18, 2012. [Translation].
Decision to Grant corresponding to Japanese Patent Application No. 2020-519008 dated Mar. 12, 2024.
Decision of Patent Grant corresponding to Korean Patent Application No. 10-2007-7009115 dated Aug. 21, 2013. [Translation].
De Jong et al., "Effects of partial liver resection on tumor growth," Journal of Hepatology. vol. 25 pp. 109-121 (1996).
De Magistris, L., and Rehfeld, J.F., "A Simple Enzymatic Procedure for Radioimmunochemical Quantitation of the Large Molecular Forms of Gastrin and Cholecystokinin," Analytical Biochemistry. vol. 102 pp. 126-133 (1980).
Deed of Letters Patent corresponding to Australian Patent Application No. 2004225437 dated Aug. 26, 2010.
Deed of Letters Patent corresponding to Australian Patent Application No. 2005286164 dated Sep. 6, 2012.
Delitto et al. (2016) "Targeting tumor tolerance: A new hope for pancreatic cancer therapy?", Pharmacology & Therapeutics, Elsevier, GB, vol. 166, pp. 9-29.
Demeester et al., "Patterns of Gastroesophageal Reflux in Health and Disease," Ann. Surg. vol. 184, No. 4 pp. 459-469 (1976).
De Weerth et al., "Human Pancreatic Cancer Cell Lines Express the CCKB Receptor," Hepato-Gastroenterology. vol. 46 pp. 472-478 (1999).
De Weerth et al., "Human Pancreatic Cancer Cell Lines Express the CCKB/Gastrin Receptor," Gastroenterology. vol. 106, No. 4 p. A289 (1994) [Abstract].

Del Valle et al., "Progastrin and Its Glycine-Extended Post-translational Processing Intermediates in Human Gastrointestinal Tissues," Gastroenterology. vol. 92, No. 6 pp. 1908-1912 (1987).
Dethloff et al., "Inhibition of Gastrin-Stimulated Cell Proliferation by the CCK-B/gastrin Receptor Ligand CI-988," Food and Chemical Toxicology. vol. 37 pp. 105-110 (1999).
Dickinson, C.J., and Yamada, T., "Gastrin-amidating Enzyme in the Porcine Pituitary and Antrum," The Journal of Biological Chemistry. vol. 266, No. 1 pp. 334-338 (1991).
Dickinson, "Relationship of Gastrin Processing to Colon Cancer," Gastroenterology. vol. 109, No. 4 pp. 1384-1388 (1995).
Dockray, G.J., and Walsh, J.H., "Amino-Terminal Gastrin Fragment in Serum of Zollinger-Ellison Syndrome Patients," Gastroenterology. vol. 68, No. 2 pp. 222-230 (1975).
Dockray et al., "Gastric Endocrine Cells: Gene Expression, Processing, and Targeting of Active Products," Physiological Review. vol. 76, No. 3 pp. 767-798 (1996).
Dockray et al., "Immunochemical studies on big gastrin using NH2-terminal specific antiserums," Regulatory Peptides. vol. 1, No. 3 pp. 169-186 (1980). Chemical Abstracts vol. 94 pp. 506-507 (1981) [Abstract #94:119200w].
Dockray et al., "The Gastrins: Their Production and Biological Activities," Ann. Rv. Physiol. vol. 63 pp. 119-139 (2001).
Dockray, G.J., and Taylor, I.L., "Heptadecapeptide Gastrin: Measurement in Blood by Specific Radioimmunoassay", Gastroenterology. vol. 71, No. 6 pp. 971-977 (1976).
Dockray, "Immunochemical Studies on Big Gastrin Using NH2-Terminal Specific Antisera," Regulatory Peptides. vol. 1 pp. 169-186 (1980).
Douziech et al. "Growth Effects of Regulatory Peptides and Intracellular Signaling Routes in Human Pancreatic Cancer Cell Lines," Endocrine. vol. 9, No. 2 pp. 171-183 (1998).
Du et al. "Biochip as a potential platform of serological interferon (2b antibody assay," Journal of Biotechnology. vol. 106, No. 1 pp. 87-100 (2003).
Dufresne et al., "Cholecystokinin and Gastrin Receptors," Physiol. Rev. vol. 86 pp. 805-847 (2006).
Edgington, "Biotech Vaccines' Problematic Promise," Bio/Technology. vol. 10 pp. 763-766 (1992).
Edkins, "On the Chemical Mechanism of Gastric Secretion," Proceedings of the Royal Society of London. Series B, Containing Papers of a Biological Character. vol. 76, No. 510 p. 376 (1905).
Edkins, "The Chemical Mechanism of Gastric Secretion," J. Physiol. vol. 34, Nos. 1-2 pp. 133-144 (1906).
Erlichman et al., "A Randomized Trial of Fluorouracil and Colonic Acid in Patients With Metastatic Colorectal Carcinoma," Journal of Clinical Oncology. vol. 6 pp. 469-475 (1988).
European Search Report corresponding to European Patent Application No. 12176933.5-1412 / 2567974 dated Apr. 24, 2013.
Extended European Search Report corresponding to European Patent Application No. 18816949.4-1118 / 3624841 dated Jan. 12, 2021.
Evans, "Chemotherapy in Advanced Non-Small Cell Lung Cancer," 37th Annual Meeting of the American Society of Clinical Oncology, Day 1, May 22, 2001, meeting report published by Medscape.
Ezzell, "Cancer 'Vaccines': An Idea Whose Time Has Come?" The Journal of NIH Research. vol. 7 pp. 46-49 (1995).
Fennerty, "Updated on Barrett's Esophagus" Digestive Diseases Week, May 22, 2001, meeting report published by Medscape, www.medscape.com, 6 pages.
Festen et al., "Effect of Oral Omeprazole on Serum Gastrin and Serum Pepsinogen I Levels," Gastroenterology. vol. 87, No. 5 pp. 1030-1034 (1984).
Fields, "Preparation of Antipeptide Antibodies: Introduction to Peptide Synthesis," Current Protocols in Molecular Biology. 11.15.1-11.15.9 (2002).
Feurle et al. "The Role of CCK and its Analogues in the Organogenesis of the Fetal Rat Pancreas," Pancreas. vol. 10, No. 3 pp. 281-286 (1995).
Finley et al., "Expression of the Gastrin Gene in the Normal Human Colon and Colorectal Adenocarcinoma," Cancer Research. vol. 53 pp. 2919-2926 (1993).

(56) References Cited

OTHER PUBLICATIONS

Fino et al., "Downregulation of the CCK-B receptor in pancreatic cancer cells blocks proliferation and promotes apoptosis." Am. J. Physiol. Gastrointest. Liver Physiol., vol. 302, pp. G1244-G1252 (2012).
Fornai et al., "Cholecystokinin CCK2 receptors mediate the peptide's inhibitory actions on the contractile activity of human distal colon via the nitric oxide pathway," British Journal of Pharmacology. vol. 151 pp. 1246-1253 (2007).
Fourmy et al., "Relationship of CCK/gastrin-receptor binding to amylase release in dog pancreatic acini," Regulatory Peptides. vol. 10 pp. 57-68 (1984).
Fraser, "Effects of Antibodies to Luteinizing Hormone Releasing Hormone On Reproductive Functions In Rodents," Immunization With Hormones in Reproduction Research. Nieschlag ed. North Holland Publishing. pp. 107-117 (1975).
Freston, "Long-Term Acid Control and Proton Pump Inhibitors: Interactions and Safety Issues in Perspective," American Journal of Gastroenterology. vol. 92, No. 4 pp. 51S-57S (1997).
Frucht et al., "Characterization of Functional Receptors for Gastrointestinal Hormones on Human Colon Cancer Cells," Cancer Research. Vol. 52, No. 5 pp. 1114-1122 (1992).
Geysen et al.(1988) Cognitive Features of Continuous Antigenic Determinants. Journal of Molecular Recognition 1(1):32-41.
Ghrib et al., Arachidonic-Acid-Selective Cytosolic Phospholipase A2 Is Involved in Gastrin-Induced AR4-2J-Cell Proliferation, International Journal of Cancer. vol. 75 pp. 239-245 (1998).
Gil-Delgado et al., "Prospective Phase II Trial of Irinotecan, 5-Fluorouracil, and Leucovorin in Combinations as Salvage Therapy for Advanced Colorectal Cancer," American Journal of Clinical Oncology. vol. 24, No. 1 pp. 101-105 (2001).
Gilliam et al., "A phase II study of G17DT in gastric carcinoma," EJSO. vol. 30 pp. 536-543 (2004).
Gilliam et al., "An international multicenter randomized controlled trial of G17DT in patients with pancreatic cancer." Pancreas, vol. 41, pp. 374-379 (2012).
Gilliam et al. (2007) "G17DT: an antigastrin immunogen for the treatment of gastrointestinal malignancy," Expert Opinion Biol. Ther. vol. 7, No. 3 pp. 397-404 (2007).
Gilliam et al., "Randomized, double blind, placebo-controlled, multi-centre, group-sequential trial of G17DT for patients with advanced pancreatic cancer unsuitable or unwilling to take chemotherapy," Journal of Clinical Oncology. ASCO Annual Meeting Proceedings. vol. 22, No. 14S p. 2511 (2004) [Abstract].
Gisbert et al., "Decrease in gastrin levels after H. pylori eradication," Revista espanola de enfermedades digestivas (Spanish Journal of Gastroenterology). vol. 87, No. 2 pp. 99-107 (1995) [Abstract].
Gocyk et al. "Helicobacter pylori, gastrin and cyclooxygenase-2 in lung cancer," Med. Sci. Monit. vol. 6, No. 6 pp. 1085-1092 (2000).
Goetze, J.P., and Rehfeld, J.F., "Impact of Assay Epitope Specificity in Gastrinoma Diagnosis," Clinical Chemistry. vol. 49, No. 2 pp. 333-334 (2003).
Goletti et al. "Resection of Liver Gastrinoma Leading to Persistent Eugastrinemia," Eur. J. Surgery. vol. 158 pp. 55-57 (1992).
Grabowska, A., and Watson, S.A., "Downregulation of the Gastrin Gene Using Small Interfering RNA," Regulatory Peptides. vol. 122, No. 1 p. 46 (2004) [Abstract # A150].
Gregory, R.A., and Tracy, H.J., "Isolation of Two Gastrins from Human Antral Mucosa," Nature. vol. 209, No. 5023 p. 583 (1966).
Grider, J.R., and Makhlouf, G.M., "Distinct receptors for cholecystokinin and gastrin on muscle cells of stomach and gallbladder," Am. J. Physiol. vol. 259 pp. G184-G190 (1990).
Gupta, J.R., and Siber, G.R., "Adjuvants for human vaccines—current status, problems and future prospects," Vaccine. vol. 13, No. 14 pp. 1263-1276 (1995).
Gura, T., "Systems for Identifying New Drugs Are Often Faulty," Science. vol. 278, No. 5340 pp. 1041-1042 (1997).
Gutman et al., "Accelerated Growth of Human Colon Cancer Cells in Nude Mice Undergoing Liver Regeneration," Invasion and Metastasis. vol. 14, Nos. 1-6 pp. 362-371 (1994-95).

Haigh et al. "Gastrin Induces Proliferation in Barrett's Metaplasia Through Activation of the CCK2 Receptor," Gastroenterology. vol. 124 pp. 615-625 (2003).
Halter et al., "Evaluation of a Monoclonal Anti-Gastrin Antibody As a Tool for Immunoneutralization of Gastrin During Omeprazole Treatment in the Rat," Gastroenterology. vol. 96, No. 5, Part 2 p. A194 (1989).
Hananel et al., "Hepatic Resection for Colorectal Liver Metastasis," The American Surgeon. vol. 61, No. 5 pp. 444-447 (1995).
Harlow, E., and Lane, D., Antibodies: A Laboratory Manual, Cold Spring Harbor Laboratory Press. Cold Spring Harbor, NY. pp. 7-13, 23-26, 142-143, 148-149 (1988).
Harlow, E., and Lane, D., Antibodies: A Laboratory Manual. Cold Spring Harbor Laboratory Press. Cold Spring Harbor, NY. pp. 555-556, 559, 561, 578-581, and 591-593 (1988).
Harris et al., "An Antiapoptotic Role for Gastrin and the Gastrin/CCK-2 Receptor in Barrett's Esophagus," Cancer Research. vol. 64, No. 6 pp. 1915-1919 (2004).
Harris et al., "The Biological and Therapeutic Importance of Gastrin Gene Expression in Pancreatic Adenocarcinomas," Cancer Research. vol. 64 pp. 5624-5631 (2004).
Harrison et al. "The Effect of the Gastrin Receptor Antagonist Proglumide on Survival in Gastric Carcinoma," Cancer. vol. 66, No. 7 pp. 1449-1452 (1990).
He et al., "Biological Activity and Ferric Ion Binding of Fragments of Glycine-Extended Gastrin," Biochemistry. vol. 43, No. 37 pp. 1853-11861 (2004).
He, A.R., and Marshall, J.L., "Clinical experiences with G17DT in gastrointestinal malignancies," Expert Rev. Anticancer Ther. vol. 6, No. 4 pp. 487-492 (2006) [Abstract].
Heinemann et al., "Cellular Elimination of 2',2'-Diflourodeoxycytidine 5'-Triphosphate: A Mechanism of Self-Potentiation," Cancer Research. vol. 52 pp. 533-539 (1992).
Helander et al., "Immunohistochemical localization of gastrin/CCK-B receptors in the dog and guinea-pig stomach," Acta Physiologica Scandinavica. vol. 159, No. 4 pp. 313-320 (1997).
Hellmich et al., "Human Colorectal Cancers Express a Constitutively Active Cholecystokinin-B/Gastrin Receptor That Stimulates Cell Growth," The Journal of Biological Chemistry. vol. 275, No. 41 pp. 32122-32128 (2000).
Henwood et al., "Expression of gastrin in developing gastric adenocarcinoma," British Journal of Surgery. vol. 88 pp. 564-568 (2001).
Herbert et al. (Eds.) "The Dictionary of Immunology," 3rd Ed. Academic Press, London, p. 41 (1995).
Herbst et al., "Predictive correlates of response to the anti-PD-L1 Ab MPDL3280A in cancer patients." Nature, vol. 515, pp. 563-567 (2014).
Herget et al., "Cholecystokinin Stimulates Ca2+ Mobilization and Clonal Growth in Small Cell Lung Cancer through CCKA and CCKB/Gastrin Receptors," Annals New York Academy of Sciences. vol. 713, pp. 283-297 (1994).
Hoosein et al., "Antiproliferative Effects of Gastrin Receptor Antagonists and Antibodies to Gastrin on Human Colon Carcinoma Cell Lines," Cancer Research. vol. 48 pp. 7179-7183 (1988).
Hoosein et al., "Evidence for Autocrine Growth Stimulation of Cultured Colon Tumor Cells by a Gastrin/Cholecystokinin-like Peptide," Experimental Cell Research. vol. 186, No. 1 pp. 15-21 (1990).
Houghten et al., "Relative Importance of Position and Individual Amino Acid Residues in Peptide Antigen-Antibody Interactions: Implications in the Mechanism of Antigenic Drift and Antigenic Shift," Vaccines. vol. 86 pp. 21-25 (1986).
Hsi, "A Practical Approach for Evaluating New Antibodies in the Clinical Immunohistochemistry Laboratory," Arch. Pathol. Lab. Med. vol. 125 pp. 289-294 (2001).
Huang et al., "Termination of DNA Synthesis by 9-(-D-Arabinofuranosyl-2-fluroadenine," The Journal of Biological Chemistry. vol. 265, No. 27 pp. 16617-16625 (1990).
Hughes et al., "Development of a class of selective cholecystokinin type B receptor antagonists having potent anxiolytic activity," PNAS. vol. 87 pp. 6728-6732 (1990).

(56) References Cited

OTHER PUBLICATIONS

Hughes et al., "Therapy with Gastrin Antibody in the Zollinger-Ellison Syndrome," Digestive Diseases. vol. 21 pp. 201-204 (1976).
Ichikawa et al., "Distinct effects of tetragastrin, histamine, and CCh on rat gastric mucin synthesis and contribution of NO," Am. J. Physiol. vol. 274, No. 1 pp. G138-G146 (1998).
Ikeda et al., "Preliminary report of tumor metastasis during liver regeneration after hepatic resection in rats," European Journal of Surgical Oncology. vol. 21, No. 2 pp. 188-190 (1995).
Intent to Grant corresponding to European Patent Application No. 05 784 499.5-2406 dated Aug. 13, 2012.
International Preliminary Examination Report corresponding to International Patent Application No. PCT/US1999/010734 dated Dec. 9, 2000.
International Preliminary Examination Report corresponding to International Patent Application No. PCT/US2002/021768 dated Feb. 9, 2004.
International Preliminary Report on Patentability corresponding to International Patent Application No. PCT/US2005/010532 dated Nov. 3, 2006.
International Preliminary Examination Report corresponding to International Patent Application No. PCT/US2002/008756 dated May 26, 2006.
International Preliminary Report on Patentability corresponding to International Patent Application No. PCT/US2004/009666 dated Jan. 19, 2006.
International Preliminary Report on Patentability corresponding to International Patent Application No. PCT/US2018/037737 dated Feb. 28, 2020.
International Search Report corresponding to International Patent Application No. PCT/US1990/000520 dated May 21, 1990.
International Search Report corresponding to International Patent Application No. PCT/US2004/009666 dated Nov. 8, 2004.
International Search Report corresponding to International Patent Application No. PCT/US2005/010532 dated Feb. 8, 2006.
International Search Report corresponding to International Patent Application No. PCT/US1999/010751 dated Oct. 19, 1999.
International Search Report corresponding to International Patent Application No. PCT/IB2005/002793 dated Dec. 7, 2005.
International Search Report and Written Opinion corresponding to International Patent Application No. PCT/US 22/12294 dated Apr. 28, 2022.
Interview Summary corresponding to U.S. Appl. No. 11/663,126 dated Nov. 15, 2011.
Interview Summary corresponding to U.S. Appl. No. 16/622,841 dated Apr. 8, 2022.
Iwanaga et al., "Immunocytochemical Localization of the Different Gastrin Forms in the Pyloric Antrum," Biomedical Research. vol. 1 pp. 316-320 (1980).
Iwao et al., "Effects of Omeprazole and Lansoprazole on Fasting and Postprandial Serum Gastrin and Serum Pepsinogen A and C," Hepato-Gastroenterology. vol. 42 pp. 677-682 (1995).
Iwase et al., "Regulation of Growth of Human Gastric Cancer by Gastrin and Glycine-Extended Progastrin," Gastroenterology. vol. 113 pp. 782-790 (1997).
Jaffe et al., "Gastrin resistance following immunization to the C-terminal tetrapeptide amide of gastrin," Surgery. vol. 69, No. 2 pp. 232-237 (1971).
Jaffe et al., "Inhibition of Endogenous Gastrin Activity by Antibodies to the Carboxyl-Terminal Tetrapeptide Amide of Gastrin," Gastroenterology. vol. 58, No. 2 pp. 151-156 (1970).
Jaffe et al., "Inhibition of gastrin activity by incubation with antibodies to the C-terminal tetrapeptide of gastrin," Surgery. vol. 65, No. 4 pp. 633-639 (1969).
Jain, "Barriers to Drug Delivery in Solid Tumors," Scientific American. vol. 171, No. 1 pp. 58-65 (1994).
Janeway et al. "Immunobiology: The Immune System in Health and Disease," Fourth Edition, Elsevier Science Ltd./Garland Publishing, New York, NY p. 544 (1999).
Jansen et al., "Effect of Long-Term Treatment with Omeprazole on Serum Gastrin and Serum Group A and C Pepsinogens in Patients with Reflux Esophagitis," Gastroenterology. vol. 99, No. 3 pp. 621-628 (1990).
Johnson et al, "Ornithine Decarboxylase in Large Bowel Mucosa: Regulation by Gastrin, Secretin and EGF," Journal of Physiology and Pharmacology. vol. 43, No. 1 pp. 33-41 (1992).
Johnson, "New Aspects of the Trophic Action of Gastrointestinal Hormones," Gastroenterology. vol. 72, No. 4, Part 2 pp. 788-792 (1977).
Jonsson, A., and Dockray, G.J., "Immunohistochemical localization to pyloric antral G cells of peptides derived from porcine preprogastrin," Regulatory Peptides. vol. 8 pp. 283-290 (1984).
Joshi, S.N., and Gardner, J.D., "Gastrin and Colon Cancer: A Unifying Hypothesis," Digestive Diseases. vol. 14 pp. 334-344 (1996).
Justin et al., "Gastric Acid Suppression Using Anti-Gastrin-17 Antibodies Produced by a Gastrin Immunogen, Gastrimmune, in An In Vivo Pig Model," Gastroenterology. vol. 108, No. 4 p. A125 (1995) [Abstract].
Kaiser, "First Pass at Cancer Genome Reveals Complex Landscape," Science. vol. 313 p. 1370 (2006).
Kameyama et al., "Adjuvant Chemo-Endocrine Chemotherapy with Gastrin Antagonist After Resection of Liver Metastasis in Colorectal Cancer," Japanese Journal of Cancer and Chemotherapy. vol. 21, No. 13 pp. 2169-2171 (1994) [Abstract].
Katoh et al., "Malignant Zollinger-Ellison Syndrome. Stabilizing of Liver Metastasis After Gastrectomy with Resection of Primary Tumor," The American Surgeon. vol. 56, No. 6 pp. 360-363 (1990).
Kaufmann et al., "Cholecystokinin B-type receptor signaling is involved in human pancreatic cancer cell growth," Neuropeptides. vol. 31, No. 6 pp. 573-583 (1997).
Kelley et al., "Antitumor Activity of a Monoclonal Antibody Directed Against Gastrin-Releasing Peptide in Patients with Small Cell Lung Cancer," Chest. vol. 112 pp. 256-261 (1997).
Kelly et al., "Pathophysiology of GI Tract and Liver: Expression of progastrin-derived peptides and gastrin receptors in a panel of gastrointestinal carcinoma cell lines," Journal of Gastroenterology and Hepatology. vol. 13 pp. 208-214 (1998).
Kim et al., "Abstract 2340: PD-1 blockade suppresses gastric cancer development by promoting antitumor immunity in mice," Cancer Research, 76(14 Suppl): Abstract No. 2340, 3 pages (2016).
Kipriyanov, S.M., and Little, M., "Generation of Recombinant Antibodies," Molecular Biotechnology. vol. 12 pp. 173-201 (1999).
Kobori et al., "Growth Responses of Rat Stomach Cancer Cells to Gastro-Entero-Pancreatic Hormones," International Journal of Cancer. vol. 30, No. 1 pp. 65-67 (1982).
Kochman et al., "Post-Translational Processing of Gastrin in Neoplastic Human Colonic Tissues," Biochemical and Biophysical Research Communications. vol. 189, No. 2 pp. 1165-1169 (1992).
Koelz, "Treatment of Reflux Esophagitis with H2-Blockers. Antacids and Prokinetic Drugs. An Analysis of Randomized Clinical Trials," Scandinavian Journal of Gastroenterology. Supplement 156 pp. 25-36 (1989).
Koh et al., "Gastrin Deficiency Results in Altered Gastric Differentiation and Decreased Colonic Proliferation in Mice," Gastroenterology. vol. 113, No. 3 pp. 1015-1025 (1997).
Koh et al., "Glycine-Extended Gastrin Promotes the Growth of Lung Cancer," Cancer Research. vol. 64 pp. 196-201 (2004).
Koh et al., "Glycine-Extended Gastrin Promotes the Growth of a Human Hepatoma Cell Line," Gastroenterology. vol. 110, No. 4 p. A1089 (1996) [Abstract].
Kohler et al., "Continuous cultures of fused cells secreting antibody of predefined specificity," Nature. vol. 256 pp. 495-497 (1975).
Kopin et al. "Expression, cloning and characterization of the canine parietal cell gastrin receptor," PNAS. vol. 89 pp. 3605-3609 (1992).
Kothary, P.C., and Lvinik, A., "NH2-Terminal of Gastrin-17 in Duodenal Ulcer Disease: Identification of Progastrin-17," Biochemical and Biophysical Research Communications. vol. 146, No. 2 pp. 884-888 (1987).
Kothary et al., "Identification of gastrin molecular variants in gastrinoma syndrome," Regulatory Peptides. vol 17 pp. 71-84 (1987).

(56) References Cited

OTHER PUBLICATIONS

Kovacs et al., "Gastrin Partially Mediates Insulin-Induced Acid Secretion in Dogs," Peptides. vol. 17, No. 4 pp. 583-587 (1996).
Kovacs et al., "Gastrin Is a Major Mediator of the Gastric Phase of Acid Secretion in Dogs: Proof by Monoclonal Antibody Neutralization," Gastroenterology. vol. 97 pp. 1406-1413 (1989).
Kovacs et al. "Inhibition of sham feeding-stimulated acid secretion in dogs by immunoneutralization of gastrin," Am. J. Physiol. vol. 273 (Gastrointest. Liver Physiol. 36) pp. G399-G403 (1997).
Koyama et al., "Functional Role of Gastrin-Releasing Peptide on the Growth of Pancreatic Cancer Cells in vitro," History of Medicine. vol. 156, No. 4 pp. 285-286 (1991) [Abstract].
Kuipers et al., "The Efficacy and Safety of Long-term Omeprazole Treatment for Gastroesophageal Reflux Disease," Gastroenterology. vol. 118, No. 4 pp. 795-798 (2000).
Kuipers et al., "Atrophic Gastritis and Helicobacter pylori Infection in Patients with Reflux Esophagitis Treated with Omeprazole or Fundoplication," New England Journal of Medicine. vol. 334, No. 16 pp. 1018-1022 (1996).
Kusyk et al., "Stimulation of growth of a colon cancer cell line by gastrin," Am. J. Physiol. vol. 251 pp. G597-G601 (1986).
Lamberts et al., "Effects of Very Long (up to 10 years) Proton Pump Blockade on Human Gastric Mucosa," Digestion. vol. 64 pp. 205-213 (2001).
Lamers, C.B.H.W., and Jansen, J.B.M.J., "Role of Gastrin and Cholecystokinin in Tumours of the Gastrointestinal Tract," Eur. J. Cancer Clin. Oncol. vol. 24, No. 2 pp. 267-273 (1988).
Lamote, J., and Willems, G., "Stimulating effect of pentagastrin on cancer cell proliferation kinetics in chemically induced colon cancer in rats, " Regulatory Peptides. vol. 20 pp. 1-9 (1988).
Landis et al., "Cancer Statistics, 1998" CA—A Cancer Journal for Clinicians. vol. 48, No. 1 pp. 6-30 (1998).
Larsson, L., and Rehfeld, J.F., "Characterization of Antral Gastrin Cells With Region-Specific Antisera," The Journal of Histochemistry and Cytochemistry. vol. 25, No. 12 pp. 1317-1321 (1977).
Larsson, "Histochemistry of Gastrin Cells," Neurohistochemistry: Modern Methods and Applications. Alan R. Liss, Inc., pp. 527-567 (1986).
Laurie, S.A., and Kris, M.G., "Single-Agent Docetaxel (Taxotere) in the Treatment of Advanced Non-Small-Cell Lung Cancer: Clinical Concepts and Commentary," Clinical Lung Cancer. vol. 1, Suppl 1 pp. S5-S9 (2000).
Lawrence et al., "Radiosensitization of Pancreatic Cancer Cells by 2', 2'-Difluoro-2'-Deoxycytidine," Int. J. Radiation Oncology Biol. Phys. vol. 34, No. 4 pp. 867-872 (1996).
Le Meuth et al., "Differential Expression of A- and B-Subtypes of Cholecystokinin/Gastrin-Receptors in the Developing Calf Pancreas," Endocrinology. vol. 133, No. 3 pp. 1182-1191 (1993).
Leach et al., "Enhancement of antitumor immunity by CTLA-4 blockade." Science, vol. 271, pp. 1734-1736 (1996).
Ledda-Columbano et al., "Compensatory Regeneration, Mitogen-Induced Liver Growth, and Multistage Chemical Carcinogenesis," Environmental Health Perspectives. vol. 101, No. 5 pp. 163-168 (1993).
Lee et al., "The Human Brain Cholecystokinin-B/Gastrin Receptor," The Journal of Biological Chemistry. vol. 268, No. 11 pp. 8164-8169 (1993).
Leith et al., "Effects of Partial Hepatectomy on Growth Characteristics and Hypoxic Fractions of Xenografted DLD-2 Human Colon Cancers," Radiation Research. vol. 132, No. 2 pp. 263-268 (1992).
Letter regarding Third Office Action corresponding to Chinese Patent Application No. 200580017341.9 dated Mar. 31, 2015.
Letter regarding Fourth Office Action corresponding to Chinese Patent Application No. 200580017341.9 dated Oct. 12, 2015.
Li et al., "Induction of growth inhibition and apoptosis in pancreatic cancer cells by auristatin-PE and gemcitabine," International Journal of Molecular Medicine. vol. 3 pp. 647-653 (1999).
Lutz et al., "Priming the pancreatic cancer tumor microenvironment for checkpoint-inhibitor immunotherapy." Oncoimmunology, vol. 3, Article ID e962401 (2014).
Machine translation of JP 06107564 (1994).
MacKenzie et al., "Development of a Radioligand Binding Assay to Characterise Gastrin Receptors in the Human Gastrointestinal Tract," Gut. vol. 38, Suppl. 1 p. A37 (1996) [Abstract # T146].
Mahood et al., "Inhibition of Fluorouracil Stomatitis by Oral Cryotherapy," Journal of Clinical Oncology. vol. 9 pp. 449-452 (1991).
Makishima et al., "Inhibition of Gastrin-17 Stimulated Acid Secretion Through Active Immunization in Rats," FASEB Journal. vol. 8, Nos. 4-5 p. A92 (1994) [Abstract #535].
Makishima et al., "Active Immunization Against Gastrin-17 With an N-Terminal Derived Immunogen Inhibits Gastric and Duodenal Lesions in Rats," Gastronenterology. vol. 106, No. 4, Part. 2 p. A824 (1994) [Abstract].
Mandair et al., "Cholecystokinin Receptors in Human Pancreatic Cancer Cell Lines," European Journal of Cancer. vol. 34, No. 9 pp. 1455-1459 (1998).
Marino et al., "Expression and Post-translational Processing of Gastrin in Heterologous Endocrine Cells," The Journal of Biological Chemistry. vol. 266, No. 10 pp. 6133-6136 (1991).
Martin et al. "Selection of Trypsin of 2 Sublines of Rat Cancer Cells Forming Progressive or Regressive Tumors," Int. J. Cancer. vol. 32 pp. 623-627 (1983).
Masseyeff, R.F., and Ferrua, B., "The Art of Assay Design in Heterologous Enzyme Immunoassay," International symposium on immunoenzymatic techniques. vol. 2 pp. 139-154 (1983).
Matsumoto et al. "Gastrin receptor characterization: affinity cross-linking of the gastrin receptor on canine gastric parietal cells," Am J. Physiol. vol. 252 p. G143-G147 (1987).
McCloy et al., "Pathophysiological Effects of Long-Term Acid Suppression in Man," Digestive Diseases and Sciences. vol. 40, No. 2 p. 96S-120S [Supplement] (1995).
McGregor et al., "Trophic Effects of Gastrin on Colorectal Neoplasms in the Rat," Ann. Surg. vol. 195, No. 2 pp. 219-223 (1982).
McRae et al., "Role of Gastrin and Gastrin Receptors in the Growth of Human Colon Carcinoma Cells," The Journal of Cell Biology. vol. 103, No. 5, Part 2 p. 22a (1986) [Abstract # 74].
McWilliams et al., "Antibodies raised against the extracellular tail of the CCKB/gastrin receptor inhibit gastrin-stimulated signalling," Regulatory Peptides. vol. 99, Nos. 2-3 pp. 157-161 (2001).
McWilliams et al., "Coexpression of gastrin and gastrin-receptors (CCK-B and CCK-B) in gastrointestinal tumour cell lines," Gut. vol. 42 pp. 795-798 (1998).
Miermont et al. "Cowpea Mosaic Virus Capsid, a Promising Carrier for the Development of Carbohydrate Based Anti-tumor Vaccines," Author Manuscript, 21 pages, Published in final edited form as: Chemistry, 14(16), pp. 4939-4947 (2008).
Mishell, B.B., and Shiigi, S.M., "Selected Methods in Cellular Immunology," Chapter 17: Immunoglobulin-Producing Hybrid Cell Lines, W.H. Freeman and Co.: San Francisco pp. 368-370 (1980).
Miyake, "A Truncated Isoform of Human CCK-B/Gastrin Receptor Generated by Alternative Usage of a Novel Exon," Biochemical and Biohysical Research Communications. vol. 208, No. 1 pp. 230-237 (1995).
Mizutani et al., "Promotion of hepatic metastases by liver resection in the rat," British J. Cancer. vol. 65, No. 6 pp. 794-797 (1992).
Moertel, C.G., "Chemotherapy for Colorectal Cancer," The New England Journal of Medicine. vol. 330, No. 16 pp. 1136-1142 (1994).
Molina et al., "Pro-gastrin-releasing peptide in patients with benign and malignant diseases," Tumour Biology. vol. 25, Nos. 1-2 pp. 56-61 (2004) [Abstract].
Moody et al., "GRP Receptors Are Present in Non Small Cell Lung Cancer Cells," Journal of Cellular Biochemistry Supplement. vol. 24 pp. 247-256 (1996).
Moroder, L., and Wunsch, E., "Gastrins and Cholecystokinins: Chemical and Immunological Aspects," Gastrin and Cholecystokinin. Chemistry, physiology and pharmacology. (Ed. J. Bali et al.) Elsevier Science Publishers B.V. pp. 21-32 (1987).
MSNBC News Services, "Mixed results on new cancer drug," Nov. 9, 2000 (4 pages).

(56) References Cited

OTHER PUBLICATIONS

Mu et al., "Monoclonal antibody to the gastrin receptor on parietal cells recognizes a 78-kDa protein," PNAS. vol. 84 pp. 2698-2702 (1987).
Mulholland et al., "Elevated Gastric Acid Secretion in Patients with Barrett's Metaplastic Epithelium," Digestive Diseases and Sciences. vol. 34, No. 9 pp. 1329-1334 (1989).
Nadella et al., "Endogenous Gastrin Collaborates With Mutant KRAS in Pancreatic Carcinogenesis." Pancreas, vol. 48, pp. 894-903 (2019).
Nakata et al., "Cloning and Characterization of Gastrin Receptor From ECL Carcinoid Tumor of Mastomys Natalensis," Biochemical and Biophysical Research Communications. vol. 187, No. 2 pp. 1151-1157 (1992).
Narayan et al., "Characterization of gastrin binding to colonic mucosal membranes of guinea pigs," Molecular and Cellular Biochemistry. vol. 112 pp. 163-171 (1992).
National Institutes of Health Publication No. 99-4546, "Barrett's Esophagus," National Digestive Diseases Information Clearinghouse. pp. 1-3 (May 1999).
NCBI Accession No. NP 795344.
Neesse, "Emerging concepts in pancreatic cancer medicine: targeting the tumor stroma." Onco. Targets Ther., vol. 7, pp. 33-43 (2014).
Negre et al., "Autocrine Stimulation of AR4-2J Rat Pancreatic Tumor Cell Growth by Glycine- Extended Gastrin," Int. J. Cancer. vol. 66, No. 5 pp. 653-658 (1996).
Nemeth et al., "Development of a sequence-specific radioimmunoassay by using N-terminal gastrin 1-13 antibody," Chemical Abstracts. vol. 98 p. 495 (1983) [Abstract # 98:51653w].
Nemeth et al., "Identification of progastrin derived peptides in colorectal carcinoma extracts," Gut. vol. 34 pp. 90-95 (1993).
Nemeth et al., "A Gasztrin Aminoterminalis 1-13 Fragmensével Kidolgozott,Szekvenciaspecifikus Radioimmunoassay," Izotoptechnika. vol. 25, No. 4 pp. 288-294 (1982) [Abstract].
Non Opposition Notice corresponding to European Patent Application No. 97905858.3-2401 dated Feb. 17, 2012.
Notice of Acceptance corresponding to Australian Patent Application No. 2005228897 dated Nov. 25, 2009.
Notice of Acceptance corresponding to Australian Patent Application No. 2004225437 dated Apr. 29, 2010.
Notice of Acceptance corresponding to Australian Patent Application No. 2005286164 dated May 15, 2012.
Notice of Allowance corresponding to Canadian Patent Application No. 2,520,010 dated Nov. 22, 2011.
Notice of Allowance corresponding to Canadian Patent Application No. 2,561,405 dated May 8, 2013.
Notice of Allowance corresponding to Canadian Patent Application No. 2,580,965 dated Aug. 1, 2013.
Notice of Allowance corresponding to Canadian Patent Application No. 2,507,637 dated Nov. 18, 2014.
Notice of Allowance corresponding to Japanese Patent Application No. 2006-509465 dated Jan. 18, 2011.
Notice of Allowance corresponding to Israeli Patent Application No. 182012 dated Jul. 16, 2013. [Translation].
Notice of Allowance corresponding to U.S. Appl. No. 10/813,336 dated Feb. 7, 2007.
Notice of Allowance corresponding to U.S. Appl. No. 10/813,336 dated May 15, 2006.
Notice of Allowance corresponding to U.S. Appl. No. 10/813,336 dated Oct. 3, 2006.
Notice of Allowance corresponding to U.S. Appl. No. 11/663,126 dated Jan. 6, 2012.
Notice of Allowance corresponding to U.S. Appl. No. 11/800,889 dated Feb. 7, 2011.
Notice of Allowance corresponding to U.S. Appl. No. 12/693,127 dated Aug. 31, 2012.
Notice of Allowance corresponding to U.S. Appl. No. 12/221,956 dated Oct. 23, 2012.
Notice of Allowance corresponding to U.S. Appl. No. 13/407,321 dated Apr. 2, 2014.
Notice of Allowance corresponding to U.S. Appl. No. 16/622,841 dated Jul. 28, 2022.
Notice of Allowability corresponding to U.S. Appl. No. 16/622,841 dated Dec. 7, 2022.
Notice of Allowability corresponding to U.S. Appl. No. 16/622,841 dated Jan. 10, 2023.
Notice of Grant correspond to Chinese Patent Application No. 200580017341.9 dated Jun. 14, 2016.
Notice of Preliminary Rejection corresponding to Korean Patent Application No. 10-2007-7009115 dated Mar. 30, 2012. [Translation].
Notice of Reasons for Rejection corresponding to Japanese Patent Application No. 2011-222017 dated May 21, 2013. [Translation].
Notice of Publication of Application Corresponding to International Application No. PCT/US2022/012294 dated Jul. 21, 2022.
Notification of European publication number and Information on the application of Article 67(3) EPC corresponding to European Patent Application No. 12176933.5-1412 / 2567974 dated Feb. 13, 2013.
Notification of European publication number and Information on the application of Article 67(3) EPC corresponding to European Patent Application No. 18816949.4-1111 / 3624841 dated Feb. 26, 2020.
Notification of Reexamination corresponding to Chinese Patent Application No. 200580017341.9 dated Mar. 3, 2014.
Nowak et al., "Gemcitabine Exerts a Selective Effect on the Humoral Immune Response: Implications for Combination Chemoimmunotherapy," Cancer Research. vol. 62 pp. 2353-2358 (2002).
Nowak et al., "Synergy between Chemotherapy and Immunotherapy in the Treatment of Established Murine Solid Tumors," Cancer Research. vol. 63 pp. 4490-4496 (2003).
Nywening et al., "Targeting tumor-associated macrophages with CCR2 inhibition in combination with FOLFIRINOX in patients with borderline resectable and locally advanced pancreatic cancer: a single-centre, open-label, dose-finding, non-randomised, phase 1b trial." Lancet. Oncol., vol. 17, pp. 651-662 (2016).
Ochiai et al., "Growth-Promoting Effect of Gastrin on Human Gastric Carcinoma Cell Line TMK-1," Japan Journal of Cancer Research. vol. 76 pp. 1064-1071 (1985).
Office Action corresponding to Australian Patent Application No. 2004225437 dated Dec. 15, 2009.
Office Action corresponding to Chinese Patent Application No. 201880053162.9 dated Dec. 27, 2023.
Office Action corresponding to U.S. Appl. No. 14/500,651 dated Jul. 7, 2016.
Office Action corresponding to Australian Patent Application No. 199940798 dated Jul. 13, 2001.
Office Action corresponding to Australian Patent Application No. 199940798 dated Jul. 24, 2003.
Office Action corresponding to Australian Patent Application No. 2005286164 dated Feb. 14, 2011.
Office Action corresponding to Australian Patent Application No. 2005286164 dated Oct. 4, 2011.
Office Action corresponding to Canadian Patent Application No. 2,520,010 dated Aug. 17, 2009.
Office Action corresponding to Canadian Patent Application No. 2,561,405 dated Dec. 5, 2012.
Office Action corresponding to Canadian Patent Application No. 2,580,965 dated Sep. 30, 2010.
Office Action corresponding to Canadian Patent Application No. 2,580,965 dated Feb. 27, 2012.
Office Action corresponding to Canadian Patent Application No. 2,580,965 dated Oct. 19, 2012.
Office Action corresponding to Canadian Patent Application No. 2,561,405 dated Jul. 31, 2009.
Office Action corresponding to Canadian Patent Application No. 2,561,405 dated Nov. 3, 2010.
Office Action corresponding to Canadian Patent Application No. 2,450,898 dated May 28, 2010.
Office Action corresponding to Canadian Patent Application No. 2,520,010 dated Nov. 1, 2010.
Office Action corresponding to Canadian Patent Application No. 2,507,637 dated Jun. 25, 2013.

(56) References Cited

OTHER PUBLICATIONS

Office Action corresponding to Canadian Patent Application No. 2,507,637 dated Mar. 27, 2014.
Office Action corresponding to Chinese Patent Application No. 200580017341.9 dated Jun. 19, 2009. [Translation].
Office Action corresponding to Chinese Patent Application No. 200580017341.9 dated Dec. 7, 2011. [Translation].
Office Action corresponding to Chinese Patent Application No. 200580017341.9 dated Jul. 3, 2012. [Translation].
Office Action corresponding to Chinese Patent Application No. 200580036710.9 dated Feb. 24, 2011. [Translation].
Office Action corresponding to Chinese Patent Application No. 200580036710.9 dated Apr. 16, 2012. [Translation].
Office Action corresponding to European Patent Application No. 99 924 252.2-2107 dated Jul. 4, 2003.
Office Action corresponding to European Patent Application No. 99 924 252.2-2107 dated Mar. 31, 2004.
Office Action corresponding to European Patent Application No. 02 721 529.2-2107 dated Sep. 23, 2004.
Office Action corresponding to European Patent Application No. 05 784 499.5-2406 dated Jul. 8, 2010.
Office Action corresponding to European Patent Application No. 05 730 336.4-1222 dated Apr. 27, 2007.
Office Action corresponding to European Patent Application No. 04 758 568.2-2404 dated Jul. 17, 2007.
Office Action corresponding to European Patent Application No. 12 176 933.5-1412 dated Jan. 29, 2014.
Office Action corresponding to Indian Patent Application No. 2441/CHENP/2005 dated Jul. 24, 2007.
Office Action corresponding to Indian Patent Application No. 6318/DELNP/2006/707 dated Jul. 5, 2010.
Office Action corresponding to Indonesian Patent Application No. WO 00 2007 00931 dated Oct. 5, 2011. [Translation].
Office Action corresponding to Israeli Patent Application No. 182012 dated Dec. 31, 2009. [Translation].
Office Action corresponding to Israeli Patent Application No. 182012 dated Jul. 12, 2011. [Translation].
Office Action corresponding to Israeli Patent Application No. 182012 dated Dec. 30, 2012. [Translation].
Office Action corresponding to Japanese Patent Application No. 2006-509465 dated Oct. 21, 2009. [Translation].
Office Action corresponding to Japanese Patent Application No. 2006-509465 dated Aug. 26, 2010. [Translation].
Office Action corresponding to Japanese Patent Application No. 2007-506474 dated Jun. 1, 2010. [Translation].
Office Action corresponding to Japanese Patent Application No. 2007-506474 dated Jun. 7, 2011. [Translation].
Office Action corresponding to Japanese Patent Application No. 2006-310647 dated May 29, 2012. [Translation].
Office Action corresponding to Japanese Patent Application No. 2011-034753 dated May 29, 2012. [Translation].
Office Action corresponding to Japanese Patent Application No. Hei10-549578 dated May 9, 2006. [Translation].
Office Action corresponding to Japanese Patent Application No. 2011-222017 dated Jan. 7, 2014. [Translation].
Office Action corresponding to Korean Patent Application No. 10-2007-7009115 dated Feb. 18, 2013. [Translation].
Office Action corresponding to U.S. Appl. No. 08/465,917 dated Aug. 12, 1996.
Office Action corresponding to U.S. Appl. No. 10/762,226 dated Dec. 27, 2006.
Office Action corresponding to U.S. Appl. No. 08/285,984 dated Feb. 7, 1995.
Office Action corresponding to U.S. Appl. No. 11/093,724 dated Feb. 6, 2006.
Office Action corresponding to U.S. Appl. No. 08/219,773 dated Oct. 19, 1994.
Office Action corresponding to U.S. Appl. No. 09/700,329 dated Dec. 17, 2001.
Office Action corresponding to U.S. Appl. No. 09/700,329 dated Apr. 3, 2003.
Office Action corresponding to U.S. Appl. No. 09/700,402 dated Mar. 27, 2007.
Office Action corresponding to U.S. Appl. No. 09/700,402 dated Oct. 25, 2007.
Office Action corresponding to U.S. Appl. No. 11/663,126 dated Jun. 2, 2010.
Office Action corresponding to U.S. Appl. No. 11/663,126 dated Jul. 15, 2011.
Office Action corresponding to U.S. Appl. No. 10/813,336 dated Oct. 20, 2005.
Office Action corresponding to U.S. Appl. No. 10/192,257 dated Sep. 21, 2005.
Office Action corresponding to U.S. Appl. No. 10/104,607 dated Mar. 29, 2005.
Office Action corresponding to U.S. Appl. No. 10/104,607 dated Nov. 21, 2005.
Office Action corresponding to U.S. Appl. No. 10/813,336 dated Jun. 23, 2005.
Office Action corresponding to U.S. Appl. No. 10/829,137 dated Oct. 15, 2007.
Office Action corresponding to U.S. Appl. No. 10/323,692 dated Aug. 10, 2005.
Office Action corresponding to U.S. Appl. No. 10/235,236 dated Aug. 10, 2005.
Office Action corresponding to U.S. Appl. No. 11/093,724 dated Nov. 25, 2005.
Office Action corresponding to U.S. Appl. No. 11/252,904 dated Jan. 8, 2009.
Office Action corresponding to U.S. Appl. No. 11/252,904 dated Oct. 26, 2009.
Office Action corresponding to U.S. Appl. No. 11/252,904 dated Jul. 20, 2010.
Office Action corresponding to U.S. Appl. No. 11/663,126 dated Jun. 22, 2009.
Office Action corresponding to U.S. Appl. No. 11/663,126 dated Nov. 25, 2009.
Office Action corresponding to U.S. Appl. No. 11/800,889 dated Oct. 2, 2009.
Office Action corresponding to U.S. Appl. No. 11/499,261 dated Mar. 15, 2007.
Office Action corresponding to U.S. Appl. No. 11/499,261 dated Nov. 30, 2007.
Office Action corresponding to U.S. Appl. No. 11/499,261 dated Sep. 24, 2008.
Office Action corresponding to U.S. Appl. No. 11/499,261 dated May 14, 2009.
Office Action corresponding to U.S. Appl. No. 11/499,261 dated Nov. 15, 2010.
Office Action corresponding to U.S. Appl. No. 11/499,261 dated Apr. 26, 2011.
Office Action corresponding to U.S. Appl. No. 11/499,261 dated Aug. 27, 2013.
Office Action corresponding to U.S. Appl. No. 11/499,261 dated Mar. 7, 2014.
Office Action corresponding to U.S. Appl. No. 11/800,889 dated Feb. 18, 2010.
Office Action corresponding to U.S. Appl. No. 11/800,889 dated Jun. 23, 2010.
Office Action corresponding to U.S. Appl. No. 12/221,956 dated May 28, 2010.
Office Action corresponding to U.S. Appl. No. 12/221,956 dated Feb. 16, 2011.
Office Action corresponding to U.S. Appl. No. 12/221,956 dated Oct. 4, 2011.
Office Action corresponding to U.S. Appl. No. 12/221,956 dated Jun. 26, 2012.
Office Action corresponding to U.S. Appl. No. 12/693,127 dated Feb. 11, 2011.
Office Action corresponding to U.S. Appl. No. 12/693,127 dated Jul. 16, 2010.

(56) References Cited

OTHER PUBLICATIONS

Office Action corresponding to U.S. Appl. No. 12/693,127 dated Feb. 21, 2012.
Office Action corresponding to U.S. Appl. No. 13/012,433 dated Jul. 20, 2011.
Office Action corresponding to U.S. Appl. No. 13/012,433 dated Feb. 17, 2012.
Office Action corresponding to U.S. Appl. No. 13/012,433 dated Sep. 25, 2012.
Office Action corresponding to U.S. Appl. No. 13/407,321 dated Mar. 20, 2013.
Office Action corresponding to U.S. Appl. No. 13/407,321 dated Jul. 25, 2013.
Office Action and Notice to Comply corresponding to U.S. Appl. No. 14/500,651 dated Feb. 1, 2017.
Office Action corresponding to U.S. Appl. No. 14/500,651 dated Oct. 4, 2017.
Office Action corresponding to Israeli Patent Application No. 271427 dated Oct. 11, 2020. [Translation].
Office Action (Restriction Requirement) corresponding to U.S. Appl. No. 16/622,841 dated Jul. 19, 2021.
Office Action corresponding to U.S. Appl. No. 16/622,841 dated Oct. 6, 2021.
Office Action corresponding to Japanese Patent Application No. 2020-519008 dated Apr. 4, 2022.
Office Action corresponding to Indian Patent Application No. 201927053759 dated Sep. 21, 2022.
Office Action corresponding to Israeli Patent Application No. 271427 dated Oct. 27, 2022.
Office Action corresponding to Japanese Patent Application No. 2020-519008 dated Jan. 4, 2023.
Office Action corresponding to Canadian Application No. 3,066,756 dated Aug. 23, 2023.
Office Action corresponding to Korean Application No. 10-2020-7001421 dated May 3, 2023.
Office Action corresponding to Australian Application No. 2018283284 dated May 5, 2023.
Office Action and Search Report corresponding to Chinese Application No. 201880053162.8 dated Feb. 18, 2023.
Office Action corresponding to U.S. Appl. No. 17/148,159 dated Oct. 2, 2023.
Office Action corresponding to Japanese Application No. 2020-519008 dated Aug. 22, 2023.
Ohkura et al., "Gastrin-Enhanced Tumor Growth of a Xenotransplantable Human Gastric Carcinoma in Nude Mice," Jpn. J. Clin. Oncol. vol. 10, No. 2 pp. 255-263 (1980).
Ohning et al., "Differential Kinetics for Immunoneutralization of Circulating Gastrin by Gastrin Monoclonal Antibody and Its Fab1 Fragment in Rats," Peptides. vol. 15 pp. 417-423 (1994).
Ohning et al., "Gastrin mediates the gastric mucosal proliferative response to feeding," American Journal of Physiology. Vol. 271 (Gastrointest. Liver Physiol. 34) pp. G470-G476 (1996).
Ohsawa et al., "Effects of Three H2-Receptor Antagonists (Cimetidine, Famotidine, Ranitidine) On Serum Gastrin Level," International Journal of Clinical Pharmacology Research. vol. 22, No. 2 pp. 29-35 (2002).
Ohtsu et al., "Randomized Phase III Trial of Fluorouracil Alone Versus Fluorouracil Plus Cisplatin Versus Uracil and Tegafur Plus Mitomycin in Patients With Unresectable, Advanced Gastric Cancer: The Japan Clinical Oncology Group Study (JCOG9205)," Journal of Clinical Investigation. vol. 21, No. 1 pp. 54-59 (2003).
Okada et al., "Evaluation of cholecystokinin, gastrin, CCK-A receptor, and CCK-B/gastrin receptor gene expressions in gastrin cancer," Cancer Letters. vol. 106, No. 2 pp. 257-262 (1996).
Onorato et al., "Immunohistochemical and ELISA Assays for Biomarkers of Oxidative Stress in Aging and Disease," Annals of New York Academy of Sciences. vol. 854 pp. 277-290 (1998).

O'Reilly et al., "Durvalumab With or Without Tremelimumab for Patients With Metastatic Pancreatic Ductal Adenocarcinoma. A Phase 2 Randomized Clinical Trial." JAMA Oncol., vol. 5(10), pp. 1431-1438 (2019).
Osband, M.E., and Ross, S., "Problems in the investigational study and clinical use of cancer immunotherapy," Immunology Today. vol. 1, No. 6 pp. 193-195 (1990).
Osborne et al. (2019) "Gastrin vaccine improves response to immune checkpoint antibody in murine pancreatic cancer by altering the tumor microenvironment," Cancer Immunology, Immunotherapy, Springer, Berlin/Heidelberg, vol. 68, No. 10, pp. 1635-1648.
Osborne et al. (2019) "The Physiology of Immune Therapies and Their Application in Treating Gastrointestinal Cancers: Vaccine against gastrin, a polyclonal antibody stimulator, decreases pancreatic cancer metastases," Am J Physiol Gastrointest Liver Physiol, vol. 317, pp. 682-693.
Osin, P.P., and Lakhani, S.R., "The pathology of familial breast cancer: Immunohistochemistry and molecular analysis," Breast Cancer Research. vol. 1, No. 1 pp. 36-40 (1999).
Pack et al., "Miniantibodies: use of amphipathic helixes to produce functional, flexibly linked dimeric FV fragments with high avidity in *Escherichia coli*." Biochemistry, vol. 31, pp. 1579-1584 (1992).
Palnæs Hansen et al., "Metabolism and Influence of Glycine-Extended Gastrin on Gastric Acid Secretion in Man," Digestion. vol. 57 pp. 22-29 (1996).
Pannequin et al., "Divergent roles for ferric ions in the biological activity of amidated and non- amidated gastrins," Journal of Endocrinology. vol. 181, No. 2 pp. 315-325 (2004).
Pannequin et al. "Ferric Ions Are Essential for the Biological Activity of the Hormone Glycine-extended Gastrin", Journal of Biological Chemistry, vol. 277, No. 50, Issue of Dec. 13, pp. 48602-48609, 2002.
Pardoll, "The blockade of immune checkpoints in cancer immunotherapy." Nat. Rev. Cancer, vol. 12, pp. 252-264 (2012).
Parsonnet et al., "Helicobacter Pylori Infection and the Risk of Gastric Carcinoma," The New England Journal of Medicine. vol. 325, No. 16 pp. 1127-1131 (1991).
Pathak (2005) Immunology: Essential and Fundamental. Science Publishers Enfield, N.H. Chapter 4:66-86.
Pauwels et al., "Identification of Progastrin in Gastrinomas, Antrum, and Duodenum by a Novel Radioimmunoassay," The Journal of Clinical Investigation. vol. 77 pp. 376-381 (1986).
Pawlikowski et al., "Gastrin and Somatostatin Levels in Patients with Gastric Cancer," Horm. Metabol. Res. vol. 21 pp. 89-91 (1989).
Petrioli et al., "Treatment of Advanced Colorectal Cancer with High-dose Intensity Folinic Acid and 5-Fluorouracil Plus Supportive Care," European Journal of Cancer. vol. 31A, No. 12 pp. 2105-2108 (1995).
Petrelli et al., "The Modulation of Fluorouracil With Leucovorin in Metastatic Colorectal Carcinoma: A Prospective Randomized Phase III Trial," Journal of Clinical Oncology. vol. 7 pp. 1419-1426 (1989).
Plested et al. "ELISA," Methods in Molecular Medicine. vol. 71 pp. 243-261 (2003).
Podlecki et al., "Nuclear Translocation of the Insulin Receptor: A Possible Mediator of Insulin's Long Term Effects," The Journal of Biological Chemistry. vol. 262, No. 7 pp. 3362-3368 (1987).
Power et al., "A novel gastrin-processing pathway in mammalian antrum," Chemical Abstracts. vol. 109, No. 9 p. 113 (1988) [Abstract # 109:67341z].
Preliminary Report corresponding to Japanese Patent Application No. 2007-506474 dated Feb. 9, 2012. [Translation].
Rae-Venter et al., "Gastrin Receptors in Human Colon Carcinoma," Gastroenterology. vol. 80, No. 5, Part 2 p. 1256 (1981) [Abstract].
Rahier et al., "Biosynthesis of Gastrin: Localization of the Precursor and Peptide Products Using Electron Microscopic-Immunogold Methods," Gastroenterology. vol. 92 pp. 1146-1152 (1987) [Abstract].
Rai et al., "Cholecystokinin and gastrin receptors targeting in gastrointestinal cancer." Surg. Oncol., vol. 21, pp. 281-292 (2012).

(56) References Cited

OTHER PUBLICATIONS

Reddy, "Small Cell Lung Cancer: Improving Outcomes," American Society for Therapeutic Radiology and Oncology, 42nd Annual Meeting, Day 1, Oct. 22, 2000, meeting report published by Medscape.
Redmond, E.J., and Wetscher, G.J., "Gastroesophageal Reflux Disease," Ronald Hinder ed., R.G. Landes Company. pp. 1-6 (1993).
Rehfeld, "The New Biology of Gastrointestinal Hormones," Physiological Reviews. vol. 78, No. 4 pp. 1087-1108 (1998).
Rehfeld et al., "Gastrin in Human Bronchogenic Carcinomas: Constant Expression but Variable Processing of Progastrin," Cancer Research. vol. 49 pp. 2840-2843 (1989).
Rehfeld et al., "Production and Evaluation of Antibodies for the Radioimmunoassay of Gastrin," Scnad. J. Clin. Lab. Invest. vol. 30 pp. 221-232 (1972).
Rehfeld et al., "Cell-specific processing of pro-cholecystokinin and pro-gastrin," Biochimie. vol. 70 pp. 25-31 (1988).
Rehfeld, J.F., and Johnsen, A.H., "Residue-specific immunochemical sequence prediction," Journal of Immunological Methods. vol. 171 pp. 139-142 (1994).
Rehfeld et al., "Sulfation of Gastrin: Effect on Immunoreactivity," Regulatory Peptides. vol. 2 pp. 333-342 (1981).
Rehfeld, J.F., "Gastrin and Colorectal Cancer: A Never-Ending Dispute?" Gastroenterology. vol. 108, No. 4 pp. 1307-1310 (1995).
Rehfeld, J.F., "Three Components of Gastrin in Human Serum," Biochimica et Biophysica Acta. vol. 285 pp. 364-372 (1972).
Restriction Requirement corresponding to U.S. Appl. No. 14/500,651 dated Mar. 11, 2016.
Ritter et al., "Serological Analysis of Human Anti-Human Antibody Responses in Colon Cancer Patients Treated with Repeated Doses of Humanized Monoclonal Antibody A33," Cancer Research. vol. 61 pp. 6851-6859 (2001).
Robertson et al., "Effect of Gastrointestinal Hormones and Synthetic Analogues on the Growth of Pancreatic Cancer," International Journal of Cancer. vol. 63 pp. 69-75 (1995).
Rodriguez-Lescure et al., "Phase II Study of Gemcitabine (GEM) and Weekly 48-Hour Continuous Infusion (CI) with High Dose 5-Fluorouracil (5-FU) in Advanced Exocrine Pancreatic Cancer (APC)," Proceedings of the Annual Meeting of the American Society of Clinical Oncology. vol. 18, p. 298 (1999) [Abstract # 1145].
Romani et al. "Gastrin Receptor Antagonist CI-988 Inhibits Growth of Human Colon Cancer In Vivo and In Vitro," Aust. N.Z. J. Surgery. vol. 66 pp. 235-237 (1996).
Romani et al., "Potent new family of gastrin receptor antagonists (GRAs) produces in vitro and in vivo inhibition of human colorectal cancer (CRC) cell lines," Proceedings of the American Association for Cancer Research. vol. 35 p. 397 (1994) [Abstract # 2369].
Rondeel, "Immunofluorescence versus ELISA for the detection of antinuclear antigens," Expert Rev. Mol. Diagn. vol. 2, No. 3 pp. 226-232 (2002).
Rothenberg et al., "A phase II trial of gemcitabine in patients with 5-FU-refractory pancreas cancer," Annals of Oncology. vol. 7 pp. 347-353 (1996).
Royal et al. "Phase 2 Trial of Single Agent Ipilimumab (Anti-CTLA-4) for Locally Advanced or Metastatic Pancreatic Adenocarcinoma," Author Manuscript, 15 pages, Published in final edited form as: J Immunother. 33(8), pp. 828-833 (2010).
Saillan-Barreau et al., "Evidence for a functional role of the cholecystokinin-B/gastrin receptor in the human fetal and adult pancreas." Diabetes, vol. 48, pp. 2015-2021 (1999).
Scemama et al., "Characterisation of gastrin receptors on a rat pancreatic acinar cell line (AR42J). A possible model for studying gastrin mediated cell growth and proliferation," Gut. vol. 28, No. S1 pp. 233-236 (1987).
Scheele et al., "Indicators of prognosis after hepatic resection for colorectal secondaries," Surgery. vol. 110, No. 1 pp. 13-29 (1991).
Scheithauer et al., "Combined Intraperitoneal plus Intravenous Chemotherapy after Curative Resection for Colonic Adenocarcinome," European Journal of Cancer. vol. 31A, No. 12 pp. 1981-1986 (1995).
Schlom, "Monoclonal Antibodies: They're More and Less Than You Think," Molecular Foundations of Oncology. ed. Broder Williams & Williams, Baltimore MD, pp. 95-134 (1991).
Schmitz et al., "CCK-B/gastrin receptors in human colorectal cancer," European Journal of Clinical Investigation. vol. 31 pp. 812-820 (2001).
Seitz et al., "Elevated Serum Gastrin Levels in Patients with Colorectal Neoplasia," J. Clin. Gastroenterol. vol. 13, No. 5 pp. 541-545 (1991).
Senior, "Immunization blocks gastrin's ability to promote tumour cell division," Drug Discovery Today. vol. 6, No. 2 pp. 62-63 (2001).
Seva et al., "Characterization of the Glycine-Extended Gastrin (G-GLY) Receptor on AR4-2J Cells," Gastroenterology. vol. 108 p. A1005 (1995) [Abstract].
Seva et al., "Growth-Promoting Effects of Glycine-Extended Progastrin", Science. vol. 265, No. 5170 pp. 410-412 (1994).
Seva et al., "Lorglumide and Loxglumide Inhibit Gastrin-stimulated DNA Synthesis in a Rat Tumoral Acinar Pancreatic Cell Line (AR42J)," Cancer Research. vol. 50, No. 8 pp. 5829-5833 (1990).
Shewach, D.S., and Lawrence, T.S., "Radiosensitization of Human Solid Tumor Cell Lines With Gemcitabine," Seminars in Oncology. vol. 23, No. 5, Suppl. 10 pp. 65-71 (1996).
Shewach et al., "Metabolism of 2',2'-Difluoro-2'-Deoxycytidine and Radiation Sensitization of Human Colon Carcinoma Cells," Cancer Research. vol. 54 pp. 3218-3223 (1994).
Siddheshwar et al: "Plasma levels of progastrin but not amidated gastrin or glycine extended gastrin are elevated in patients with colorectal carcinoma", Gut. vol. 48, No. 1, London, UK, pp. 47-52 (2001).
Siemann, "Satisfactory and Unsatisfactory Tumor Models: Factors Influencing the Selection of a Tumor Model for Experimental Evaluation," Rodent Tumor Models in Experimental Cancer Therapy (Ed. Kallman) Pergamon Press, NY. pp. 12-15 (1987).
Singh et al., "High Levels of Progastrin Significantly Increase Premalignant Changes in Colonic Mucosa of Mice in Tesponse to the Chemical Carcinogen, AOM," Gastroenterology. vol. 114, No. 4 p. A680 (1998) [Abstract # G2810].
Singh et al., "Incomplete processing of progastrin expressed by human colon cancer cells: roles of noncarboxyamidated gastrins," The American Physiological Society. pp. G459-G468 (1994).
Singh et al., "Novel Gastrin Receptors Mediate Mitogenic Effects of Gastrin and Processing Intermediates of Gastrin on Swiss 3T3 Fibroblasts. Absence of Detectable Cholecystokinin (CCK)-A and CCK-B Receptors," The Journal of Biological Chemistry. vol. 270, No. 15 pp. 8429-8438 (1995).
Singh et al., "Role of Gastrin and Gastrin Receptors on the Growth of a Transplantable Mouse Colon Carcinoma (MC-26) in BALB/c Mice," Cancer Research. vol. 46 pp. 1612-1616 (1986).
Singh et al., "Gut hormones in colon cancer: past and prospective studies," Cancer Journal. vol. 3, No. 1 pp. 28-33 (1990).
Sipponen et al., "Serum Levels of Amidated Gastrin-17 and Pepsinogen 1 in Atrophic Gastritis: An Observational Case-Control Study," Scandinavian Journal of Gastroenterology. vol. 37, No. 7 pp. 785-791 (2002).
Slooter et al., "Tumor growth stimulation after partial hepatectomy can be reduced by treatment with tumor necrosis factor (," British Journal of Surgery. vol. 82 pp. 129-132 (1995).
Smith, A.M., and Watson, S.A., "Gastrin and gastrin receptor activation: an early event in the adenoma-carcinoma sequence," Gut. vol. 47, No. 6 pp. 820-824 (2000).
Smith, A.M., and Watson, S.A., "Review Article: Gastrin and Colorectal Cancer," Alimentary Pharmacology & Therapeutics. vol. 14, No. 10 pp. 1231-1247 (2000).
Smith et al., "Characterization of the CCK-C (cancer) receptor in human pancreatic cancer," International Journal of Molecular Medicine. vol. 10, No. 6 pp. 689-694 (2002).

(56) References Cited

OTHER PUBLICATIONS

Smith et al., "Elevated Gastrin Levels in Patients with Colon Cancer or Adenomatous Polyps," Digestive Diseases and Science. vol. 34, No. 2 pp. 171-174 (1989).
Smith et al., "Phase I/II Study of G17-DT, an Anti-Gastrin Immunogen, in Advanced Colorectal Cancer," Clinical Cancer Research. vol. 6, No. 12 pp. 4719-4724 (2000).
Smith et al. "Gastrin regulates growth of human pancreatic cancer in a tonic and autocrine fashion," American Journal of Physiology. vol. 270, No. 39 (Regulatory Integrative Comp. Physiol. 39) pp. R1078-R1084 (1996).
Smith et al., "Identification and characterization of CCK-B/gastrin receptors in human pancreatic cancer cell lines," American Journal of Physiology. vol. 266 pp. R277-R283 (1994).
Smith et al. "Identification of gastrin as a growth peptide in human pancreatic cancer," American Journal of Physiology. vol. 268 (Regulatory Integrative Comp. Physiol. 37) pp. R135-R141 (1995).
Smith, J.P., and Solomon, T.E., "Effects of Gastrin, Proglumide, and Somatostatin on Growth of Human Colon Cancer," Gastroenterology. vol. 95, No. 6 pp. 1541-1548 (1988).
Smith et al., "Sensitivity of the Esophageal Mucosa to pH in Gastroesophageal Reflux Disease," Gastroenterology. vol. 96 pp. 683-689 (1989).
Smith et al., "Gastric carcinoid expresses the gastrin autocrine pathway," British Journal of Surgery. vol. 85 pp. 1285-1289 (1998).
Smith et al., "Gastrin may have an autocrine/paracrine role in Barrett's oesophagus and oesophageal adenocarcinoma," British Journal of Surgery. vol. 84 pp. 706-707 (1996).
Smith et al., "Antisense oligonucleotides to gastrin inhibit growth of human pancreatic cancer," Cancer Letters. vol. 135 pp. 107-112 (1999).
Smith & Solomon, "Cholecystokinin and pancreatic cancer: the chicken or the egg?" Am. J. Physiol. Gastrointest. Liver Physiol., vol. 306, pp. G91-G101 (2014).
Smith et al., "Gastrin and gastric cancer." Cellular and Molecular Gastroenterology and Hepatology, vol. 4(1), pp. 75-83 (2017).
Smith et al., "Cholecystokinin stimulates growth of human pancreatic adenocarcinoma SW-1990." Dig. Dis. Sci., vol. 35, pp. 1377-1384 (1990).
Smith et al., "CCK stimulates growth of six human pancreatic cancer cell lines in serum-free medium." Regul. Pept., vol. 32, pp. 341-349 (1991).
Smith et al., "Characterization of CCK-B/gastrin-like receptors in human colon cancer." Am. J. Physiol., vol. 271, pp. R797-R805 (1996).
Smith et al., "Quantitative analysis of gastrin mRNA and peptide in normal and cancerous human pancreas." Int. J. Mol. Med., vol. 2, pp. 309-315 (1998).
Smith et al., "Characterization of CCK-B/gastrin-like receptors in human gastric carcinoma." Int. J. Oncol., vol. 12, pp. 411-419 (1998).
Smith et al., "Functional significance of gastrin gene expression in human cancer cells." Regul. Pept. vol. 117, pp. 167-173 (2004).
Smith et al., "Cholecystokinin receptor antagonist halts progression of pancreatic cancer precursor lesions and fibrosis in mice." Pancreas, vol. 43, pp. 1050-1059 (2014).
Smith et al., "Cholecystokinin receptor antagonist alters pancreatic cancer microenvironment and increases efficacy of immune checkpoint antibody therapy in mice." Cancer Immunol. Immunoth., vol. 67, pp. 195-207 (2018).
Sobhani et al., "Chronic Endogenous Hypergastrinemia in Humans: Evidence for a Mitogenic Effect on the Colonic Mucosa," Gastroenterology. vol. 105, No. 1 pp. 22-30 (1993).
Sobhani et al., "Immunohistochemical characterization of gastrinomas with antibodies specific to different fragments of progastrin," Gastroentérologie Clinique et Biologique. Vol. 13, No. 11 pp. 865-872 (1989).
Soll et al. "Gastrin-Receptors on Isolated Canine Parietal Cells," The Journal of Clinical Investigation, Inc.. vol. 73 pp. 1434-1447 (1984).

Song et al., "The human gastrin/cholecystokinin type B receptor-gene: Alternative splice donor site in exon 4 generates two variant mRNAs," PNAS. vol. 90, No. 19 pp. 9085-9089 (1993).
Spitler, L.E. "Cancer Vaccines: The Interferon Analogy," Cancer Biotherapy. vol. 10, No. 1 pp. 1-3 (1995).
Stepan et al., "Glycine-Extended Gastrin Exerts Growth-Promoting Effects on Human Colon Cancer Cells," Molecular Medicine. vol. 5, No. 3 pp. 147-159 (1999).
Stepan et al., "Glycine-Extended Gastrin Exerts Growth-Promoting Effects on Colon Cancer Cell Lines," Gastroenterology. vol. 110, No. 4 p. A1122 (1996) [Abstract].
Stubbs et al., "Correlation between Uptake of Labeled Anti-CCKB/Gastrin Receptor Antibodies and the Occurrence of Apoptosis in Hepatoma Cell Lines," Gastroenterology. vol. 122, No. 4, Suppl. 1 p. A-380 (2002) [Abstract# T915].
Stubbs et al., "Endocytosis of Anti-CCK-B/Gastrin Receptor Antibody and Effect on Hepatoma Cell Lines," The Journal of Histochemistry & Cytochemistry. vol. 50, No. 9 pp. 1213-1217 (2002).
Sugano, et al., "Identification and Characterization of Glycine-extended Post-translational Processing Intermediates of Progastrin in Porcine Stomach," The Journal of Biological Chemistry. vol. 260, No. 21 pp. 11724-11729 (1985).
Sundler et al., "The Neuroendocrine System of the Gut-An Update," Acta Oncologica. vol. 30, No. 4 pp. 419-427 (1991).
Taetle et al., "Effects of combined antigrowth factor receptor treatment on in vitro growth of multiple myeloma," J. Natl. Cancer Inst. vol. 86, No. 6 pp. 450-455 (1994) [Abstract].
Takhar et al., "The role of gastrin in colorectal carcinogenesis," J.R. Coll. Surg. Edinb. Irel. vol. 2, No. 5 pp. 251-257 (2004).
Takinami et al., "YF476 is a new potent and selective gastrin/cholecystokinin-B receptor antagonist in vitro and in vivo," Ailment Pharmacol. Ther. vol. 11, No. 1 pp. 113-120 (1997).
Talley et al., "Risk for Colorectal Adenocarcinoma in Pernicious Anemia," Annals of Internal Medicine. vol. 111, No. 9 pp. 738-742 (1989).
Tang et al., "Expression of receptors for gut peptides in human pancreatic adenocarcinoma and tumor-free pancreas," British Journal of Cancer. vol. 75, No. 10 pp. 1467-1473 (1997).
Taniguchi et al., "Cholecystokinin-B/gastrin receptor signaling pathway involves tyrosine phosphorylations of p125FAK and p42MAP," Oncogene. vol. 9 pp. 861-867 (1994).
Tarasova et al., "Endocytosis of gastrin in cancer cells expressing gastrin/CCK-B receptor," Cell and Tissue Research. vol. 287 pp. 325-330 (1997). [missing pp. 331-333].
Tarasova et al., "Anti-peptide antibodies specific for the gastrin/cholecystokinin-B receptor," Letters in Peptide Science. vol. 1 pp. 221-228 (1994).
Taylor, "Chemotherapy, radiotherapy and immunotherapy of colorectal neoplasia," Current Opinion in Gastroenterology. vol. 9 pp. 28-33 (1993).
Tetin, S.Y., and Stroupe, S.D., "Antibodies in Diagnostic Applications," Current Pharmaceutical Biotechnology. vol. 5, No. 1 pp. 9-16 (2004).
Thorndyke, M., and Dockray, G.J., "Identification and localization of material with gastrin-like immunoreactivity in the neutral ganglion of a photochordate, Ciona intestinalis," Regulatory Peptides. vol. 16 pp. 269-279 (1986).
Tielemans et al., "Proliferation of Enterochromaffinlike Cells in Omeprazole-Treated Hypergastrinemic Rats," Gastroenterology. vol. 96, No. 3 pp. 723-729 (1989).
Todisco et al., "Gastrin and Glycine-extended Progastrin Processing Intermediates Induce Different Programs of Early Gene Activation," The Journal of Biological Chemistry. vol. 270, No. 47 pp. 28337-28341 (1995).
Torosian et al., "Colon Carcinoma Metastatic to the Thigh-An Unusual Site of Metastasis. Report of a Case," Diseases of the Colon and Rectum. vol. 30, No. 10 pp. 805-808 (1987).
Trakal et al., "Diagnosis and Etiology of Barrett's Esophagus: Presence of Gastrin Secreting Cells," Acta Gastroenterológica Latinoamericana. vol. 15, No. 2 pp. 67-80 (1985) [Abstract].

(56) References Cited

OTHER PUBLICATIONS

Tschmelitsch et al., "Enhanced Antitumor Activity of Combination Radioimmunotherapy (131I-labeled Monoclonal Antibody A33) with Chemotherapy (Fluorouracil)," Cancer Research. vol. 57 pp. 2181-2186 (1997).
Tytgat et al., "Five-Year Cimetidine Maintenance Trial for Peptic Ulcer Disease," Scandinavian Journal of Gastroenterology. vol. 25, No. 10 pp. 974-980 (1990).
Ullrich et al. "Signal Transduction by Receptors with Tyrosine Kinase Activity," Cell. vol. 61 pp. 203-212 (1990).
UniProtKB/Swiss-Prot entry P01350, (1986) (accessed on Mar. 26, 2007).
Upp et al., "Clinical Significance of Gastrin Receptors in Human Colon Cancers" Cancer Research. vol. 49 pp. 488-492 (1989).
Upp et al., "Polyamine Levels and Gastrin Receptors in Colon Cancers" Ann. Surg. vol. 207, No. 6 pp. 662-668 (1988).
Väänänen et al. "Non-endoscopic diagnosis of atrophic gastritis with a blood test. Correlation between gastric histology and serum levels of gastrin-17 and pepsinogen I: a multicentre study," European Journal of Gastroenterology & Hepatology. vol. 15, No. 8 pp. 885-891 (2003).
Vaillant et al., "Cellular Origins of Different Forms of Gastrin. The Specific Immunocytochemical Localization of Related Peptides," The Journal of Histochemistry and Cytochemistry. vol. 27, No. 5 pp. 932-935 (1979).
Vaillant et al., "Repeat liver resection for recurrent colorectal metastasis," British J. Surgery. vol. 80, No. 3 pp. 340-344 (1993).
Van Cutsem et al., "Phase III Study of Docetaxel and Cisplatin Plus Fluorouracil Compared With Cisplatin and Fluorouracil As First-Line Therapy for Advanced Gastric Cancer: A Report of the V325 Study Group," Journal of Clinical Oncology. vol. 24, No. 31 pp. 4991-4997- (2006).
Van Solinge et al., "Expression but Incomplete Maturation of Progastrin in Colorectal Carcinomas," Gastroenterology. vol. 104 pp. 1099-1107 (1993).
Vanhoefer et al., "Final Results of a Randomized Phase III Trial of Sequential High-Dose Methotrexate, Fluorouracil, and Doxorubicin Versus Etoposide, Leucovorin, and Fluorouracil Versus Infusional Fluorouracil and Cisplatin in Advanced Gastric Cancer: A Trial of the European Organization for Research and Treatment of Cancer Gastrointestinal Tract Cancer Cooperative Group," Journal of Clinical Oncology. vol. 18, No. 14 pp. 2648-2657 (2000).
Varndell et al., "Intracellular topography of immunoreactive gastrin demonstrated using electron immunocytochemistry," Experienta. vol. 39 pp. 713-717 (1983).
Varro et al., "The human gastrin precursor," Biochem. J. vol. 256 pp. 951-957 (1988).
Varro, A., and Dockray, G.J., "Post-translational processing of progastrin: inhibition of cleavage, phosphorylation and sulphation by brefeldin A," Biochem. J. vol. 295 pp. 813-819 (1993).
Varro et al., "Discrimination between Temperature- and Brefeldin A-sensitive Steps in the Sulfation, Phosphorylation, and Cleavage of Progastrin and Its Derivatives," The Journal of Biological Chemistry. vol. 269, No. 32 pp. 20764-20770 (1994).
Varro et al., "Pathways of Processing of the Gastrin Precursor in Rat Antral Mucosa," Journal of Clinical Investigation. vol. 95 pp. 1642-1649 (1995).
Varro, A., and Ardill, J.E.S., "Gastrin: an analytical review," Ann. Clin. Biochem. vol. 40 pp. 472-480 (2003).
Vauthey et al., "Factors Affecting Long-Term Outcome After Hepatic Resection For Hepatocellular Carcinoma," The American Journal of Surgery. vol. 169 pp. 28-35 (1995).
Von Hoff, D.D., and Bearss, D., "New drugs for patients with pancreatic cancer," Curr. Opin. Oncology. vol. 14 pp. 621-627 (2002).
Waghray et al., "Deciphering the Role of Stroma in Pancreatic Cancer." Curr. Opin. Gastroenterol., vol. 29, pp. 537-543 (2013).
Wang et al., "Processing and Proliferative Effects of Human Progastrin in Transgenic Mice," Journal of Clinical Investigation. vol. 98, No. 8 pp. 1918-1929 (1996).
Wank, "Cholecystokinin receptors," Am. J. Physiol. vol. 269 (Gastrointest. Liver Physiol.) pp. G628-G646 (1995).
Wank et al., "Cholecystokinin Receptor Family. Molecular Cloning, Structure, and Functional Expression in Rat, Guinea Pig, and Human," Annals New York Academy of Sciences. vol. 713 pp. 49-66 (1994).
Wank et al., "Brain and gastrointestinal cholecystokinin receptor family: Structure and functional expression," PNAS. vol. 89 pp. 8691-8695 (1992).
Watson et al., "A comparison of the therapeutic effectiveness of gastrin neutralization in two human gastric cancer models: relation to endocrine and autocrine/paracrine gastrin mediated growth," Gut. vol. 45 pp. 812-817 (1999).
Watson et al., "The In Vitro Growth Response of Primary Human Colorectal and Gastric Cancer Cells to Gastrin," International Journal of Cancer. vol. 43 pp. 692-696 (1989).
Watson et al., "Antibodies Raised by Gastrimmune Inhibit the Spontaneous Metastasis of a Human Colorectal Tumour, AP5LV," European Journal of Cancer. vol. 35, No. 8 pp. 1286-1291 (1999).
Watson et al., "Antiserum raised against an epitope of the cholecystokinin B/gastrin receptor inhibits hepatic invasion of a human colon tumor," Cancer Research. vol. 60, No. 20 pp. 5902-5907 (2000).
Watson et al., "Inhibition of Gastrin-stimulated Growth of Gastrointestinal tumour cells by Octreotide and the Gastrin/Cholecystokinin Receptor Antagonists, Proglumide and Lorglumide," European Journal of Cancer. vol. 28A, No. 8/9 pp. 1462-1467 (1992).
Watson et al., "A Comparison of An Anti-Gastrin Antibody and Cytotoxic Drugs in the Therapy of Human Gastric Ascites in SCID Mice," International Journal of Cancer. vol. 81, No. 2 pp. 248-254 (1999).
Watson et al., "Anti-Gastrin Antibodies Raised by Gastrimmune Inhibit Growth of the Human Colorectal Tumour AP5," International Journal of Cancer. vol. 61, No. 2 pp. 233-240 (1995).
Watson et al., "Effect of Gastrin Neutralization on the Progression of the Adenoma:Carcinoma Sequence in the Min Mouse Model of Familial Adenomatous Polyposis," Gastroenterology. vol. 114, No. 4, Pt. 2 p. A701 (1998) [Abstract # G2900].
Watson et al., "Enhanced Inhibition of Pancreatic Cancer by Combination of the G17DT Immunogen and Gemcitabine," Amer. Soc. Clin. Oncol. vol. 37 (2002) [Abstract] (2 pages).
Watson, "Gastrin antagonists and gastrointestinal tumours," Expert Opinion on Investigational Drugs. vol. 4, No. 12 pp. 1253-1266 (1995).
Watson et al., "Antibodies targeting the Amino Terminal portion of the Human CCKB/gastrin receptor inhibit the liver invasion of a human colonic tumour," Research Presentation, Digestive Disease Week, American Gastroenterological Association (1998), 17 slides.
Watson et al., "Gastrin Inhibition Increases the Potency of Cytotoxic Agents in Pancreatic Cancer," Gastroenterology. vol. 122, No. 4 p. A-241 (2002) [Abstract # M952].
Watson et al., "The Effect of the E2 Prostaglandin Enprostil, and the Somatostatin Analogue SMS 201 995, on the Growth of a Human Gastric Cell Line, MKN45G," International Journal of Cancer. vol. 45 pp. 90-94 (1990).
Watson et al., "Gastrimmune Raises Antibodies That Neutralize Amidated and Glycine-extended Gastrin-17 and Inhibit the Growth of Colon Cancer," Cancer Research. vol. 56 pp. 880-885 (1996).
Watson et al., "Antibodies Targeting the Amino Terminal Portion of the Human CCKB/Gastrin Receptor Inhibit the Liver Invasion of a Human Colonic Tumour," Gastroenterology. vol. 114, No. 4, Part 2 p. A701 (1998) [Abstract # G2899].
Watson et al., "Therapeutic effect of the gastrin receptor antagonist, CR2093 on gastrointestinal tumour cell growth," British Journal of Cancer. vol. 65, No. 6 pp. 879-883 (1992).
Watson et al., "Synergistic inhibitory effects of G17DT on gastrointestinal tumour growth in combination with cytotoxic agents," Proc. Am. Soc. Clin. Oncol. vol. 22 (2003) [Abstract # 3497] (3 pages).
Watson, S.A. and Gilliam, A.D., "G17DT—a new weapon in the therapeutic armoury for gastrointestinal malignancy," Expert Opinion on Biological Theory. vol. 1, No. 2 pp. 309-317 (2001).

(56) References Cited

OTHER PUBLICATIONS

Watson et al., "Gastrin: growth enhancing effects on human gastric and colonic tumour cells," British Journal of Cancer. vol. 59, No. 4 pp. 554-558 (1988).
Watson et al., "Detection of Gastrin Receptors on Gastrointestinal Tumours Using the Anti-Gastrin Receptor Monoclonal Antibody, 2CL," Gut. vol. 4 p. S68 (1993) [Abstract # F271].
Watson et al., "Expression of gastrin/CCKB receptor isoforms in gastrointestinal tumor cells: Relationship to gastrin secretion," Proceedings of the American Association for Cancer Research Annual Meeting. vol. 38 p. 116 (1997) [Abstract # 773].
Watson et al., "Expression of CCKB/Gastrin Receptor Isoforms in Gastro-intestinal Tumour Cells," International Journal of Cancer. vol. 77, No. 4 pp. 572-577 (1998).
Watson, S.A., and Steele, R.J.C., "Gastrin antagonists in the treatment of gastric cancer," Anti-Cancer Drugs. vol. 4, No. 6 pp. 599-604 (1993).
Watson, S.A., and Smith, A.M., "Hypergastrinemia Promotes Adenoma Progression in the APCMin-/+ Mouse Model of Familial Adenomatous Polyposis," Cancer Research. vol. 61 pp. 625-631 (2001).
Watson et al., "Inhibitory Effects of the Gastrin Receptor Antagonist (L-365,260) on Gastrointestinal Tumor Cells," Cancer. vol. 68 pp. 1255-1260 (1991).
Watson et al., "Intracellular Gastrin in Human Gastrointestinal Tumor Cells," Journal of the National Cancer Institute. vol. 83, No. 12 pp. 866-871 (1991).
Watson et al., "Pre-Clinical Evaluation of the Gastrimmune Immunogen Alone and in Combination With 5-Fluorouracil/Leucovorin in a Rat Colorectal Cancer Model," International Journal of Cancer. vol. 75, No. 6 pp. 873-877 (1998).
Watson et al., "Gastrin—active participant or bystander in gastric carcinogenesis?" Nature Reviews Cancer, vol. 6, pp. 936-946 (2006).
Watson et al., "Growth-promoting action of gastrin on human colonic and gastric tumour cells cultured in vitro," British Journal of Surgery. vol. 75, No. 4 pp. 342-345 (1988).
Watson, S., and Steele, R., "Gastrin Receptors in Gastrointestinal Tumors," CRC Press. Boca Raton, Florida. pp. 1-36, 43-61 and 63-99 (1993).
Weinberg et al., "Cholecystokinin A and B Receptors Are Differentially Expressed in Normal Pancreas and Pancreatic Adenocarcinoma," The Journal of Clinical Investigation. vol. 100, No. 3 pp. 597-603 (1997).
Weiner, L.M., "An Overview of Monoclonal Antibody Therapy of Cancer," Seminars in Oncology. vol. 26, No. 4, Suppl. 12 pp. 41-50 (1999).
Weinstock et al., "Binding of Gastrin17 to Human Gastric Carcinoma Cell Lines," Cancer Research. vol. 48, No. 4 pp. 932-937 (1988).
Wendlberger et al., "The syntheses of human big gastrin I and its 32-leucine analog," Chemical Abstracts. vol. 92, No. 21 p. 722 (1980) [Abstract# 92:198749s].
Wetscher et al., "Pathophysiology of Gastroesophageal Reflux Disease," R.A. Heinder ed., R.G. Landes Co., Chapter 2 pp. 7-29 (1993).
Wong et al., "Postprandial hypergastrinaemia in patients with colorectal cancer," Gut. vol. 32 pp. 1352-1354 (1991).
Written Opinion corresponding to International Patent Application No. PCT/US2004/009666 dated Nov. 7, 2004.
International Search Report and Written Opinion of the International Searching Authority corresponding to International Patent Application No. PCT/US2018/037737 dated Sep. 13, 2018.
Wunsch, E., and Moroder, L., "Biological and Immunological Properties of Human Gastrin I Analogues," Hoppe-Syeler's Z. Physiol. Chem. vol. 363 pp. 665-669 (1982).
Yamaguchi et al., "Amino-terminal immunoreactivity of big gastrin in plasma and tumors obtained from patients with Zollinger-Ellison Syndrome," Chem. Abstracts. vol. 100 p. 373 (1984) [Abstract # 100:154661m].
Yanaihara et al. "A New Type of Gastrin Derivative and its Use for Production of Central Region-Specific Anti-Gastrin Sera," Biomedical Research. vol. 1 pp. 242-247 (1980).
Yanaihara et al. "Human Big Gastrin N-Terminal Fragment Immunoreactivity," Gut Peptides, Elsevier, North-Holland Biomed. Press, pp. 26-33 (1979).
Yuki et al., "YM022, A Potent and Selective Gastrin/CCK-B Receptor Antagonist, Inhibits Peptone Meal-Induced Gastric Acid Secretion in Heidenhain Pouch Dogs," Digestive Diseases and Sciences. vol. 42, No. 4 pp. 707-714 (1997).
Zeitoun, "Comparison of Omeprazole with Ranitidine in the Treatment of Reflux Oesophagitis," Scand. J. Gastroenterol. vol. 24, Suppl. 166 pp. 83-87 (1989).
Zeng et al., "Localization of PACAP Receptors On Rat Fundic ECL and D Cells," Gastroenterology. vol. 110, Suppl. 4 p. A1136 (1996) [Abstract].
Zhang et al., "Precision Immuno-Oncology: Prospects of Individualized Immunotherapy for Pancreatic Cancer." Cancers (Basel), vol. 10(2), Article 39 (15 pages) (2018).
Zhou et al., "Pre—and Postoperative Sequential Study on the Serum Gastrin Level in Patients with Lung Cancer," Journal of Surgical Oncology. vol. 51 pp. 22-25 (1992).

\* cited by examiner

SEQUENCE LISTING

```
Sequence total quantity: 5
SEQ ID NO: 1          moltype = AA  length = 10
FEATURE               Location/Qualifiers
source                1..10
                      mol_type = protein
                      organism = Homo sapiens
SEQUENCE: 1
EGPWLEEEEE                                                                        10

SEQ ID NO: 2          moltype = AA  length = 9
FEATURE               Location/Qualifiers
source                1..9
                      mol_type = protein
                      organism = Homo sapiens
SEQUENCE: 2
```

```
EGPWLEEEE                                                                   9

SEQ ID NO: 3          moltype = AA  length = 12
FEATURE               Location/Qualifiers
source                1..12
                      mol_type = protein
                      organism = Homo sapiens
SEQUENCE: 3
EGPWLEEEEE AY                                                              12

SEQ ID NO: 4          moltype = AA  length = 17
FEATURE               Location/Qualifiers
source                1..17
                      mol_type = protein
                      organism = Homo sapiens
SEQUENCE: 4
EGPWLEEEEE AYGWMDF                                                         17

SEQ ID NO: 5          moltype = AA  length = 15
FEATURE               Location/Qualifiers
source                1..15
                      mol_type = protein
                      organism = Homo sapiens
SEQUENCE: 5
PEGPWLEEEE EAYGW                                                           15
```

COMPOSITIONS AND METHODS FOR INDUCING HUMORAL AND CELLULAR IMMUNITIES AGAINST TUMORS AND CANCER

CROSS-REFERENCE TO RELATED APPLICATION

This application is a divisional of U.S. patent application Ser. No. 16/622,841, filed Dec. 13, 2019 (pending), which is a U.S. National Stage application of PCT International Patent Application Serial No. PCT/US2018/037737, filed Jun. 15, 2018 (expired), which claims the benefit of U.S. Provisional Patent Application Ser. No. 62/520,267, filed Jun. 15, 2017, the disclosure of each of which is incorporated herein by reference in its entirety.

REFERENCE TO SEQUENCE LISTING XML

The Sequence Listing XML associated with the instant disclosure has been electronically submitted to the United States Patent and Trademark Office via the Patent Center as a 5,270 byte UTF-8-encoded XML file created on Nov. 14, 2022 and entitled "1734_10_22_4_PCT_US_DIV.xml". The Sequence Listing submitted via Patent Center is hereby incorporated by reference in its entirety.

TECHNICAL FIELD

The presently disclosed subject matter relates to compositions and methods for inducing both humoral and cellular immunities against tumors and cancers. In some embodiments, the presently disclosed subject matter relates to administering to a subject in need thereof a therapeutic inducer of a humoral or cellular immune response against a gastrin peptide and/or in combination with an inducer of a cellular immune response against the tumor or the cancer.

BACKGROUND

Pancreatic cancer, generally referred to as pancreatic ductal adenocarcinoma (PDAC) is a complex disease involving the successive accumulation of genetic mutations in several cell growth regulatory pathways. What begins as relatively benign lesions in a pancreatic intraepithelial neoplasia (PanIN; Hruban et al., 2008) progresses into a diversity of abnormal gene expression patterns, genomic instability, and ultimately invasive cancer that is resistant to treatment.

Histologically, PDAC is generally well-differentiated and is primarily defined by acinar-ductal metaplasia, the presence of immunosuppressive inflammatory cells, lack of cytotoxic T-cells, and the presence of a dense fibrotic stroma. These manifestations can vary greatly in extent and can occur without overt clinical symptoms, which makes early diagnosis of PDAC a rarity. The PDAC tumor stroma consists of mesenchymal cells such as fibroblasts and pancreatic stellate cells (PSCs), extracellular matrix proteins, peri-tumoral nerve fibers, endothelial cells, and immune cells. The specific mechanisms influencing the stromal cells to produce the abundant desmoplastic effects involve growth factor activation, collagen and extracellular matrix synthesis and secretion (Zhang et al., 2007), as well as the expression of numerous regulators of vascular and cytokine-mediated processes (Hidalgo et al., 2012).

Invasive PDAC constitutes the vast majority (>85%) of carcinomas of ductal lineage. PDAC is characterized by uncontrolled infiltration and early metastases. The presumed precursors of ductal adenocarcinoma are the PanIN microscopic lesions that undergo intraductal proliferative changes and ultimately a series of neoplastic transformations from PanIN-1A to PanIN-3 and full-blown malignant carcinoma.

Important characteristics of PDAC are aberrant expression of the gastrin/cholecystokinin receptor (CCK-B) on the surface of tumor cells (Smith et al., 1994) as well as the expression of high levels of gastrin by the tumor (Prasad et al., 2005). Both gastrin (Smith, 1995) and cholecystokinin (Smith et al., 1990; Smith et al., 1991) proteins stimulate pancreatic tumor growth through an autocrine mechanism (Smith et al., 1996a; Smith et al., 1998b), and inhibition of either gastrin expression (Matters et al., 2009), or blockage of CCK-B receptor function (Fino et al., 2012; Smith & Solomon, 2014) inhibits cancer growth.

In spite of impressive success in the treatment of many cancers over the years, tragically there has been little to no success in the market approval of breakthrough therapeutics for PDAC (see Hidalgo, 2010; Ryan et al., 2014), which carries the poorest prognosis of all gastrointestinal malignancies (Siegel et al., 2016). The current five-year survival rate for PDAC is approximately 6%, the lowest of any cancer (Siegel et al., 2016).

The poor outcome of PDAC has not changed for the past 30 years. A multidisciplinary diagnosis followed by surgery and chemo- and radiation therapy is the first-line treatment approach. However, therapies based on the small molecule chemotherapeutics gemcitabine and 5-fluorouracil do not produce satisfying outcomes and mean survival with these regimens remain less than 1 year (Hoff et al., 2011, Conroy et al., 2011).

Contributing factors to the poor survival rates include the inability to diagnose this disease in the early stages, the heterogeneity of cellular and anatomical tumor cells, the high rate of metastasis, and the presence of a dense fibrotic microenvironment that inhibits drug penetration and exposure (Neesse et al., 2013). Inaccessibility of the tumor results in a relative resistance of PDAC to standard chemotherapy and immunotherapy agents (Templeton & Brentnall, 2013) and contributes to the poor prognosis for this fatal disease.

The host immune response is another key factor contributing to the recalcitrant and aggressive nature of PDAC. Immune cells, which are so prominent in the microenvironment of PDAC, do not support anti-tumor immunity (Zheng et al., 2013). Rather, these cells (including macrophages, T-regulatory ($T_{reg}$) cells, and neutrophils), actually promote tumor growth and invasion. In fact, one of the hallmarks of PDAC is its ability to evade immune destruction (Hanahan & Weinberg, 2011).

Cancers, including PDAC, employ many tools to escape and/or defeat attack from the patient's immune system (Pardoll, 2012; Weiner & Lotze, 2012). Components of the tumor metabolic milieu have been shown to regulate these responses (Feig et al., 2012; Quante et al., 2013). A major breakthrough in cancer therapeutics came with the discovery of immune checkpoint pathways that are often regulated by tumor cells as a mechanism of immune resistance (Leach et al., 1996). Antibodies that target proteins in the checkpoint pathways, such as cytotoxic T lymphocyte-associated antigen 4 (CTLA-4), programmed cell death protein 1 (PD-1), and programmed cell death ligand 1 (PD-L1), have been developed and have been shown to be clinically effective in reversing immunoresistance in some cancers, such as melanoma, non-small cell lung carcinoma (NSCLC), and renal cancer (Pardoll, 2012). However, PDAC is characterized by a tumor microenvironment that has a predominance of immune-suppressing T regulatory ($T_{reg}$) cells, lacks CD8+ tumor-infiltrating effector T cells (Feig et al., 2012; Vonderheide & Bayne, 2013; Zheng et al., 2013), and is poorly vascularized. The fibrotic nature of the dense stromal environment as well as the lack of accessibility through the bloodstream explains in part the observation that PDAC responds only modestly, at best, to anti-PD-1 and anti-PD-L1 antibodies (Brahmer et al., 2012, Zhang, 2018).

The expression level of the checkpoint ligand PD-L1 on the surface of PDAC cells is believed to be another determinant of response to immune checkpoint inhibitor immunotherapy (Zheng, 2017). Some studies have suggested that a low level of PD-L1 expression correlates with the lack of response to immune checkpoint inhibitors (Soares et al., 2015), and that stimulation of PD-1 or PD-L1 expression can help to facilitate the effectiveness of anti-checkpoint protein antibodies (Lutz et al., 2014). In other studies of PDAC, PD-L1 was found to be highly expressed in a majority of tumor cells as well as in many tumor samples (Lu et al., 2017). Thus, the effectiveness of immune checkpoint inhibitor therapy could potentially be enhanced by considering the status of PD-L1 in the tumor and in seeking methods for regulating PD-L1 expression to accompany PDAC-targeted therapy.

Currently, clinical trials for treatment of PDAC include combining antibody immune checkpoint inhibitors with chemotherapy, radiation, chemokine inactivation (olaptesed), cyclin dependent kinase inhibition (abemaciclib), TGF-β Receptor I kinase inhibitors (galunisertib), focal adhesion kinase inhibitors (defactinib), CSF1R inhibitors (Pexidartinib), vitamin D, and Poly ADP ribose polymerase inhibitors (niraparib). These studies are aimed at combining agents that might improve the physical penetration of and/or the immune cell presence in the PDAC tumor microenvironment, as well as to improve the effectiveness of immune checkpoint inhibitor treatment. In a recent report (Smith et al., 2018), inhibition of CCK-B receptor function reduced PDAC fibrosis and improved the effectiveness of antibody therapy using an anti-PD-1 antibody (Ab) and an anti-CTLA-4 Ab.

Given the complexity of the PDAC tumor, a deeper understanding is needed of how novel strategies can be used to modify the immune phenotype of the PDAC microenvironment across the heterogeneity of patients and to make the tumor more responsive to both chemo- and immune-based therapies.

Gastric cancer is another devastating cancer, and gastric adenocarcinoma in particular has one of the poorest prognoses of all cancers, with a 5-year survival of up to 30% (Ferlay et al., 2013). Early detection of this malignancy is elusive and requires intentional screening practices, which are not commonly utilized. Most diagnoses are already in advanced stage with median survival of 9-10 months (Wagner et al., 2010; Ajani et al., 2017). The current standard of care for gastric cancer includes surgery when appropriate, followed by radiation and/or chemotherapy with DNA synthesis inhibitors like 5-fluorouracil and/or DNA damaging agents such as cis-platinum.

Targeted therapies have also begun to emerge for the treatment of some gastric cancers. Tumors that express the human epidermal growth factor receptor 2 (EGFR2) can be treated with trastuzumab (sold under the tradename HERCEPTIN® by Genentech, Inc., South San Francisco, California, United States of America) in combination with chemotherapy. Some gastric cancers are also responsive to anti-angiogenesis drugs such as ramucirumab (sold under the tradename CYRAMZA® by Eli Lilly and Company, Indianapolis, Indiana, United States of America). Additional targeted therapies are urgently needed to improve the dismal prognosis for this prevalent malignancy.

Gastric adenocarcinomas typically overexpress gastrin as well as the receptor for gastrin, called the CCK-B receptor (Smith et al., 1998a; McWilliams et al., 1998), and gastrin-mediated proliferative effects upon binding to CCK-B lead to an uncontrolled autocrine cycle of growth and expression in these tumors. Blocking the function of gastrin as a means of therapy for this cancer has been a focus of research for many years (reviewed in Rai et al., 2012). Among the candidates for targeted therapy, the gastrin vaccine Polyclonal Antibody Stimulator (PAS) has shown significant promise in improving survival in gastric cancer in Phase 2 clinical trials and in pancreatic cancer in Phase 2 and Phase 3 clinical trials. PAS vaccination has been shown to elicit a humoral immune response as demonstrated by the production of neutralizing antibodies to gastrin. By eliminating gastrin, the vaccine slows tumor growth and has potential to provide long-term tumor killing activity.

Cancer vaccines that raise an immune response against specific tumor antigens are an attractive treatment strategy when the immune-mediated immobilization or inactivation of the target antigen does not have deleterious effects elsewhere in the body. Peptide vaccines have the potential advantage of narrowing the specificity of the immune response, but they can sometimes have the disadvantage of eliciting a weak immunogenicity. Careful selection of peptide composition as well as incorporation of adjuvant molecules and delivery systems can be necessary to insure a robust response as well as to initiate induction of the desired immunity pathway. Peptides as short as 9-11 amino acids can generate a specific CD8+ T cell-mediated response, though a change of even one amino acid in the epitope can prevent the response (Gershoni et al., 2007).

The choice of epitopes to be included on the peptide requires the consideration of type of immune response desired, including MHC class II epitopes to induce CD4+ helper T cells and MHC class I CD8 epitopes to induce helper T cells and CD8+ cytotoxic T lymphocytes (Li et al., 2014).

The combination of a gastrin peptide vaccine, such as PAS, combined with an immune checkpoint inhibitor represents a novel approach to improving outcome in cancers that are subject to growth stimulation by the gastrin peptide hormone.

SUMMARY

This Summary lists several embodiments of the presently disclosed subject matter, and in many cases, lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter provides pharmaceutical compositions comprising a first agent that induces and/or provides an active and/or a passive humoral immune response against a gastrin peptide and/or a CCK-B receptor and an immune checkpoint inhibitor. In some embodiments, the first agent is selected from the group consisting of a gastrin peptide, an anti-gastrin antibody, and an anti-CCK-R antibody. In some embodiments, the first agent comprises a gastrin peptide, optionally a gastrin peptide comprising, consisting essentially of, or consisting of an amino acid sequence selected from the group consisting of EGPWLEEEEE (SEQ ID NO: 1), EGPWLEEEE (SEQ ID NO: 2), EGPWLEEEEEAY (SEQ ID NO: 3), and EGPWLEEEEEAYGWMDF (SEQ ID NO: 4). In some embodiments, the glutamic acid residue at amino acid 1 of any of SEQ ID NOs: 1-4 is a pyroglutamate residue.

In some embodiments, the gastrin peptide is conjugated to an immunogenic carrier, optionally via a linker. In some embodiments, the immunogenic carrier is selected from the group consisting of diphtheria toxoid, tetanus toxoid, keyhole limpet hemocyanin, and bovine serum albumin. In some embodiments, the linker comprises a ε-maleimido caproic acid N-hydroxysuccinamide ester.

In some embodiments, the linker and the gastrin peptide are separated by an amino acid spacer, optionally wherein the amino acid spacer is between 1 and 10 amino acids in length, further optionally wherein the amino acid spacer is 7 amino acids in length.

In some embodiments, the presently disclosed pharmaceutical compositions further comprise an adjuvant, optionally an oil-based adjuvant.

In some embodiments, the immune checkpoint inhibitor inhibits a biological activity of a target polypeptide selected from the group consisting of cytotoxic T-lymphocyte antigen 4 (CTLA4), programmed cell death-1 receptor (PD-1), and programmed cell death 1 receptor ligand (PD-L1). In some embodiments, the immune checkpoint inhibitor is selected from the group consisting of Ipilimumab, Tremelimumab, Nivolumab, Pidilizumab, Pembrolizumab, AMP514, AUNP12, BMS-936559/MDX-1105, Atezolizumab, MPDL3280A, RG7446, RO5541267, MEDI4736, Avelumab and Durvalumab.

In some embodiments, the gastrin-associated tumor and/or cancer is pancreatic cancer.

In some embodiments of the presently disclosed pharmaceutical compositions, the first agent comprises an amount of a gastrin peptide comprising, consisting essentially of, or consisting of an amino acid sequence selected from the group consisting of EGPWLEEEEE (SEQ ID NO: 1), EGPWLEEEE (SEQ ID NO: 2), EGPWLEEEEEAY (SEQ ID NO: 3), and EGPWLEEEEEAYGWMDF (SEQ ID NO: 4) effective to induce an anti-gastrin humoral response and the second agent comprises an amount of an immune checkpoint inhibitor that is effective to induce or enhance a cellular immune response against a gastrin-associated tumor or cancer when administered to a subject who has gastrin-associated tumor or cancer. In some embodiments, the glutamic acid residue at amino acid 1 of any of SEQ ID NOs: 1-4 is a pyroglutamate residue.

In some embodiments of the presently disclosed pharmaceutical compositions, the first agent comprises one or more anti-CCK-B receptor antibodies and is present in the pharmaceutical composition in an amount sufficient to reduce or inhibit gastrin signaling via CCK-B receptors present on a gastrin-associated tumor or cancer when administered to a subject that has a gastrin-associated tumor or cancer.

In some embodiments, the presently disclosed subject matter also provides methods for treating a gastrin-associated tumor or cancer in a subject. In some embodiments, the methods comprise administering to the subject an effective amount of a composition that comprises a first agent that induces and/or provides an active and/or a passive humoral immune response against a gastrin peptide and/or a CCK-B receptor; and a second agent that induces and/or provides a cellular immune response against the gastrin-associated tumor or cancer. In some embodiments, the first agent is selected from the group consisting of a gastrin peptide, an anti-gastrin antibody, and an anti-CCK-R antibody. In some embodiments, the first agent comprises a gastrin peptide, optionally a gastrin peptide comprising, consisting essentially of, or consisting of an amino acid sequence selected from the group consisting of EGPWLEEEEE (SEQ ID NO: 1), EGPWLEEEE (SEQ ID NO: 2), EGPWLEEEEEAY (SEQ ID NO: 3), and EGPWLEEEEEAYGWMDF (SEQ ID NO: 4). In some embodiments, the glutamic acid residue at amino acid 1 of any of SEQ ID NOs: 1-4 is a pyroglutamate residue. In some embodiments, the gastrin peptide is conjugated to an immunogenic carrier, optionally via a linker, which in some embodiments can be selected from the group consisting of diphtheria toxoid, tetanus toxoid, keyhole limpet hemocyanin, and bovine serum albumin. In some embodiments, the linker comprises a ε-maleimido caproic acid N-hydroxysuccinamide ester. In some embodiments, the linker and the gastrin peptide are separated by an amino acid spacer, optionally wherein the amino acid spacer is between 1 and 10 amino acids in length, further optionally wherein the amino acid spacer is 7 amino acids in length. In some embodiments, the composition further comprises an adjuvant, optionally an oil-based adjuvant. In some embodiments, the inducer of the cellular immune response against the gastrin-associated tumor or cancer comprises an immune checkpoint inhibitor. In some embodiments, the immune checkpoint inhibitor inhibits a biological activity of a target polypeptide selected from the group consisting of cytotoxic T-lymphocyte antigen 4 (CTLA4), programmed cell death-1 receptor (PD-1), and programmed cell death 1 receptor ligand (PD-L1). In some embodiments, the immune checkpoint inhibitor is selected from the group consisting of Ipilimumab, Tremelimumab, Nivolumab, Pidilizumab, Pembrolizumab, AMP514, AUNP12, BMS-936559/MDX-1105, Atezolizumab, MPDL3280A, RG7446, RO5541267, MEDI4736, Avelumab and Durvalumab.

In some embodiments of the presently disclosed methods, the gastrin-associated tumor and/or cancer is pancreatic cancer. In some embodiments, the composition induces a reduction in and/or prevents the development of fibrosis associated with the pancreatic cancer. In some embodiments, the composition is administered in a dose selected from the group consisting of about 50 µg to about 1000 µg, about 50 µg to about 500 µg, about 100 µg to about 1000 µg, about 200 µg to about 1000 µg, and about 250 µg to about 500 µg, and optionally wherein the dose is repeated once, twice, or three times, optionally wherein the second dose is administered 1 week after the first dose and the third dose, if administered, is administered 1 or 2 weeks after the second dose.

In some embodiments, the presently disclosed subject matter also provides methods for treating gastrin-associated tumors and/or cancers. In some embodiments, the methods comprise administering to a subject in need thereof a first agent that directly or indirectly inhibits one or more biological activities of gastrin in the tumor and/or cancer and a second agent comprising a stimulator of a cellular immune response against the tumor and/or the cancer. In some embodiments, the first agent directly or indirectly inhibits one or more biological activities of gastrin in the tumor and/or cancer by providing and/or inducing a humoral immune response against a gastrin peptide, optionally wherein the agent is selected from the group consisting of an anti-gastrin antibody and a gastrin peptide that induces production of neutralizing anti-gastrin antibodies in the subject; and/or comprises a nucleic acid that inhibits expression of a gastrin gene product. In some embodiments, the anti-gastrin antibody is an antibody directed against an epitope present within gastrin-17 (G17). In some embodiments, the epitope is present within the amino acid sequence EGPWLEEEEE (SEQ ID NO: 1), EGPWLEEEE (SEQ ID NO: 2), EGPWLEEEEEAY (SEQ ID NO: 3), or EGPWLEEEEEAYGWMDF (SEQ ID NO: 4). In some embodiments, the gastrin peptide comprises an amino acid sequence selected from the group consisting of EGPWLEEEEE (SEQ ID NO: 1), EGPWLEEEE (SEQ ID NO: 2), EGPWLEEEEEAY (SEQ ID NO: 3), and EGPWLEEEEEAYGWMDF (SEQ ID NO: 4). In some embodiments, the glutamic acid residue at amino acid 1 of any of SEQ ID NOs: 1-4 is a pyroglutamate residue. In some embodiments, the first agent comprises the gastrin peptide conjugated to an immunogenic carrier, optionally an immunogenic carrier selected from the group consisting of diphtheria toxoid, tetanus toxoid, keyhole limpet hemocyanin, and bovine serum albumin. In some embodiments, the gastrin peptide is conjugated to the immunogenic carrier via a linker, optionally a linker that comprises a ε-maleimido caproic acid N-hydroxysuccinamide ester. In some embodiments, the linker and the gastrin peptide are separated by an amino acid spacer, optionally wherein the amino acid spacer is between 1 and 10 amino acids in length, further optionally wherein the amino acid spacer is 7 amino acids in length. In some embodiments, the first agent further comprises an adjuvant, optionally an oil-based adjuvant. In some embodiments, the second agent is an immune checkpoint inhibitor. In some embodiments, the immune checkpoint inhibitor inhibits a biological activity of a target polypeptide selected from the group consisting of cytotoxic T-lymphocyte antigen 4 (CTLA4), programmed cell death-1 receptor (PD-1), and programmed cell death 1 receptor ligand (PD-L1). In some embodiments, the immune checkpoint inhibitor is selected from the group consisting of Ipilimumab, Tremelimumab, Nivolumab, Pidilizumab, Pembrolizumab, AMP514, AUNP12, BMS-936559/MDX-1105, Atezolizumab, MPDL3280A, RG7446, RO5541267, MEDI4736, and Avelumab.

In some embodiments of the presently disclosed method, the gastrin-associated tumor and/or cancer is pancreatic cancer. In some embodiments, the first agent induces a reduction in and/or prevents the development of fibrosis associated with the pancreatic cancer.

In some embodiments, the presently disclosed subject matter provides methods for inhibiting growth of a gastrin-associated tumor and/or cancer in a subject. In some embodiments, the methods comprise administering to the subject a composition that comprises a first agent comprising a gastrin immunogen, one or more anti-gastrin antibodies, one or more anti-CCK-B receptor antibodies, or any combination thereof; and a second agent comprising an immune checkpoint inhibitor. In some embodiments, the first agent is selected from the group consisting of a gastrin peptide, an anti-gastrin antibody, and an anti-CCK-R antibody. In some embodiments, the first agent comprises a gastrin peptide, optionally a gastrin peptide comprising, consisting essentially of, or consisting of an amino acid sequence selected from the group consisting of EGPWLEEEEE (SEQ ID NO: 1), EGPWLEEEE (SEQ ID NO: 2), EGPWLEEEEEAY (SEQ ID NO: 3), and EGPWLEEEEEAYGWMDF (SEQ ID NO: 4). In some embodiments, the glutamic acid residue at amino acid 1 of any of SEQ ID NOs: 1-4 is a pyroglutamate residue. In some embodiments, the gastrin peptide is conjugated to an immunogenic carrier, optionally wherein the immunogenic carrier is selected from the group consisting of diphtheria toxoid, tetanus toxoid, keyhole limpet hemocyanin, and bovine serum albumin. In some embodiments, the gastrin peptide is conjugated to an immunogenic carrier via a linker, optionally wherein the linker comprises a ε-maleimido caproic acid N-hydroxysuccinamide ester. In some embodiments, the linker and the gastrin peptide are separated by an amino acid spacer, optionally wherein the amino acid spacer is between 1 and 10 amino acids in length, further optionally wherein the amino acid spacer is 7 amino acids in length. In some embodiments, methods employ a composition that further comprises an adjuvant, optionally an oil-based adjuvant. In some embodiments, the inducer of the cellular immune response against the gastrin-associated tumor or cancer comprises an immune checkpoint inhibitor. In some embodiments, the immune checkpoint inhibitor inhibits a biological activity of a target polypeptide selected from the group consisting of cytotoxic T-lymphocyte antigen 4 (CTLA4), programmed cell death-1 receptor (PD-1), and programmed cell death 1 receptor ligand (PD-L1). In some embodiments, the immune checkpoint inhibitor is selected from the group consisting of Ipilimumab, Tremelimumab, Nivolumab, Pidilizumab, Pembrolizumab, AMP514, AUNP12, BMS-936559/MDX-1105, Atezolizumab, MPDL3280A, RG7446, RO5541267, MEDI4736, Avelumab and Durvalumab.

In some embodiments of the presently disclosed methods, the gastrin-associated tumor and/or cancer is pancreatic cancer. In some embodiments, the composition employed in the presently disclosed methods induces a reduction in and/or prevents the development of fibrosis associated with the pancreatic cancer. In some embodiments, the composition is administered in a dose selected from the group consisting of about 50 µg to about 1000 µg, about 50 µg to about 500 µg, about 100 µg to about 1000 µg, about 200 µg to about 1000 µg, and about 250 µg to about 500 µg, and optionally wherein the dose is repeated once, twice, or three times, optionally wherein the second dose is administered 1 week after the first dose and the third dose, if administered, is administered 1 or 2 weeks after the second dose.

The presently disclosed subject matter also provides in some embodiments methods for inducing and/or enhancing cellular immune responses against gastrin-associated tumors and/or cancers in subjects. In some embodiments, the methods comprise administering to a subject that has a gastrin-associated tumor or cancer an effective amount of a composition comprising an agent that reduces or inhibits gastrin signaling via CCK-B receptors present on a gastrin-associated tumor or cancer. In some embodiments, the agent comprises a gastrin peptide, an anti-gastrin antibody, an anti-CCK-B receptor antibody, or any combination thereof. In some embodiments, the gastrin peptide comprises a gastrin-17 (G17) peptide or an immunogenic fragment thereof. In some embodiments, the gastrin peptide or the immunogenic fragment thereof comprises, consists essentially of, or consists of an amino acid sequence selected from the group consisting of EGPWLEEEEE (SEQ ID NO: 1), EGPWLEEEE (SEQ ID NO: 2), EGPWLEEEEEAY (SEQ ID NO: 3), and EGPWLEEEEEAYGWMDF (SEQ ID NO: 4). In some embodiments, the glutamic acid residue at amino acid 1 of any of SEQ ID NOs: 1-4 is a pyroglutamate residue. In some embodiments, the agent comprises a gastrin peptide conjugated to an immunogenic carrier, optionally wherein the immunogenic carrier is selected from the group consisting of diphtheria toxoid, tetanus toxoid, keyhole limpet hemocyanin, and bovine serum albumin. In some embodiments, the gastrin peptide is conjugated to the immunogenic carrier via a linker, optionally a linker comprising a ε-maleimido caproic acid N-hydroxysuccinamide ester. In some embodiments, the linker and the gastrin peptide are separated by an amino acid spacer, optionally wherein the amino acid spacer is between 1 and 10 amino acids in length, further optionally wherein the amino acid spacer is 7 amino acids in length. In some embodiments, the composition employed in the presently disclosed methods further comprises an adjuvant, optionally an oil-based adjuvant.

In some embodiments, the presently disclosed subject matter also provides methods for sensitizing tumors and/or cancers associated with gastrin and/or CCK-B receptor signaling in subject to inducers of cellular immune responses directed against the tumors and/or cancers. In some embodiments, the methods comprise administering to the subject a composition comprising a first agent that induces and/or provides an active and/or a passive humoral immune response against a gastrin peptide, and a second agent that induces and/or provides a cellular immune response against the tumor and/or the cancer, or a combination thereof, optionally wherein the first agent and the second agent are individually selected from the group consisting of a gastrin peptide and/or a fragment and/or a derivative thereof that induces a cellular immune response or production of neutralizing anti-gastrin antibodies in the subject and a neutralizing anti-gastrin antibody and/or a fragment and/or derivative thereof and; and/or a composition comprising a nucleic acid that inhibits expression of a gastrin gene product; and/or a composition comprising an agent that blocks the biological function of gastrin at the CCK-B receptor. In some embodiments, the anti-gastrin antibody is an antibody directed against an epitope present within gastrin-17 (G17). In some embodiments, the epitope is present within the amino acid sequence EGPWLEEEEE (SEQ ID NO: 1) or EGPWLEEEE (SEQ ID NO: 2) or EGPWLEEEEEAY (SEQ ID NO: 3) OR EGPWLEEEEE-AYGWMDF (SEQ ID NO: 4). In some embodiments, the glutamic acid residue at amino acid 1 of any of SEQ ID NOs: 1-4 is a pyroglutamate residue. In some embodiments, the composition comprises the gastrin peptide conjugated to an immunogenic carrier. In some embodiments, the gastrin peptide comprises an amino acid sequence selected from the group consisting of SEQ ID NO: 1, SEQ ID NO: 2, SEQ ID NO: 3 and SEQ ID NO: 4. In some embodiments, the immunogenic carrier is selected from the group consisting of diphtheria toxoid, tetanus toxoid, keyhole limpet hemocyanin, and bovine serum albumin. In some embodiments, the gastrin peptide is conjugated to the immunogenic carrier via a linker. In some embodiments, the linker comprises a ε-maleimido caproic acid N-hydroxysuccinamide ester. In some embodiments, the linker and the gastrin peptide are separated by an amino acid spacer, optionally wherein the amino acid spacer is between 1 and 10 amino acids in length, further optionally wherein the amino acid spacer is 7 amino acids in length. In some embodiments, the composition employed in the presently disclosed methods further comprises an adjuvant, optionally an oil-based adjuvant. In some embodiments, the inducer of the cellular immune response against the gastrin-associated tumor and/or cancer comprises an immune checkpoint inhibitor. In some embodiments, the immune checkpoint inhibitor inhibits a biological activity of a target polypeptide selected from the group consisting of cytotoxic T-lymphocyte antigen 4 (CTLA4), programmed cell death-1 receptor (PD-1), and programmed cell death 1 receptor ligand (PD-L1). In some embodiments, the immune checkpoint inhibitor is selected from the group consisting of Ipilimumab, Tremelimumab, Nivolumab, Pidilizumab, Pembrolizumab, AMP514, AUNP12, BMS-936559/MDX-1105, Atezolizumab, MPDL3280A, RG7446, RO5541267, MEDI4736, Avelumab and Durvalumab.

In some embodiments of the presently disclosed methods, the gastrin-associated tumor and/or cancer is pancreatic cancer. In some embodiments, the composition induces a reduction in and/or prevents the development of fibrosis associated with the pancreatic cancer. In some embodiments, the composition is administered in a dose selected from the group consisting of about 50 μg to about 1000 μg, about 50 μg to about 500 μg, about 100 μg to about 1000 μg, about 200 μg to about 1000 μg, and about 250 μg to about 500 μg, and optionally wherein the dose is repeated once, twice, or three times, optionally wherein the second dose is administered 1 week after the first dose and the third dose, if administered, is administered 1 or 2 weeks after the second dose.

The presently disclosed subject matter also provides in some embodiments methods for preventing, reducing, and/or eliminating formation of fibrosis associated with tumors and/or cancers. In some embodiments, the methods comprise contacting cells of tumors and/or cancers with an agent that directly or indirectly inhibits one or more biological activities of gastrin in the tumor and/or cancer. In some embodiments, the agent provides and/or induces a humoral immune response against a gastrin peptide, optionally wherein the agent is selected from the group consisting of an anti-gastrin antibody, and/or a fragment and/or derivative thereof, and a gastrin peptide that induces production of neutralizing anti-gastrin antibodies in the subject; and/or comprises a nucleic acid that inhibits expression of a gastrin gene product; and/or comprises a small molecule compound that blocks the function of the gastrin hormone. In some embodiments, the anti-gastrin antibody is an antibody directed against an epitope present within gastrin-17 (G17). In some embodiments, the epitope is present within the amino acid sequence EGPWLEEEEE (SEQ ID NO: 1), EGPWLEEEE (SEQ ID NO: 2), EGPWLEEEEEAY (SEQ ID NO: 3), or EGPWLEEEEEAYGWMDF (SEQ ID NO: 4). In some embodiments, the glutamic acid residue at amino acid 1 of any of SEQ ID NOs: 1-4 is a pyroglutamate residue. In some embodiments, the agent comprises the gastrin peptide that induces production of neutralizing anti-gastrin antibodies conjugated to an immunogenic carrier. In some embodiments, the gastrin peptide comprises an amino acid sequence selected from the group consisting of EGPWLEEEEE (SEQ ID NO: 1), EGPWLEEEE (SEQ ID NO: 2), EGPWLEEEEEAY (SEQ ID NO: 3), and EGPWLEEEEEAYGWMDF (SEQ ID NO: 4). In some embodiments, the glutamic acid residue at amino acid 1 of any of SEQ ID NOs: 1-4 is a pyroglutamate residue. In some embodiments, the immunogenic carrier is selected from the group consisting of diphtheria toxoid, tetanus toxoid, keyhole limpet hemocyanin, and bovine serum albumin. In some embodiments, the gastrin peptide is conjugated to the immunogenic carrier via a linker, optionally a linker comprising a ε-maleimido caproic acid N-hydroxysuccinamide ester. In some embodiments, the linker and the gastrin peptide are separated by an amino acid spacer, optionally wherein the amino acid spacer is between 1 and 10 amino acids in length, further optionally wherein the amino acid spacer is 7 amino acids in length. In some embodiments, the agent further comprises an adjuvant, optionally an oil-based adjuvant. In some embodiments, the presently disclosed methods further comprise contacting the tumor and/or the cancer with a second agent comprising a stimulator of a cellular immune response against the tumor and/or the cancer. In some embodiments, the second agent is an immune checkpoint inhibitor. Isae, the immune checkpoint inhibitor inhibits a biological activity of a target polypeptide selected from the group consisting of cytotoxic T-lymphocyte antigen 4 (CTLA4), programmed cell death-1 receptor (PD-1), and programmed cell death 1 receptor ligand (PD-L1). In some embodiments, the immune checkpoint inhibitor is selected from the group consisting of Ipilimumab, Tremelimumab, Nivolumab, Pidilizumab, Pembrolizumab, AMP514, AUNP12, BMS-936559/MDX-1105, Atezolizumab, MPDL3280A, RG7446, RO5541267, MEDI4736, and Avelumab. In some embodiments of the presently disclosed methods, the tumor and/or cancer is pancreatic cancer.

The presently disclosed subject matter also provides in some embodiments uses of the pharmaceutical compositions disclosed herein for producing a medicament for treating a gastrin-associated tumor or cancer.

The presently disclosed subject matter also provides in some embodiments uses of the presently disclosed pharmaceutical compositions for treating a gastrin-associated tumors and/or cancer.

The presently disclosed subject matter also provides in some embodiments uses of the presently disclosed pharmaceutical compositions for preventing, reducing, and/or eliminating metastasis of a gastrin-associated tumor or cancer by administering to a subject having a gastrin-associated tumor or cancer an amount of a pharmaceutical composition as disclosed herein sufficient to enhance the number of $CD4^-/CD8^-$ $T_{EMRA}$ cells in the subject that respond to the gastrin-associated tumor or cancer.

The presently disclosed subject matter also provides in some embodiments uses of the presently disclosed pharmaceutical compositions for increasing the number of $T_{EMRA}$ cells in a subject that respond to a gastrin-associated tumor or cancer.

The presently disclosed subject matter also provides in some embodiments uses of compositions comprising an immune checkpoint inhibitor and a gastrin immunogen to treat a gastrin-associated tumor or cancer.

The presently disclosed subject matter also provides in some embodiments uses of compositions comprising an immune checkpoint inhibitor and a gastrin immunogen for the preparation of a medicament to treat a gastrin-associated tumor or cancer.

The presently disclosed subject matter also provides in some embodiments uses of the presently disclosed pharmaceutical compositions for preventing, reducing, and/or eliminating metastasis of a gastrin-associated tumor or cancer. In some embodiments, the presently disclosed subject matter relates to administering to a subject having a gastrin-associated tumor or cancer an amount of a pharmaceutical composition as disclosed herein sufficient to enhance the number of $CD8^+$ tumor infiltrating lymphocytes. In some embodiments, the use results in improved survival, reduction of tumor growth, and/or enhanced efficacy of chemotherapy and/or immune checkpoint therapy as compared to that seen in subjects that do not receive a pharmaceutical composition as disclosed herein.

Use of the pharmaceutical composition of any one of claims 1-13 for preventing, reducing, and/or eliminating metastasis of a gastrin-associated tumor or cancer by administering to a subject having a gastrin-associated tumor or cancer an amount of the pharmaceutical composition of any one of claims 1-13 sufficient to reduce the number of $FoxP3^+$ inhibitory T-regulatory cells.

Thus, it is an object of the presently disclosed subject matter to provide a method for treating gastrin-associated or CCK-B receptor-containing tumors and/or cancers.

An object of the presently disclosed subject matter having been stated hereinabove, and which is achieved in whole or in part by the compositions and methods disclosed herein, other objects will become evident as the description proceeds when taken in connection with the accompanying Figures as best described herein below.

BRIEF DESCRIPTION OF THE DRAWINGS

FIG. 3A shows the percentages of $CD3^+/CD4^-/CD8^-$ and $CD3^+/CD4^-/CD8^-/CD44^-/CD62L^-$ (i.e. $T_{EMRA}$) cells in mice that underwent various treatments. FIG. 3B shows the portion of $CD3^+/CD4^-/CD8^-$ cells that were $CD3^+/CD4^-/CD8^-/CD44^-/CD62L^-$ $T_{EMRA}$ cells. The portion of cells was calculated by taking the percentage of $CD3^+/CD4^-/CD8^-$ lymphocytes multiplied by the percentage of $CD3^+/CD4^-/CD8^-/CD44^-/CD62L^-$ $T_{EMRA}$ cells in the $CD4^-/CD8^-$ lymphocytes/10000 to calculate the portion of $CD4^-/CD8^-/CD44^-/CD62L^-$ $T_{EMRA}$ cells in the $CD3^+$ T cell fraction (see FIG. 3B). $*p<0.05$; $**p<0.01$. Error bars are ±1 standard deviation.

FIG. 4A shows that the T cells isolated from the spleens of mice treated with PAS100 were indeed activated. When these same cells were re-stimulated with gastrin in culture for 6 hours (FIG. 4B), they were re-stimulated and released even more of each cytokine. Black bars: INFγ. Light gray bars: Granzyme B. Dark gray bars: Perforin. Hatched gray bars: TNFα.

FIG. 6A depicts mT3 tumors stained with Masson's Trichrome Stain, which stains collagen blue and provides an indicator of fibrosis. FIG. 6B is a bar graph summarizing the results of the staining depicted in FIG. 6A. Of note is that whereas the integrated density of the tumors treated with PD-1 monotherapy and PAS100 monotherapy were insignificantly different the negative control PBS treatment, the PAS+PD-1 Ab combination therapy resulted in a decrease in density (and hence fibrosis) that was statistically significant as compared to PBS alone ($p<0.005$) and also PAS100 alone ($p<0.001$). ***$p<0.005$ compared to PBS and $p<0.001$ as compared to PAS100. Black bar: PBS. Light gray bar: PD-1 alone. White bar: PAS100 alone. Hatched gray bar: PAS100+PD-1.

FIG. 7A depicts exemplary mT3 tumors stained with an antibody that binds to the CD8 after treatment with PBS, PD-1 Ab (PD-1) monotherapy, PAS100 monotherapy (patent applications), and PAS100 & PD-1 combination therapy on infiltration of CD8+ cells into mT3 pancreatic cancer cell tumors in mice. FIG. 7B is a bar graph summarizing the data exemplified by FIG. 7A. Treatment with PD-1 (PD-1 Ab) monotherapy or PAS100 alone resulted in significantly higher levels of CD8+ cells in tumors ($p=0.0019$ and $p=0.0026$, respectively) as compared to the negative control PBS treatment. The PAS+PD-1 Ab combination therapy resulted in even greater levels of CD8+ cells in tumors when compared to PBS alone ($p=4.7\times10^{-5}$) as well as when compared to PD-1 alone ($p=0.042$) and when compared to PAS100 alone ($p=0.039$). PD-1 alone compared to PAS100 alone was not significantly different ($p>0.05$). $p=0.0026$; *$p=0.0019$; ****$p=4.7\times10^{-5}$ as compared to PBS. Error bars are ±SEM.

FIG. 8A depicts exemplary mT3 tumors stained with an antibody that binds to the Foxp3 protein, a marker for $T_{regs}$. Comparison of the fields shows that as compared to PBS (upper left panel), PD-1 monotherapy (upper right panel), or PAS100 monotherapy (lower left panel), PAS100 & PD-1 combination therapy resulted in a decrease in the presence of intratumoral $T_{regs}$, suggesting that PAS100+PD-1 combination therapy might modify the intratumoral environment to an extent where the intratumoral microenvironment might be characterized by a lower degree of $T_{reg}$-based immunosuppression as compared to either monotherapy alone. FIG. 8B is a bar graph summarizing the data exemplified by FIG. 8A. As compared to PBS, the number of Foxp3+ cells in tumors treated with PD-1 monotherapy or PAS100 monotherapy was not significantly different. Tumors treated with PAS100+PD-1 Ab combination therapy had significantly fewer Foxp3+ cells than the negative control. *$p=0.038$. Black bar: PBS. Light gray bar: PD-1 Ab alone. White bar: PAS100 alone. Hatched gray bar: PAS100+PD-1 Ab. Error bars are ±SEM.

DETAILED DESCRIPTION

Figure 1:
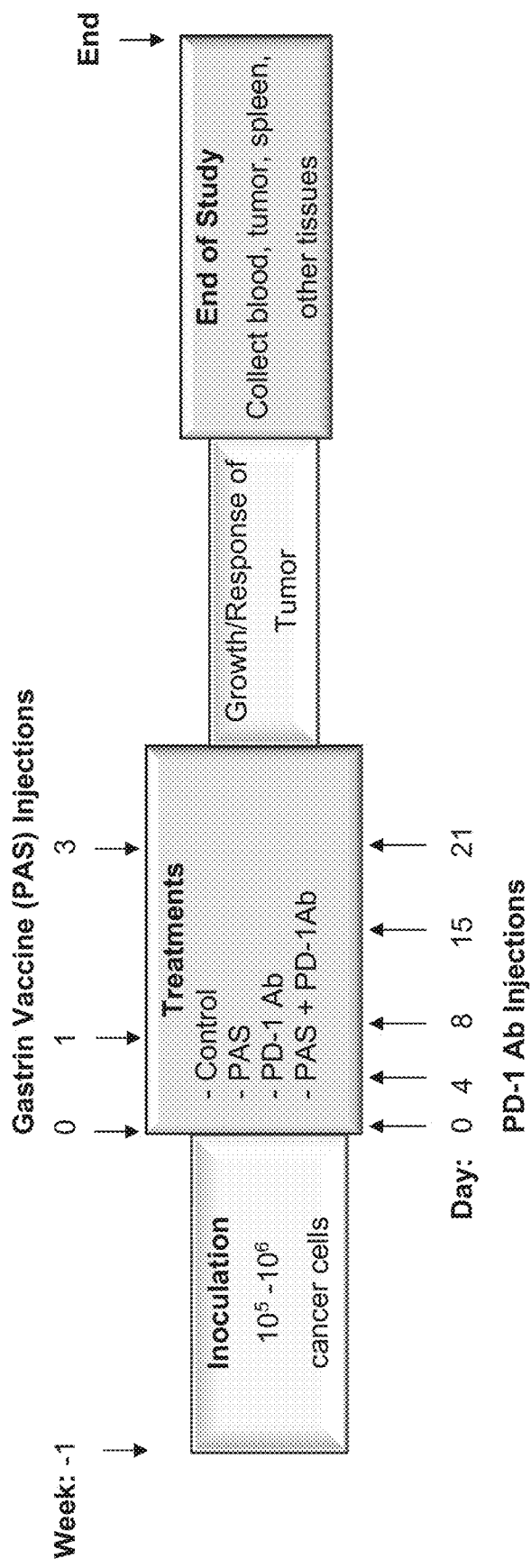
FIG. 1 is a schematic of an exemplary experimental strategy for testing the ability of patent applications with or without an immune checkpoint inhibitor to influence growth of a pancreatic cell tumor in mice. In a particular embodiment, subcutaneous tumors were produced by injecting C57BL/6 mice with $5 \times 10^5$ murine mT3 pancreatic cancer cells (C57BL/6 is syngeneic with mT3 cells) at −1 week before treatment. Groups of 10 mice (40 total) were treated with PAS at t=0, 1, and 3 weeks and/or an anti-PD-1 antibody (PD1-1 Ab; Bio X cell, West Lebanon, New Hampshire, United States of America) at t=0, 4, 8, 15, and 21 days. Between treatments, tumor volumes were measured. The study was ended and PBMC were collected from spleens and tumors were excised from the mice and analyzed.

Headings are included herein for reference and to aid in locating certain sections. These headings are not intended to limit the scope of the concepts described therein under, and these concepts can have applicability in other sections throughout the entire description.

I. General Considerations

The presently disclosed subject matter relates in some embodiments to methods and systems for treating human and animal cancers using combinations of treatments that together generate both a humoral immune anti-tumor effect plus a cellular immune anti-tumor effect. More particularly, the presently disclosed subject matter relates in some embodiments to using particular combinations of drugs that: (1) induce immunologic humoral B cell responses that generate antibodies against the tumor and/or circulating tumor growth factor(s); and (2) induce or otherwise enhance immunologic cellular T cell responses directed against the tumor to elicit cytotoxic T lymphocyte responses. More particularly, the presently disclosed subject matter relates in some embodiments to methods and systems for treating human cancers using an anti-gastrin cancer vaccine in combination with a second drug that causes immune checkpoint blockade. Even more particularly, the presently disclosed subject matter relates in some embodiments to treating specific human cancers with one or more cancer vaccines designed to elicit a B cell antibody response to the active form of the growth factor gastrin. As disclosed herein for the first time, in some embodiments anti-gastrin vaccines can result in a human tumor becoming responsive to treatment with an immune checkpoint inhibitor, thus creating an unexpected additive or even synergistic combination therapy effect that enhances overall anti-tumor efficacy.

The presently disclosed subject matter also relates in some embodiments to methods for the treatment of tumors and/or cancers using a combination of methods, which generate both a humoral antibody immune response (a gastrin cancer vaccine) and a cellular T cell immune response (immune checkpoint blockade). In some embodiments, the presently disclosed subject matter relates to compositions and methods that produce novel, unexpected, additive, and/or synergistic efficacy in treating human and animal gastrointestinal tumors using a novel and unique combination of drug classes which generate both a humoral immune anti-tumor effect plus a cellular immune anti-tumor effect. In some embodiments, the presently disclosed subject matter relates to using specific combinations of drugs that: (1) induce immunologic humoral B cell responses to tumor growth factors and/or circulating tumor growth factors; and (2) cause and/or enhance immunologic cellular T cell responses directed against tumors to elicit cytotoxic T lymphocyte responses. In some embodiments, the presently disclosed subject matter relates to methods and systems for treating human and animal cancers using the presently disclosed combinations of gastrin cancer vaccines and one or more second drugs that causes immune checkpoint blockade. In some embodiments, the presently disclosed subject matter relates to treating specific human cancers with one or more cancer vaccines designed to elicit B cell antibody responses to the active form of the growth factor gastrin, which as disclosed herein unexpectedly also results in the human tumor becoming more responsive to the treatment with an immune checkpoint inhibitor, thus creating an unexpected, additive, or even synergistic combination therapy effect that enhances anti-tumor efficacy. In some embodiments, the presently disclosed subject matter thus relates to using PAS with immune checkpoint inhibitors. In some embodiments, the presently disclosed subject matter relates to using PAS as a cancer vaccine to induce both a humoral and a cellular immune response.

II. Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the presently disclosed and claimed subject matter.

Following long-standing patent law convention, the terms "a", "an", and "the" refer to "one or more" when used in this application, including in the claims. For example, the phrase "an inhibitor" refers to one or more inhibitors, including a plurality of the same inhibitor. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration, or percentage, is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the disclosed compositions. Accordingly, unless indicated to the contrary, the numerical parameters set forth in this specification and attached claims are approximations that can vary depending upon the desired properties sought to be obtained by the presently disclosed subject matter.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

As used herein, the terms "antibody" and "antibodies" refer to proteins comprising one or more polypeptides substantially encoded by immunoglobulin genes or fragments of immunoglobulin genes. Immunoglobulin genes typically include the kappa (κ), lambda (λ), alpha (α), gamma (γ), delta (δ), epsilon (ε), and mu (μ) constant region genes, as well as myriad immunoglobulin variable region genes. Light chains are classified as either κ or λ. In mammals, heavy chains are classified as γ, μ, α, δ, or ε, which in turn define the immunoglobulin classes, IgG, IgM, IgA, IgD, and IgE, respectively. Other species have other light and heavy chain genes (e.g., certain avians produced what is referred to as IgY, which is an immunoglobulin type that hens deposit in the yolks of their eggs), which are similarly encompassed by the presently disclosed subject matter. In some embodiments, the term "antibody" refers to an antibody that binds specifically to an epitope that is present on a gastrin gene product, including but not limited to an epitope that is present within an amino acid sequence as set forth in SEQ ID NO: 1 or SEQ ID NO: 2 or SEQ ID NO: 3 or SEQ ID NO: 4.

A typical immunoglobulin (antibody) structural unit is known to comprise a tetramer. Each tetramer is composed of two identical pairs of polypeptide chains, each pair having one "light" chain (average molecular weight of about 25 kilodalton (kDa)) and one "heavy" chain (average molecular weight of about 50-70 kDa). The two identical pairs of polypeptide chains are held together in dimeric form by disulfide bonds that are present within the heavy chain region. The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively.

Antibodies typically exist as intact immunoglobulins or as a number of well-characterized fragments that can be produced by digestion with various peptidases. For example, digestion of an antibody molecule with papain cleaves the antibody at a position N-terminal to the disulfide bonds. This produces three fragments: two identical "Fab" fragments, which have a light chain and the N-terminus of the heavy chain, and an "Fc" fragment that includes the C-terminus of the heavy chains held together by the disulfide bonds. Pepsin, on the other hand, digests an antibody C-terminal to the disulfide bond in the hinge region to produce a fragment known as the "F(ab)'$_2$" fragment, which is a dimer of the Fab fragments joined by the disulfide bond. The F(ab)'$_2$ fragment can be reduced under mild conditions to break the disulfide linkage in the hinge region, thereby converting the F(ab')$_2$ dimer into two Fab' monomers. The Fab' monomer is essentially an Fab fragment with part of the hinge region (see e.g., Paul, 1993 for a more detailed description of other antibody fragments). With respect to these various fragments, Fab, F(ab')₂, and Fab' fragments include at least one intact antigen binding domain, and thus are capable of binding to antigens.

While various antibody fragments are defined in terms of the digestion of an intact antibody, one of skill will appreciate that various of these fragments (including, but not limited to Fab' fragments) can be synthesized de novo either chemically or by utilizing recombinant DNA methodology. Thus, the term "antibody" as used herein also includes antibody fragments either produced by the modification of whole antibodies or synthesized de novo using recombinant DNA methodologies. In some embodiments, the term "antibody" comprises a fragment that has at least one antigen binding domain.

Antibodies can be polyclonal or monoclonal. As used herein, the term "polyclonal" refers to antibodies that are derived from different antibody-producing cells (e.g., B cells) that are present together in a given collection of antibodies. Exemplary polyclonal antibodies include but are not limited to those antibodies that bind to a particular antigen and that are found in the blood of an animal after that animal has produced an immune response against the antigen. However, it is understood that a polyclonal preparation of antibodies can also be prepared artificially by mixing at least non-identical two antibodies. Thus, polyclonal antibodies typically include different antibodies that are directed against (i.e., binds to) different epitopes (sometimes referred to as an "antigenic determinant" or just "determinant") of any given antigen.

As used herein, the term "monoclonal" refers to a single antibody species and/or a substantially homogeneous population of a single antibody species. Stated another way, "monoclonal" refers to individual antibodies or populations of individual antibodies in which the antibodies are identical in specificity and affinity except for possible naturally occurring mutations, or post-translational modifications that can be present in minor amounts. Typically, a monoclonal antibody (mAb) is generated by a single B cell or a progeny cell thereof (although the presently disclosed subject matter also encompasses "monoclonal" antibodies that are produced by molecular biological techniques as described herein). Monoclonal antibodies (mAbs) are highly specific, typically being directed against a single antigenic site. Furthermore, in contrast to polyclonal antibody preparations, a given mAb is typically directed against a single epitope on the antigen.

In addition to their specificity, mAbs can be advantageous for some purposes in that they can be synthesized uncontaminated by other antibodies. The modifier "monoclonal" is not to be construed as requiring production of the antibody by any particular method, however. For example, in some embodiments, the mAbs of the presently disclosed subject matter are prepared using the hybridoma methodology first described by Kohler et al., 1975, and in some embodiments, are made using recombinant DNA methods in bacterial or eukaryotic animal or plant cells (see e.g., U.S. Pat. No. 4,816,567, the entire contents of which are incorporated herein by reference). mAbs can also be isolated from phage antibody libraries using the techniques described in Clackson et al., 1991 and Marks et al., 1991, for example.

The antibodies, fragments, and derivatives of the presently disclosed subject matter can also include chimeric antibodies. As used herein in the context of antibodies, the term "chimeric", and grammatical variants thereof, refers to antibody derivatives that have constant regions derived substantially or exclusively from antibody constant regions from one species and variable regions derived substantially or exclusively from the sequence of the variable region from another species. A particular kind of chimeric antibody is a "humanized" antibody, in which the antibodies are produced by substituting the complementarity determining regions (CDRs) of, for example, a mouse antibody, for the CDRs of a human antibody (see e.g., PCT International Patent Application Publication No. WO 1992/22653). Thus, in some embodiments, a humanized antibody has constant regions and variable regions other than the CDRs that are derived substantially or exclusively from the corresponding human antibody regions, and CDRs that are derived substantially or exclusively from a mammal other than a human.

The antibodies, fragments, and derivatives of the presently disclosed subject matter can also be single chain antibodies and single chain antibody fragments. Single-chain antibody fragments contain amino acid sequences having at least one of the variable regions and/or CDRs of the whole antibodies described herein but are lacking some or all of the constant domains of those antibodies. These constant domains are not necessary for antigen binding but constitute a major portion of the structure of whole antibodies.

Single-chain antibody fragments can overcome some of the problems associated with the use of antibodies containing a part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and can therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than whole antibodies. The single-chain antibody fragments of the presently disclosed subject matter include but are not limited to single chain fragment variable (scFv) antibodies and derivatives thereof such as, but not limited to tandem di-scFv, tandem tri-scFv, diabodies, and triabodies, tetrabodies, miniantibodies, and minibodies.

Fv fragments correspond to the variable fragments at the N-termini of immunoglobulin heavy and light chains. Fv fragments appear to have lower interaction energy of their two chains than Fab fragments. To stabilize the association of the $V_H$ and $V_L$ domains, they have been linked with peptides (see Bird et al., 1988; Huston et al., 1988), disulfide bridges (Glockshuber et al., 1990), and "knob in hole" mutations (Zhu et al., 1997). ScFv fragments can be produced by methods well known to those skilled in the art (see e.g., Whitlow et al., 1991 and Huston et al., 1993.

scFv can be produced in bacterial cells such as *E. coli* or in eukaryotic cells. One potential disadvantage of scFv is the monovalency of the product, which can preclude an increased avidity due to polyvalent binding, and their short half-life. Attempts to overcome these problems include bivalent (scFv')₂ produced from scFv containing an additional C-terminal cysteine by chemical coupling (Adams et al., 1993; McCartney et al., 1995) or by spontaneous site-specific dimerization of scFv containing an unpaired C-terminal cysteine residue (see Kipriyanov et al., 1995).

Alternatively, scFv can be forced to form multimers by shortening the peptide linker to 3 to 12 residues to form "diabodies" (see Holliger et al., 1993). Reducing the linker still further can result in scFv trimers ("triabodies"; see Kortt et al., 1997) and tetramers ("tetrabodies"; see Le Gall et al., 1999). Construction of bivalent scFv molecules can also be achieved by genetic fusion with protein dimerizing motifs to form "miniantibodies" (see Pack et al., 1992) and "minibodies" (see Hu et al., 1996). scFv-scFv tandems ((scFv)$_2$) can be produced by linking two scFv units by a third peptide linker (see Kurucz et al., 1995).

Bispecific diabodies can be produced through the noncovalent association of two single chain fusion products consisting of V$_H$ domain from one antibody connected by a short linker to the V$_L$ domain of another antibody (see Kipriyanov et al., 1998). The stability of such bispecific diabodies can be enhanced by the introduction of disulfide bridges or "knob in hole" mutations as described hereinabove or by the formation of single chain diabodies (scDb) wherein two hybrid scFv fragments are connected through a peptide linker (see Kontermann et al., 1999).

Tetravalent bispecific molecules can be produced, for example, by fusing an scFv fragment to the CH$_3$ domain of an IgG molecule or to a Fab fragment through the hinge region (see Coloma et al., 1997). Alternatively, tetravalent bispecific molecules have been created by the fusion of bispecific single chain diabodies (see Alt et al., 1999). Smaller tetravalent bispecific molecules can also be formed by the dimerization of either scFv-scFv tandems with a linker containing a helix-loop-helix motif (DiBi miniantibodies; see Muller et al., 1998) or a single chain molecule comprising four antibody variable domains (V$_H$ and V$_L$) in an orientation preventing intramolecular pairing (tandem diabody; see Kipriyanov et al., 1999).

Bispecific F(ab')$_2$ fragments can be created by chemical coupling of Fab' fragments or by heterodimerization through leucine zippers (see Shalaby et al., 1992; Kostelny et al., 1992). Also available are isolated V$_H$ and V$_L$ domains (see U.S. Pat. Nos. 6,172,197; 6,248,516; and 6,291,158).

The presently disclosed subject matter also includes functional equivalents of anti-gastrin antibodies. As used herein, the phrase "functional equivalent" as it refers to an antibody refers to a molecule that has binding characteristics that are comparable to those of a given antibody. In some embodiments, chimerized, humanized, and single chain antibodies, as well as fragments thereof, are considered functional equivalents of the corresponding antibodies upon which they are based.

Functional equivalents also include polypeptides with amino acid sequences substantially the same as the amino acid sequence of the variable or hypervariable regions of the antibodies of the presently disclosed subject matter. As used herein with respect to amino acid sequences, the phrase "substantially the same" refers to a sequence with, in some embodiments at least 80%, in some embodiments at least 85%, in some embodiments at least about 90%, in some embodiments at least 91%, in some embodiments at least 92%, in some embodiments at least 93%, in some embodiments at least 94%, in some embodiments at least 95%, in some embodiments at least 96%, in some embodiments at least 97%, in some embodiments at least 98%, and in some embodiments at least about 99% sequence identity to another amino acid sequence, as determined by the FASTA search method in accordance with Pearson & Lipman, 1988. In some embodiments, the percent identity calculation is performed over the full length of the amino acid sequence of an antibody of the presently disclosed subject matter.

Functional equivalents further include fragments of antibodies that have the same or comparable binding characteristics to those of a whole antibody of the presently disclosed subject matter. Such fragments can contain one or both Fab fragments, the F(ab')$_2$ fragment, the F(ab') fragment, an Fv fragment, or any other fragment that includes at least one antigen binding domain. In some embodiments, the antibody fragments contain all six CDRs of a whole antibody of the presently disclosed subject matter, although fragments containing fewer than all of such regions, such as three, four, or five CDRs, can also be functional equivalents as defined herein. Further, functional equivalents can be or can combine members of any one of the following immunoglobulin classes: IgG, IgM, IgA, IgD, and IgE, and the subclasses thereof, as well as other subclasses as might be appropriate for non-mammalian subjects (e.g., IgY for chickens and other avian species).

Functional equivalents further include peptides that have the same or comparable characteristics to those of a whole protein of the presently disclosed subject matter. Such peptides can contain one or more antigens of the whole protein, which can elicit an immune response in the treated subject.

Functional equivalents also include aptamers and other non-antibody molecules, provided that such molecules have the same or comparable binding characteristics to those of a whole antibody of the presently disclosed subject matter.

The term "comprising", which is synonymous with "including" "containing", or "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. It is noted that, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter. For example, a pharmaceutical composition can "consist essentially of" a pharmaceutically active agent or a plurality of pharmaceutically active agents, which means that the recited pharmaceutically active agent(s) is/are the only pharmaceutically active agent(s) present in the pharmaceutical composition. It is noted, however, that carriers, excipients, and/or other inactive agents can and likely would be present in such a pharmaceutical composition and are encompassed within the nature of the phrase "consisting essentially of".

With respect to the terms "comprising", "consisting of", and "consisting essentially of", where one of these three terms is used herein, the presently disclosed and claimed subject matter can include the use of either of the other two terms. For example, in some embodiments, the presently disclosed subject matter relates to compositions comprising antibodies. It would be understood by one of ordinary skill in the art after review of the instant disclosure that the presently disclosed subject matter thus encompasses compositions that consist essentially of the antibodies of the presently disclosed subject matter, as well as compositions that consist of the antibodies of the presently disclosed subject matter.

As used herein, the phrase "immune cell" refers to the cells of a mammalian immune system including but not limited to antigen presenting cells, B cells, basophils, cytotoxic T cells, dendritic cells, eosinophils, granulocytes, helper T cells, leukocytes, lymphocytes, macrophages, mast cells, memory cells, monocytes, natural killer cells, neutrophils, phagocytes, plasma cells and T cells.

As used herein, the phrase "immune response" refers to immunities including but not limited to innate immunity, humoral immunity, cellular immunity, immunity, inflammatory response, acquired (adaptive) immunity, autoimmunity, and/or overactive immunity.

As used herein, the phrase "gastrin-associated cancer" is a tumor or cancer or a cell therefrom in which a gastrin gene product acts as a trophic hormone to stimulate tumor and/or cancer cell growth both when exogenously applied to tumor and/or cancer cells and also in vivo through autocrine and paracrine mechanisms. Exemplary gastrin-associated cancers include pancreatic cancer, gastric cancer, gastroesophageal cancer, and colorectal cancer.

The term "polynucleotide" as used herein includes but is not limited to DNA, RNA, complementary DNA (cDNA), messenger RNA (mRNA), ribosomal RNA (rRNA), small hairpin RNA (shRNA), small nuclear RNA (snRNA), short nucleolar RNA (snoRNA), microRNA (miRNA), genomic DNA, synthetic DNA, synthetic RNA, and/or tRNA.

As used herein, the phrases "single chain variable fragment", "single-chain antibody variable fragments", and "scFv" antibodies refer to forms of antibodies comprising the variable regions of only the heavy and light chains, connected by a linker peptide.

The term "subject" as used herein refers to a member of any invertebrate or vertebrate species. Accordingly, the term "subject" is intended to encompass in some embodiments any member of the Kingdom Animalia including, but not limited to the phylum Chordata (e.g., members of Classes Osteichythyes (bony fish), Amphibia (amphibians), Reptilia (reptiles), Aves (birds), and Mammalia (mammals), and all Orders and Families encompassed therein.

The compositions and methods of the presently disclosed subject matter are particularly useful for warm-blooded vertebrates. Thus, in some embodiments the presently disclosed subject matter concerns mammals and birds. More particularly provided are compositions and methods derived from and/or for use in mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also provided is the use of the disclosed methods and compositions on livestock, including but not limited to domesticated swine (pigs and hogs), ruminants, horses, poultry, and the like.

As used herein, the terms "T cell" and "T lymphocyte" are interchangeable and used synonymously. Examples include, but are not limited to, naive T cells, central memory T cells, effector memory T cells, cytotoxic T cells, T regulatory cells, helper T cells and combinations thereof.

As used herein, the phrase "therapeutic agent" refers to an agent that is used to, for example, treat, inhibit, prevent, mitigate the effects of, reduce the severity of, reduce the likelihood of developing, slow the progression of, and/or cure, a disease or disorder such as but not limited to a gastrin-associated tumor and/or cancer.

The terms "treatment" and "treating" as used herein refer to both therapeutic treatment and prophylactic or preventative measures, wherein the object is to prevent or slow down (lessen) the targeted pathologic condition, prevent the pathologic condition, pursue or obtain beneficial results, and/or lower the chances of the individual developing a condition, disease, or disorder, even if the treatment is ultimately unsuccessful. Those in need of treatment include those already with the condition as well as those prone to have or predisposed to having a condition, disease, or disorder, or those in whom the condition is to be prevented.

As used herein, the term "tumor" refers to any neoplastic cell growth and/or proliferation, whether malignant or benign, and all pre-cancerous and cancerous cells and tissues the initiation, progression, growth, maintenance, of metastasis of which is directly or indirectly influenced by autocrine and/or paracrine action of gastrin. The terms "cancer" and "tumor" are used interchangeably herein and can refer to both primary and metastasized solid tumors and carcinomas of any tissue in a subject, including but not limited to pancreatic cancer, gastric cancer, gastroesophageal cancer, and colorectal cancer (referred to herein collectively as "gastrin-associated" tumors and/or cancers). As used herein, the terms 37 cancer and "tumor" are also intended to refer to multicellular tumors as well as individual neoplastic or pre-neoplastic cells. In some embodiments, a cancer or a tumor comprises a cancer or tumor of an epithelial tissue such as, but not limited to a carcinoma. In some embodiments, a tumor is an adenocarcinoma, which in some embodiments is an adenocarcinoma of the pancreas, liver, stomach, esophagus, colon, or rectum, and/or a metastatic cell derived therefrom. In some embodiments, a tumor and/or a cancer is associated with fibrosis, meaning that as a direct or indirect consequence of the development of the tumor and/or the cancer, one or more regions of fibrosis typically develop in the area of the tumor and/or the cancer.

All genes, gene names, and gene products disclosed herein are intended to correspond to homologs and/or orthologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the gastrin gene products presented in GENBANK® biosequence database Accession No: NP_000796.1, the human amino acid sequence disclosed is intended to encompass homologous and orthologous gastrin genes and gene products from other animals including, but not limited to other mammals, fish, amphibians, reptiles, and birds. Also encompassed are any and all nucleotide sequences that encode the disclosed amino acid sequences, including but not limited to those disclosed in the corresponding GENBANK® entries (i.e., NP_000796.1 and NM_000805.4, respectively).

III. Development of an Anti-Gastrin Vaccine

A unique approach to tumor-associated antigen-based vaccines has been undertaken by exploiting the involvement of gastrin as a key autocrine and paracrine growth factor for PC and other gastrointestinal cancers. This approach involves neutralizing gastrin's trophic effects through an active humoral immunity against gastrin-17 (G17) with a compound called "Polyclonal Antibody Stimulator" or PAS. PAS comprises a 9-amino acid gastrin epitope derived from the N-terminal sequence of G17 that is identical in mice and humans and conjugated the same to diphtheria toxoid (DT) through a linker molecule. This compound has been formulated in an oil-based adjuvant to create PAS. PAS stimulates the production of specific and high-affinity polyclonal anti-G17 antibodies, whereas DT alone had no effect (Watson et al., 1996). Preclinical studies were performed in several animal models with gastrointestinal (GI) cancer that are gastrin responsive, including colon cancer (Singh et al., 1986; Smith & Solomon, 1988; Upp et al., 1989; Smith et al., 1996b), gastric cancer (Smith et al., 1998a; Watson et al., 1989), lung cancer (Rehfeld et al., 1989), and pancreatic cancer (Smith et al., 1990; Smith et al., 1991; Smith et al., 1995; Segal et al., 2014).

In animals, PAS-generated anti-G17 antibodies have been shown to reduce the growth and metastasis of gastrointestinal tumors (Watson et al., 1995; Watson et al., 1996; Watson et al., 1999). Both active immunizations with PAS and passive immunization with PAS-generated anti-G17 antibodies (Watson et al., 1999) have been shown to inhibit tumor growth in animal models of GI cancers (Watson et al., 1998; Watson et al., 1999).

A prospective, randomized, double-blind, placebo controlled group sequential trial of PAS for the treatment of advanced pancreatic cancer was conducted in human subjects with advanced pancreatic cancer. The primary objective of this study was to compare the effect of monotherapy PAS to placebo on patient survival. Overall, 65% of patients generated an antibody response to PAS. Subjects in the PAS treated group survived longer that the placebo group (average 150 days vs. 84 days, respectively; p=0.016). However, when patients were stratified based upon whether they generated an immune response to PAS (i.e., PAS responders) or did not generate an immune response (i.e., PAS non-responders), survival was significantly increased (p=0.003) in the responders.

To date, 469 patients with PDAC have been treated with PAS in clinical trials. Approximately 90% of these subjects elicited a protective antibody titer. Pooled data from four of the studies (PC1, PC2, PC3, and PC6; Brett et al., 2002; Gilliam et al., 2012) showed that responder patients had a significant increase in median survival days (191 days) compared with non-responder patients (106 days; p=0.0003). Importantly, none of these patients exhibited any evidence of an autoimmune-type reaction that negatively influenced the normal level and function of gastrin.

PAS is known to elicit a B cell response with generation of neutralizing antibodies to gastrin. However, clinical studies demonstrated that there were also long-term survivors, which suggested that additional mechanisms of anti-tumor immunity could also have been responsible.

IV. PAS+Check Point Inhibitor Combination Therapies

IV.A. Generally

PAS administration generates a humoral antibody response and a cellular immune response to the onco-fetal protein gastrin, which is inappropriately expressed (i.e., overexpressed) in PDAC. This inappropriate gastrin expression in PDAC causes an autocrine and paracrine growth-promoting effect. PAS administration with its subsequent generation of humoral antibodies to gastrin, will help eliminate this pathological growth-promoting effect. In addition, a PAS-mediated humoral immune response to gastrin will also help reverse the promotion of angiogenesis, circumvention of apoptosis, increase in cell migration, and increase in invasive enzyme expression that are associated with inappropriate gastrin expression (Watson et al., 2006).

PAS comprises 3 subunits. The first subunit is a gastrin epitope, which in some embodiments is a peptide that comprises amino-terminal amino acid residues 1-9 of human G17 with a carboxy-terminal seven (7) amino acid spacer sequence that terminates in a cysteine residue. An exemplary sequence for this first subunit is EGPWLEEEE (SEQ ID NO: 2).

The second subunit of PAS is a linker that covalently links the first subunit to the third subunit. In some embodiments, the linker is a ε-maleimido caproic acid N-hydroxysuccinamide ester (eMCS), although any linker, including non-peptide linkers such as but not limited to polyethylene glycol linkers, could be used for this purpose.

The third subunit of PAS is a diphtheria toxoid, which is used as a carrier protein to enhance a humoral response directed against the first subunit (in particular, a humoral response directed against the gastric epitope). It is noted, however, that in some embodiments carrier proteins other than diphtheria toxoid could be employed such as but not limited to tetanus toxoid or bovine serum albumin.

In some embodiments, the three subunits are formulated for intramuscular (i.m.) injection, and the formulation has excellent physical, chemical, and pharmaceutical properties. PAS also elicits a B cell response with generation of neutralizing antibodies to gastrin. This is relevant in PDAC, since gastrin increases cellular proliferation, promotes angiogenesis, facilitates circumvention of apoptosis, increases cell migration, increases invasive enzyme expression, and is associated with fibrosis on the PDAC microenvironment. In accordance with some aspects of the presently disclosed subject matter, if the actions of gastrin are blocked, $CD8^+$ lymphocytes influx into PDAC, rendering it more likely to respond to immune checkpoint therapy (e.g., a T-cell mediated response). As disclosed herein. PAS also elicits a T cell response and CD8+ cells that produce cytokines in response to gastrin stimulation.

PAS can be designed as a therapeutic vaccine or immunotherapeutic. PAS-induced humoral antibodies are highly specific and typically characterized by high affinity to G17 and Gly-G17.

PAS consistently induced therapeutically efficacious levels of antibodies that are directed against the hormone G17 and its precursor G17-Gly. Twenty-two clinical studies have been completed with a total of 1,542 patients. Importantly, treatment with PAS demonstrated an excellent safety and tolerability profile, and further resulted in a survival benefit in colorectal, gastric, and pancreatic cancer patients. Used as a monotherapy, an exemplary dose and schedule were identified to be 250 μg/0.2 ml dosed at 0, 1, and 3 weeks.

Taken collectively, the conclusions that can be made from the 22 studies and >1,500 patients treated with PAS are as follows:

(a) Nonclinical data demonstrated both in vitro and in vivo anti-tumor efficacy of anti-G17 antibodies, with a wide therapeutic index in various cancer models, including human pancreatic cancer models;

(b) PAS can be administered at very safe and well tolerated doses, and effectively causes a B cell antibody response to gastrin with no adverse reactions and no induction of negative autoimmune effects; and (c) Numerous clinical studies have demonstrated a survival benefit across gastrointestinal tumors, including pancreatic cancer, and a correlation between generation of anti-G17 antibody response and improved survival.

However, clinical studies have also demonstrated that there were long term survivors, which suggested that additional therapeutic benefits also resulted from PAS administration. While not wishing to be bound by any particular theory of operation, it is possible that PAS treatment might have also induced a T cell immune response characterized by activation of cytotoxic T cells and memory cells in these subjects.

The use of check point inhibitors in PDAC has been limited, and only modest results have been demonstrated. CTLA-4, PD-1, and PD-L1 inhibitors have been investigated in patients with locally advanced or metastatic PDAC in a number of clinical trials (Royal et al., 2010; Brahmer et al., 2012; Segal et al., 2014). Durvalumab (MEDI 4736) has generated a partial response rate of 8% in a preliminary analysis that was presented at the American Society of Clinical Oncology in 2014 (Segal et al., 2014).

It is not known why pancreatic tumors have proven to be relatively resistant to monoclonal antibody (mAb)-based immunotherapeutics that target check point inhibitors. The failure of anti-immune checkpoint inhibitor immunotherapeutics might be related to massive infiltration of immunosuppressive leukocytes, which could actually suppress an anti-tumor immune response. This might be related to expression of the RAS oncogene, which drives an inflammatory program that helps establish immune privilege in the pancreatic tumor microenvironment (Zheng et al., 2013).

IV.B. Check-Point Inhibitors Generate a Cellular Cytotoxic T Cell Response

The immune system has the key central role in differentiating between self (i.e., "normal" cells) and "non-self" or "foreign" cells, whether this be bacteria found in infections or altered and/or transformed cells that are typically found in tumors and cancers. With respect to this process, the immune system requires exquisite regulation to "turn off" when it recognizes "self" so it does not mount an autoimmune reaction to normal body cells while also needing to "turn on" when it recognizes foreign and/or transformed cells. In fact, cell transformation is a relatively common event, but the immune system keeps efficient and effective surveillance on this to effectively and efficiently eliminate foreign and/or transformed cells. Tumor formation and cancer are relatively rare events, since it is only on rare occasions that transformed cells develop mechanisms where they can subvert normal immune system checkpoints, resulting in the immune system not recognizing them as transformed, thus avoiding immune attack by, for example, cytotoxic T lymphocyte attachment to the transformed tumor cells.

Programmed cell Death protein 1 (PD-1; also known as CD279) is a cell surface receptor that serves as a checkpoint that is found on the surface of T cells. PD-1 appears to function as an "off switch" so that T cells do not mount a cytotoxic T lymphocyte attack against normal cells in the body. Human PD-1 is produced as a 288 amino acid precursor protein, an exemplary amino acid sequence for which is provided as Accession No. NP_005009.2 of the GEN-BANK® biosequence database (encoded by GENBANK® Accession No. NM_005018.2). The 288 amino acid precursor includes a signal peptide as amino acids 1-20 of GEN-BANK® Accession No. NP_005009.2, which is removed to produce the mature peptide (i.e., amino acids 21-288 of GENBANK® Accession No. NP_005009.2). The amino acid sequences of orthologs of human PD-1 from other species that are present in the GENBANK® biosequence database include, but are not limited to Accession Nos. NP_032824.1 (*Mus musculus*), NP_001100397.1 (*Rattus norvegicus*), NP_001301026.1 (*Canis lupus familiaris*), NP_001138982.1 (*Felis catus*), NP_001076975.1 (*Bos taurus*), XP_004033550.1 (*Gorilla gorilla gorilla*), NP_001107830.1 (*Macaca mulatta*), NP_001271065.1 (*Macaca fascicularis*), and XP_003776178.1 (*Pongo abelii*).

The ligand for the PD-1 receptor is referred to as the Programmed death-ligand 1 (PD-L1). It is also known as CD274 or the B7 homolog 1 (B7-H1). In humans, there are several isoforms of the PD-L1 protein, the largest of which (isoform a) is produced as a 290 amino acid precursor. An exemplary amino acid sequence for a human PD-L1 precursor a protein is provided as Accession No. NP_054862.1 of the GENBANK® biosequence database (encoded by GENBANK® Accession No. NM_014143.3). The 290 amino acid precursor includes a signal peptide as amino acids 1-18 of GENBANK® Accession No. NP_054862.1, which is removed to produce the mature peptide (i.e., amino acids 19-290 of GENBANK® Accession No. NP_054862.1). The amino acid sequences of orthologs of human PD-L1 from other species that are present in the GENBANK® biosequence database include, but are not limited to Accession Nos. NP_068693.1 (*Mus musculus*), NP_001178883.1 (*Rattus norvegicus*), NP_001278901.1 (*Canis lupus familiaris*), XP_006939101.1 (*Felis catus*), NP_001156884.1 (*Bos taurus*), XP_018889139.1 (*Gorilla gorilla gorilla*), NP_001077358.1 (*Macaca mulatta*), XP_015292694.1 (*Macaca fascicularis*), and XP_009454557.1 (*Pongo troglodytes*).

PD-L1 is found mainly on normal cells, and when a PD-1 expressing T cell binds to a normal cell with PD-L1, it signals to the T cell that this is a normal cell (i.e., "self") and a cytotoxic T cell response against the (normal) cell is suppressed. Most transformed cells are routinely eliminated since they typically do not express PD-L1, meaning that a PD-1 expressing T cell would not be "shut down" but rather "activated" when encountering such a cell, thereby eliminating that transformed cell. However, on rare occasions, the transformed cell does expresses the PD-L1 ligand, resulting in a shutdown of a T cell response to the transformed cell. Hence, transformed cells that express PD-L1 can evade cytotoxic T cell responses. When this occurs, the unrecognized transformed cell can expand, acquire additional mutations, and grow into a malignant, metastatic tumor.

Inhibition of the PD-1/PD-L1 checkpoint (referred to as "immune checkpoint inhibitors") can interfere with PD-1/PD-L1 binding, thereby allowing T lymphocytes to recognize tumor and/or cancer cells as non-self, resulting in cytotoxic T lymphocyte response against the tumor and/or cancer cells. This can be accomplished by drugs that either target PD-1 on T cells or PD-L1 on tumor and/or cancer cells to effectively block PD-1/PD-L1 interactions. Critical to this process are at least two requirements. First, the immune checkpoint inhibitors must get to the site of the tumor and/or cancer to block any interaction between PD-1 and PD-L1. Second, the tumor and/or cancer itself must be accessible to cytotoxic T cells.

Another checkpoint protein is the cytotoxic T-lymphocyte antigen 4 (CTLA-4; also known as CD152) protein. Like PD-1, CTLA-4 is a cell surface receptor that can downregulate immune responses. $T_{regs}$ express CTLA-4, as do activated T cells. When the CTLA-4 receptor binds to CD80 or CD86 present on the surface of antigen-presenting cells (APCs), like PD-1 it functions as an "off switch" with respect to immune responses.

The human CTLA4-TM isoform is a 223 amino acid precursor protein that has the amino acid sequence set forth in GENBANK® Accession No. NP_005205.2 (encoded by GENBANK® Accession No. NM_005214.4). This protein includes a 35 amino acid signal peptide, that when removed generates the 188 amino acid mature peptide. The amino acid sequences of orthologs of human CTLA-4 from other species that are present in the GENBANK® biosequence database include, but are not limited to Accession Nos. NP_033973.2 (*Mus musculus*), NP_113862.1 (*Rattus norvegicus*), NP_001003106.1 (*Canis lupus familiaris*), NP_001009236.1 (*Felis catus*), NP_776722.1 (*Bos taurus*), XP_004033133.1 (*Gorilla gorilla gorilla*), XP_009181095.2 (*Macaca mulatta*), XP_005574073.1 (*Macaca fascicularis*), and XP_526000.1 (*Pan troglodytes*).

As such, in some embodiments the presently disclosed subject matter pertains to the administration of PAS with one or more immune check point inhibitors. More particularly, in some embodiments the presently disclosed subject matter relates to use of immune checkpoint inhibitors that target CTLA-4, PD-1, and/or PD-L1. Exemplary compounds that inhibit these immune checkpoint inhibitors include the following. For CTLA-4: Ipilimumab (YERVOY® brand; Bristol-Myers Squibb, New York, New York) and Tremelimumab (formerly Ticilimumab; Medimmune, LLC, Gaithersburg, Maryland For PD-1: Nivolumab (OPDIVO® brand; Bristol-Myers Squibb, New York, New York), Pidilizumab (Medivation, San Francisco, California), Pembrolizumab (KEYTRUDA® brand; Merck & Co., Inc., Kenilworth, New Jersey), MEDI0680 (AMP514; Medimmune, LLC, Gaithersburg, Maryland), and AUNP-12 (Aurigene Discovery Technologies Limited/Laboratoires Pierre Fabre SA). For PD-L1: BMS-936559/MDX-1105 (Bristol Myers Squibb, New York, New York), Atezolizumab (TECENTRIQ® brand; Genentech/Roche, South San Francisco, California), Durvalumab (MEDI4736; Medimmune, LLC, Gaithersburg, Maryland), and Avelumab (BAVENCIO® brand; EMD Serono, Inc., Rockland, Maryland, and Pfizer Inc., New York, New York).

Evidence strongly suggests there is more commonality rather than divergence related to efficacy and toxicity when one compares the PD-1 and PD-L1 inhibitors. In fact, in cross-trial meta-type analyses, Nivolumab, Pembrolizumab, Avelumab, Atezolizumab, and MDX1105 have been shown to have very similar (but not identical) profiles with respect to toxicity and efficacy. Although affinities and current dosing regimens might differ for the various PD-1 and PD-L1 inhibitors, there is generally a very wide therapeutic window for all. Associated with this broad therapeutic window is the observation that most of these check point inhibitors do not fail in Phase I and many clinical development plans are moving to flat dosing regiments rather than metered dosing.

Although the drugs that target PD-1 and PD-L1 have similar modes of action, efficacy profiles, and toxicity profiles, in general there are some subtle differences between them. Avelumab might have some advantage over other PD-L1 targeted drugs due to capability to complement patent applications-derived B cell responses with an antibody-dependent cell-mediated cytotoxicity (ADDC) response. Avelumab also has a native Fc receptor and therefore can elicit a "normal" ADCC response, whereas Atezolizumab has modifications in the Fc region that might be expected to reduce the ADCC response (at least in humans).

Another difference to note in comparing different PD-1 and PD-L1 targeted drugs is the fact that some are humanized mAbs while others are fully human mAbs. Humanized mAbs might be expected to be characterized by an increased likelihood of inducing "allergic" type reactions compared to fully human mAbs when the humanized mAbs are administered to humans.

V. Compositions

V.A. Pharmaceutical Compositions

In some embodiments, the presently disclosed subject matter provides pharmaceutical compositions that in some embodiments can be employed in the methods of the presently disclosed subject matter.

As used herein, a "pharmaceutical composition" refers to a composition that is to be employed as part of a treatment or other method wherein the pharmaceutical composition will be administered to a subject in need thereof. In some embodiments, a subject in need thereof is a subject with a tumor and/or a cancer at least one symptom, characteristic, or consequence of which is expected to be ameliorated at least in part due to a biological activity of the pharmaceutical composition acting directly and/or indirectly on the tumor and/or the cancer and/or a cell associated therewith.

Techniques for preparing pharmaceutical compositions are known in the art, and in some embodiments pharmaceutical compositions are formulated based on the subject to which the pharmaceutical compositions are to be administered. For example, in some embodiments a pharmaceutical composition is formulated for use in a human subject. Thus, in some embodiments a pharmaceutical composition is pharmaceutically acceptable for use in a human.

The pharmaceutical compositions of the presently disclosed subject matter in some embodiments comprise a first agent that induces and/or provides an active and/or a passive humoral immune response against a gastrin peptide and/or a CCK-B receptor; and an immune checkpoint inhibitor. In some embodiments, the first agent is selected from the group consisting of a gastrin peptide, an anti-gastrin antibody, and an anti-CCK-R antibody. In some embodiments, the first agent comprises a gastrin peptide, optionally a gastrin peptide comprising, consisting essentially of, or consisting of an amino acid sequence selected from the group consisting of EGPWLEEEEE (SEQ ID NO: 1), EGPWLEEEE (SEQ ID NO: 2), EGPWLEEEEEAY (SEQ ID NO: 3), and EGPWLEEEEEAYGWMDF (SEQ ID NO: 4). In some embodiments, the glutamic acid residue an amino acid position 1 of any of SEQ ID NOs: 1-4 is a pyroglutamate residue. In some embodiments, the gastrin peptide is conjugated to an immunogenic carrier, optionally wherein the immunogenic carrier is selected from the group consisting of diphtheria toxoid, tetanus toxoid, keyhole limpet hemocyanin, and bovine serum albumin. In some embodiments, the gastrin peptide is conjugated to an immunogenic carrier via a linker, optionally wherein the linker comprises a ε-maleimido caproic acid N-hydroxysuccinamide ester.

In some embodiments, the linker and the gastrin peptide are separated by an amino acid spacer, optionally wherein the amino acid spacer is between 1 and 10 amino acids in length, further optionally wherein the amino acid spacer is 7 amino acids in length.

Pharmaceutical compositions of the presently disclosed subject matter that are designed to elicit humoral immune responses can in some embodiments further comprise an adjuvant, optionally an oil-based adjuvant. Exemplary adjuvants include but are not limited to montanide ISA-51 (Seppic, Inc.); QS-21 (Aquila Pharmaceuticals, Inc.); Arlacel A; oeleic acid; tetanus helper peptides; GM-CSF; cyclophosamide; bacillus Calmette-Guerin (BCG); corynbacterium parvum; levamisole, azimezone; isoprinisone; dinitrochlorobenezene (DNCB); keyhole limpet hemocyanins (KLH) including Freunds adjuvant (complete and incomplete); mineral gels; aluminum hydroxide (Alum); lysolecithin; pluronic polyols; polyanions; peptides; oil emulsions; nucleic acids (e.g., dsRNA) dinitrophenol; diphtheria toxin (DT); toll-like receptor (TLR, e.g., TLR3, TLR4, TLR7, TLR8 or TLR9) agonists (e.g, endotoxins such as lipopolysaccharide (LPS); monophosphoryl lipid A (MPL); polyinosinic-polycytidylic acid (poly-ICLC/HIL-TONOL®; Oncovir, Inc., Washington, DC, United States of America); IMO-2055, glucopyranosyl lipid A (GLA), QS-21—a saponin extracted from the bark of the *Quillaja saponaria* tree, also known as the soap bark tree or Soap-bark; resiquimod (TLR7/8 agonist), CDX-1401—a fusion protein consisting of a fully human monoclonal antibody with specificity for the dendritic cell receptor DEC-205 linked to the NY-ESO-1 tumor antigen; Juvaris' Cationic Lipid-DNA Complex; Vaxfectin; and combinations thereof.

The pharmaceutical compositions of the presently disclosed subject matter can in some embodiments comprise an immune checkpoint inhibitor. Immune checkpoint inhibitors are a class of compounds that inhibits a biological activity of a target polypeptide selected from the group consisting of cytotoxic T-lymphocyte antigen 4 (CTLA4), programmed cell death-1 receptor (PD-1), and programmed cell death 1 receptor ligand (PD-L1). In some embodiments, the immune checkpoint inhibitor is selected from the group consisting of Ipilimumab, Tremelimumab, Nivolumab, Pidilizumab, Pembrolizumab, AMP514, AUNP12, BMS-936559/MDX-1105, Atezolizumab, MPDL3280A, RG7446, RO5541267, MEDI4736, Avelumab and Durvalumab.

In some embodiments of the presently disclosed pharmaceutical compositions, the first agent comprises an amount of a gastrin peptide comprising, consisting essentially of, or consisting of an amino acid sequence selected from the group consisting of EGPWLEEEEE (SEQ ID NO: 1), EGPWLEEEE (SEQ ID NO: 2), EGPWLEEEEEAY (SEQ ID NO: 3), and EGPWLEEEEEAYGWMDF (SEQ ID NO: 4) effective to induce an anti-gastrin humoral response and the second agent comprises an amount of a checkpoint inhibitor that is effective to induce or enhance a cellular immune response against a gastrin-associated tumor or cancer when administered to a subject who has gastrin-associated tumor or cancer.

In some embodiments of the presently disclosed pharmaceutical compositions, the first agent comprises one or more anti-CCK-B receptor antibodies and is present in the pharmaceutical composition in an amount sufficient to reduce or inhibit gastrin signaling via CCK-B receptors present on a gastrin-associated tumor or cancer when administered to a subject that has a gastrin-associated tumor or cancer.

The pharmaceutical compositions of the presently disclosed subject matter are in some embodiments employed to treat a gastrin-associated tumor and/or cancer. In some embodiments, pharmaceutical compositions of the presently disclosed subject matter are intended to treat pancreatic cancer.

V.B. Nucleic Acids

The term "RNA" refers to a molecule comprising at least one ribonucleotide residue. By "ribonucleotide" is meant a nucleotide with a hydroxyl group at the 2' position of a β-D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material, such as to the end(s) of an siRNA or internally, for example at one or more nucleotides of the RNA. Nucleotides in the RNA molecules of the presently disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

The terms "small interfering RNA", "short interfering RNA", "small hairpin RNA", "siRNA", and shRNA are used interchangeably and refer to any nucleic acid molecule capable of mediating RNA interference (RNAi) or gene silencing. See e.g., Bass, Nature 411:428-429, 2001; Elbashir et al., Nature 411:494-498, 2001a; and PCT International Publication Nos. WO 00/44895, WO 01/36646, WO 99/32619, WO 00/01846, WO 01/29058, WO 99/07409, and WO 00/44914. In one embodiment, the siRNA comprises a double stranded polynucleotide molecule comprising complementary sense and antisense regions, wherein the antisense region comprises a sequence complementary to a region of a target nucleic acid molecule (for example, a nucleic acid molecule encoding a gastrin gene product). In another embodiment, the siRNA comprises a single stranded polynucleotide having self-complementary sense and antisense regions, wherein the antisense region comprises a sequence complementary to a region of a target nucleic acid molecule. In another embodiment, the siRNA comprises a single stranded polynucleotide having one or more loop structures and a stem comprising self-complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

The presently disclosed subject matter takes advantage of the ability of short, double stranded RNA molecules to cause the down regulation of cellular genes, a process referred to as RNA interference. As used herein, "RNA interference" refers to a process of sequence-specific post-transcriptional gene silencing mediated by a small interfering RNA (siRNA). See generally Fire et al., Nature 391:806-811, 1998. The process of post-transcriptional gene silencing is thought to be an evolutionarily conserved cellular defense mechanism that has evolved to prevent the expression of foreign genes (Fire, Trends Genet 15:358-363, 1999).

RNAi might have evolved to protect cells and organisms against the production of double stranded RNA (dsRNA) molecules resulting from infection by certain viruses (particularly the double stranded RNA viruses or those viruses for which the life cycle includes a double stranded RNA intermediate) or the random integration of transposon elements into the host genome via a mechanism that specifically degrades single stranded RNA or viral genomic RNA homologous to the double stranded RNA species.

The presence of long dsRNAs in cells stimulates the activity of the enzyme Dicer, a ribonuclease III. Dicer catalyzes the degradation of dsRNA into short stretches of dsRNA referred to as small interfering RNAs (siRNA; Bernstein et al., Nature 409:363-366, 2001). The small interfering RNAs that result from Dicer-mediated degradation are typically about 21-23 nucleotides in length and contain about 19 base pair duplexes. After degradation, the siRNA is incorporated into an endonuclease complex referred to as an RNA-induced silencing complex (RISC). The RISC is capable of mediating cleavage of single stranded RNA present within the cell that is complementary to the antisense strand of the siRNA duplex. According to Elbashir et al., cleavage of the target RNA occurs near the middle of the region of the single stranded RNA that is complementary to the antisense strand of the siRNA duplex (Elbashir et al., Genes Dev 15:188-200, 2001 b).

RNAi has been described in several cell type and organisms. Fire et al., 1998 described RNAi in *C. elegans*. Wianny & Zernicka-Goetz, Nature Cell Biol 2:70-75, 1999 disclose RNAi mediated by dsRNA in mouse embryos. Hammond et al., Nature 404:293-296, 2000 were able to induce RNAi in Drosophila cells by transfecting dsRNA into these cells. Elbashir et al. Nature 411:494-498, 2001a demonstrated the presence of RNAi in cultured mammalian cells including human embryonic kidney and HeLa cells by the introduction of duplexes of synthetic 21 nucleotide RNAs.

Other studies have indicated that a 5'-phosphate on the target-complementary strand of a siRNA duplex facilitate siRNA activity and that ATP is utilized to maintain the 5'-phosphate moiety on the siRNA (Nykanen et al., Cell 107:309-321, 2001). Other modifications that might be tolerated when introduced into an siRNA molecule include modifications of the sugar-phosphate backbone or the substitution of the nucleoside with at least one of a nitrogen or sulfur heteroatom (PCT International Publication Nos. WO 00/44914 and WO 01/68836) and certain nucleotide modifications that might inhibit the activation of double stranded RNA-dependent protein kinase (PKR), specifically 2'-amino or 2'-O-methyl nucleotides, and nucleotides containing a 2'-O or 4'-C methylene bridge (Canadian Patent Application No. 2,359,180).

Other references disclosing the use of dsRNA and RNAi include PCT International Publication Nos. WO 01/75164 (in vitro RNAi system using cells from Drosophila and the use of specific siRNA molecules for certain functional genomic and certain therapeutic applications); WO 01/36646 (methods for inhibiting the expression of particular genes in mammalian cells using dsRNA molecules); WO 99/32619 (methods for introducing dsRNA molecules into cells for use in inhibiting gene expression); WO 01/92513 (methods for mediating gene suppression by using factors that enhance RNAi); WO 02/44321 (synthetic siRNA constructs); WO 00/63364 and WO 01/04313 (methods and compositions for inhibiting the function of polynucleotide sequences); and WO 02/055692 and WO 02/055693 (methods for inhibiting gene expression using RNAi).

In some embodiments, the presently disclosed subject matter utilizes RNAi to at least partially inhibit expression of at least one gastrin gene product. Inhibition is preferably at least about 10% of normal expression amounts. In some embodiments, the method comprises introducing an RNA to a target cell in an amount sufficient to inhibit expression of a gastrin gene product, wherein the RNA comprises a ribonucleotide sequence which corresponds to a coding strand of a gene of interest. In some embodiments, the target cell is present in a subject, and the RNA is introduced into the subject.

The RNA can have a double-stranded region comprising a first strand comprising a ribonucleotide sequence that corresponds to the coding strand of the gene encoding the target protein (for example, a gastrin gene product) and a second strand comprising a ribonucleotide sequence that is complementary to the first strand. The first strand and the second strand hybridize to each other to form the double-stranded molecule. The double stranded region can be at least 15 basepairs in length, and in some embodiments, between 15 and 50 basepairs in length, and in some embodiments the double stranded region is between 15 and 30 basepairs in length.

In some embodiments, the RNA comprises one strand that forms a double-stranded region by intramolecular self-hybridization, which is preferably complementary over at least 19 bases. In some embodiments, the RNA comprises two separate strands that form a double-stranded region by intermolecular hybridization that is complementary over at least 19 bases.

One skilled in the art will recognize that any number of suitable common techniques can be used to introduce the RNAs into a target cell. In some embodiments, a vector encoding the RNA is introduced to the target cell. For example, the vector encoding the RNA can be transfected into the target cell and the RNA is then transcribed by cellular polymerases.

In some embodiments, a recombinant virus comprising nucleic acid encoding the RNA can be produced. Introducing the RNA into a target cell then comprises infecting the target cell with the recombinant virus. Cellular polymerases transcribe the RNA resulting in expression of the RNA within the target cell. Engineering recombinant viruses is well known to those having ordinary skill in the art. One of skill would readily appreciate the multiple factors involved in selecting the appropriate virus and vector components needed to optimize recombinant virus production for use with the presently disclosed subject matter without the necessity of further detailed discussion herein. As one non-limiting example, a recombinant adenovirus can be engineered comprising DNA encoding an siRNA. The virus can be engineered to be replication deficient such that cells can be infected by the recombinant adenovirus, the siRNA transcribed, and transiently expressed in the infected target cell. Details of recombinant virus production and use can be found in PCT International Patent Application Publication No. WO 2003/006477, herein incorporated by reference in their entireties. Alternatively, a commercial kit for producing recombinant viruses can be used, such as for example, the pSILENCER ADENO 1.0-CMV SYSTEM™ brand virus production kit (Ambion, Austin, Texas, United States of America).

V.C. Gene Editing

Downregulation of gene products can also be accomplished using the CRISPR-Cas gene editing system as described in U.S. Pat. No. 8,945,839 to Zhang and references cited therein, Al-Attar et al., 2011; Makarova et al., 2011; Le Cong et al., 2013; Seung Woo Cho et al., 2013a, b; Carroll, 2012; Gasiunas et al., 2012; Hale et al., 2012; and Jinek et al., 2012, all of which are incorporated herein by reference in their entireties. In some embodiments, the methods and compositions for use in the CRISPR-Cas gene editing system include nucleic acids that target a gastrin gene sequence, which in some embodiments is a gastrin gene sequence in a tumor and/or a cancer.

V.D. Formulations

Compositions as described herein comprise in some embodiments a composition that includes a pharmaceutically acceptable carrier. Suitable formulations include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents. In some embodiments, a formulation of the presently disclosed subject matter comprises an adjuvant, optionally an oil-based adjuvant.

The compositions used in the methods can take such forms as suspensions, solutions, or emulsions in oily or aqueous vehicles, and can contain formulatory agents such as suspending, stabilizing, and/or dispersing agents. The compositions used in the methods can take forms including, but not limited to perioral, intravenous, intraperitoneal, intramuscular, and intratumoral formulations. Alternatively or in addition, the active ingredient can be in powder form for constitution with a suitable vehicle (e.g., sterile pyrogen-free water) before use.

The formulations can be presented in unit-dose or multi-dose containers, for example sealed ampules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulfate). The tablets can be coated by methods known in the art. For example, a neuroactive steroid can be formulated in combination with hydrochlorothiazide, and as a pH stabilized core having an enteric or delayed-release coating which protects the neuroactive steroid until it reaches the colon.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring, and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt).

The compounds can also be formulated in oils that are administered as water-in-oil emulsions, oil-in-water emulsions, or water-in-oil-in water emulsions.

The compounds can also be formulated in rectal compositions (e.g., suppositories or retention enemas containing conventional suppository bases such as cocoa butter or other glycerides), creams or lotions, or transdermal patches.

In some embodiments, the presently disclosed subject matter employs a composition that is pharmaceutically acceptable for use in humans. One of ordinary skill in the art understands the nature of those components that can be present in such a composition that is pharmaceutically acceptable for use in humans and also what components should be excluded from compositions that are pharmaceutically acceptable for use in humans.

V.E. Doses

As used herein, the phrases "treatment effective amount", "therapeutically effective amount", "treatment amount", and "effective amount" are used interchangeably and refer to an amount of a therapeutic composition sufficient to produce a measurable response (e.g., a biologically or clinically relevant response in a subject being treated). Actual dosage levels of active ingredients in the pharmaceutical compositions of the presently disclosed subject matter can be varied so as to administer an amount of the active compound(s) that is effective to achieve the desired therapeutic response for a particular subject. The selected dosage level can depend upon the activity of the therapeutic composition, the route of administration, combination with other drugs or treatments, the severity of the condition being treated, the condition and prior medical history of the subject being treated, etc. However, it is within the skill of the art to start doses of the compound at levels lower than required to achieve the desired therapeutic effect and to gradually increase the dosage until the desired effect is achieved.

The potency of a therapeutic composition can vary, and therefore a "therapeutically effective amount" can vary. However, one skilled in the art can readily assess the potency and efficacy of a candidate modulator of the presently disclosed subject matter and adjust the therapeutic regimen accordingly.

After review of the disclosure herein of the presently disclosed subject matter, one of ordinary skill in the art can tailor the dosages to an individual subject, taking into account the particular formulation, method of administration to be used with the composition, and other factors. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

Thus, in some embodiments the term "effective amount" is used herein to refer to an amount of a composition comprising an agent that provides and/or induces a humoral or cellular immune response against a gastrin peptide and or comprising a nucleic acid that inhibits expression of a gastrin gene product, a pharmaceutically acceptable salt thereof, a derivative thereof, or a combination thereof sufficient to produce a measurable anti-tumor and/or anti-cancer biological activity. Actual dosage levels of active ingredients in composition of the presently disclosed subject matter can be varied so as to administer an amount of the active compound(s) that is effective to achieve the desired response for a particular subject and/or application. The selected dosage level can depend upon a variety of factors including the activity of the composition, formulation, route of administration, combination with other drugs or treatments, severity of the condition being treated, and physical condition and prior medical history of the subject being treated. In some embodiments, a minimal dose is administered, and dose is escalated in the absence of dose-limiting toxicity to a minimally effective amount. Determination and adjustment of an effective dose, as well as evaluation of when and how to make such adjustments, are known to those of ordinary skill in the art.

For administration of a composition as disclosed herein, conventional methods of extrapolating human dosage based on doses administered to a murine animal model can be carried out using techniques known to one of ordinary skill in the art. Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich et al., 1966. Briefly, to express a mg/kg dose in any given species as the equivalent mg/m² dose, multiply the dose by the appropriate km factor. In an adult human, 100 mg/kg is equivalent to 100 mg/kg×37 kg/m²=3700 mg/m².

For additional guidance regarding formulations and doses, see U.S. Pat. Nos. 5,326,902; 5,234,933; PCT International Publication No. WO 93/25521; Remington et al., 1975; Goodman et al., 1996; Berkow et al., 1997; Speight et al., 1997; Ebadi, 1998; Duch et al., 1998; Katzung, 2001; Gerbino, 2005.

V.F. Routes of Administration

The presently disclosed compositions can be administered to a subject in any form and/or by any route of administration. In some embodiments, the formulation is a sustained release formulation, a controlled release formulation, or a formulation designed for both sustained and controlled release. As used herein, the term "sustained release" refers to release of an active agent such that an approximately constant amount of an active agent becomes available to the subject over time. The phrase "controlled release" is broader, referring to release of an active agent over time that might or might not be at a constant level. Particularly, "controlled release" encompasses situations and formulations where the active ingredient is not necessarily released at a constant rate, but can include increasing release over time, decreasing release over time, and/or constant release with one or more periods of increased release, decreased release, or combinations thereof. Thus, while "sustained release" is a form of "controlled release", the latter also includes delivery modalities that employ changes in the amount of an active agent that are delivered at different times.

In some embodiments, the sustained release formulation, the controlled release formulation, or the combination thereof is selected from the group consisting of an oral formulation, a peroral formulation, a buccal formulation, an enteral formulation, a pulmonary formulation, a rectal formulation, a vaginal formulation, a nasal formulation, a lingual formulation, a sublingual formulation, an intravenous formulation, an intraarterial formulation, an intracardial formulation, an intramuscular formulation, an intraperitoneal formulation, a transdermal formulation, an intracranial formulation, an intracutaneous formulation, a subcutaneous formulation, an aerosolized formulation, an ocular formulation, an implantable formulation, a depot injection formulation, a transdermal formulation and combinations thereof. In some embodiments, the route of administration is selected from the group consisting of oral, peroral, buccal, enteral, pulmonary, rectal, vaginal, nasal, lingual, sublingual, intravenous, intraarterial, intracardial, intramuscular, intraperitoneal, transdermal, intracranial, intracutaneous, subcutaneous, ocular, via an implant, and via a depot injection. Where applicable, continuous infusion can enhance drug accumulation at a target site (see, e.g., U.S. Pat. No. 6,180,082). See also U.S. Pat. Nos. 3,598,122; 5,016,652; 5,935,975; 6,106,856; 6,162,459; 6,495,605; and 6,582,724; and U.S. Patent Application Publication No. 2006/0188558 for transdermal formulations and methods of delivery of compositions. In some embodiments, the administering is via a route selected from the group consisting of peroral, intravenous, intraperitoneal, inhalation, and intratumoral.

The particular mode of administration of the compositions of the presently disclosed subject matter used in accordance with the methods disclosed herein can depend on various factors, including but not limited to the formulation employed, the severity of the condition to be treated, whether the active agents in the compositions (e.g., PAS) are intended to act locally or systemically, and mechanisms for metabolism or removal of the active agents following administration.

VI. Methods and Uses

In some embodiments, the presently disclosed subject matter relates to employing pharmaceutical compositions in the context of various methods and/or uses related to treating gastrin-associated tumors and/or cancers, producing medicaments for treating gastrin-associated tumors and/or cancers, inhibiting growth of gastrin-associated tumors and/or cancers, inducing and/or enhancing humoral and/or cellular immune responses against gastrin-associated tumors and/or cancers, sensitizing tumors and/or cancers associated with gastrin and/or CCK-B receptor signaling in subjects to inducers of cellular immune responses directed against the tumors and/or cancers, preventing, reducing, and/or eliminating formation of fibrosis associated with tumors and/or cancers, particularly in the context of pancreatic cancer; preventing, reducing, and/or eliminating metastases of gastrin-associated tumors and/or cancers; increasing the number of tumor-infiltrating CD8$^+$ lymphocytes in tumors and/or cancers; reducing the number of FoxP3$^+$ inhibitory T-regulatory cells present in tumors and/or cancers; and increasing the number of T$_{EMRA}$ cells in subject that respond to gastrin-associated tumors and/or cancers. Each of these methods and/or uses is described in more detail herein below.

VI.A. Methods for Treating Gastrin-Associated Tumors and/or Cancers

In some embodiments, the presently disclosed subject matter relates to methods for treating gastrin-associated tumors and/or cancers. In some embodiments, the method comprises administering to a subject in need thereof (e.g., a subject with a gastrin-associated tumor and/or cancer) an effective amount of a composition that comprises a first agent that induces and/or provides an active and/or a passive humoral immune response against a gastrin peptide and/or a CCK-B receptor; and a second agent that induces and/or provides a cellular immune response against the gastrin-associated tumor or cancer. Thus, the presently disclosed methods in some embodiments rely on the use of pharmaceutical compositions that have one or more active agents that together provide two distinct immunotherapeutic activities: providing and/or inducing an active and/or a passive humoral immune response against a gastrin peptide and/or a CCK-B receptor, and inducing and/or providing a cellular immune response against the gastrin-associated tumor and/or cancer.

With respect to providing and/or inducing an active and/or a passive humoral immune response against a gastrin peptide and/or a CCK-B receptor, the first agent present in the pharmaceutical compositions of the presently disclosed subject matter is selected from the group consisting of a gastrin peptide designed to induce an active humoral response against gastrin, and/or an anti-gastrin antibody and/or an anti-CCK-R antibody designed to provide a passive humoral response against gastrin and/or a CCK-B receptor, in some embodiments a CCK-B receptor present on gastrin-associated tumor and/or cancer. While not wishing to be bound by any particular theory of action, the active and/or a passive humoral immune response against a gastrin peptide and/or a CCK-B receptor is designed to inhibit, either partially or completely, gastrin signaling in the gastrin-associated tumor and/or cancer via the CCK-B receptor by reducing gastrin binding to the CCK-B receptor by reducing the amount of circulating gastrin present in the subject and/or by interfering with gastrin binding to the CCK-B receptor with neutralizing and/or blocking antibodies.

Thus, in some embodiments the first agent comprises a gastrin peptide, optionally a gastrin peptide comprising, consisting essentially of, or consisting of an amino acid sequence selected from the group consisting of EGPWLEEEEE (SEQ ID NO: 1), EGPWLEEEE (SEQ ID NO: 2), EGPWLEEEEEAY (SEQ ID NO: 3), and EGPWLEEEEEAYGWMDF (SEQ ID NO: 4), wherein the glutamic acid residue at amino acid position 1 of any of SEQ ID NOs: 1-4 is a pyroglutamate residue. In some embodiments, the gastrin peptide is conjugated to an immunogenic carrier, optionally via a linker, further optionally a linker comprising a ε-maleimido caproic acid N-hydroxysuccinamide ester, in the pharmaceutical composition. Non-limiting examples of immunogenic carriers include diphtheria toxoid, tetanus toxoid, keyhole limpet hemocyanin, and bovine serum albumin. The structure of the first agent is described in more detail herein above, but in some embodiments the linker and the gastrin peptide are separated by an amino acid spacer, optionally wherein the amino acid spacer is between 1 and 10 amino acids in length, further optionally wherein the amino acid spacer is 7 amino acids in length.

As would be appreciated by one of ordinary skill in the art upon consideration of this disclosure, in some embodiments the pharmaceutical composition further comprises an adjuvant, optionally an oil-based adjuvant, to enhance the immunogenicity of the gastrin peptide and/or the gastrin peptide conjugate when an active anti-gastrin humoral immune response is desired.

In order to induce a cellular immune response against the gastrin-associated tumor or cancer, the methods of the presently disclosed subject matter employ pharmaceutical compositions that comprise one or more checkpoint inhibitors. As is known, checkpoint inhibitors inhibit one or more biological activities of target polypeptides that have immune checkpoint activities. Exemplary such polypeptides include cytotoxic T-lymphocyte antigen 4 (CTLA4) polypeptides, programmed cell death-1 receptor (PD-1) polypeptides, and programmed cell death 1 receptor ligand (PD-L1) polypeptides. In some embodiments, a checkpoint inhibitor comprises an antibody or a small molecule that binds to and/or interferes with interactions between T cells and tumor cells by inhibiting or preventing interactions between PD-1 polypeptides and PD-L1 polypeptides. Exemplary such antibodies and small molecules include but are not limited to Ipilimumab, Tremelimumab, Nivolumab, Pidilizumab, Pembrolizumab, AMP514, AUNP12, BMS-936559/MDX-1105, Atezolizumab, MPDL3280A, RG7446, RO5541267, MEDI4736, Avelumab and Durvalumab.

The pharmaceutical compositions of the presently disclosed subject matter can include various amounts of the first and second agents, provided that both humoral and cellular responses are induced and/or provided in the subject, and the amounts of the first and second agents present in the pharmaceutical compositions can be adjusted in order to maximize the effectiveness of the treatment and/or minimize undesirable side effects thereof. However, in some embodiments a pharmaceutical composition of the presently disclosed subject matter is administered in a dose selected from the group consisting of about 50 μg to about 1000 μg, about 50 μg to about 500 μg, about 100 μg to about 1000 μg, about 200 μg to about 1000 μg, and about 250 μg to about 500 μg, and optionally wherein the dose is repeated once, twice, or three times, optionally wherein the second dose is administered 1 week after the first dose and the third dose, if administered, is administered 1 or 2 weeks after the second dose.

In some embodiments, a method for treating a gastrin-associated tumor and/or cancer of the presently disclosed subject matter comprises administering to a subject in need thereof a first agent that directly or indirectly inhibits one or more biological activities of gastrin in the tumor and/or cancer and a second agent comprising a stimulator of a cellular immune response against the tumor and/or the cancer. As such, in some embodiments the first agent directly or indirectly inhibits one or more biological activities of gastrin in the tumor and/or cancer by providing and/or inducing a humoral immune response against a gastrin peptide, optionally wherein the agent is selected from the group consisting of an anti-gastrin antibody and a gastrin peptide that induces production of neutralizing anti-gastrin antibodies in the subject; and/or comprises a nucleic acid that inhibits expression of a gastrin gene product. Nucleic acids that inhibit expression of a gastrin gene product would be understood by one of ordinary skill in the art after consideration of this disclosure, and examples are discussed herein above.

Anti-gastrin antibodies are known in the art and are described in U.S. Pat. Nos. 5,607,676; 5,609,870; 5,622,702; 5,785,970; 5,866,128; and 6,861,510. See also PCT International Patent Application Publication Nos. WO 2003/005955 and WO 2005/095459. The content of each of these U.S. Patents and PCT International Patent Application Publications is incorporated herein in its entirety. In some embodiments, an anti-gastrin antibody is an antibody directed against an epitope present within gastrin-17 (G17). In some embodiments, the epitope is present within one or more of the amino acid sequences EGPWLEEEEE (SEQ ID NO: 1), EGPWLEEEE (SEQ ID NO: 2), EGPWLEEEEEAY (SEQ ID NO: 3), and EGPWLEEEEE-AYGWMDF (SEQ ID NO: 4).

In some embodiments, administration of a pharmaceutical composition of the presently disclosed subject matter to a subject induces a reduction in and/or prevents the development of fibrosis associated with the pancreatic cancer.

In some embodiments, the presently disclosed treatment methods are designed to inhibit growth and/or survival of a gastrin-associated tumor and/or cancer in a subject. In some embodiments, the presently disclosed methods thus comprise administering to the subject a composition that comprises a first agent comprising a gastrin immunogen, one or more anti-gastrin antibodies, one or more anti-CCK-B receptor antibodies, or any combination thereof; and a second agent comprising a checkpoint inhibitor.

Thus, in some embodiments the presently disclosed subject matter provides uses of the pharmaceutical compositions disclosed herein for the preparation of medicaments to treat gastrin-associated tumors and/or cancers as well as uses of the pharmaceutical compositions disclosed herein to treat gastrin-associated tumors and/or cancers.

In some embodiments, the multi-agent pharmaceutical compositions disclosed herein provide enhanced, more efficacious, and/or more successful treatment of gastrin-associated tumors and/or cancers than would treating a similar subject with the any of the agents individually.

VI.B. Methods for Inducing and/or Enhancing Cellular Immune Responses Against Gastrin-Associated Tumors and/or Cancers The presently disclosed subject matter also provides methods for inducing and/or enhancing cellular immune responses against gastrin-associated tumors and/or cancers in subject. In some embodiments, the methods comprise administering to a subject that has a gastrin-associated tumor or cancer an effective amount of a composition comprising an agent that reduces or inhibits gastrin signaling via CCK-B receptors present on a gastrin-associated tumor or cancer, thereby inducing and/or enhancing a cellular immune response against the subject's gastrin-associated tumor and/or cancer. As used herein, the phrase "inducing and/or enhancing a cellular immune response against a gastrin-associated tumor and/or cancer" and grammatical variants of refers to a circumstance where as a result of administering to a subject that has a gastrin-associated tumor or cancer an effective amount of a composition comprising an agent that reduces or inhibits gastrin signaling via CCK-B receptors present on a gastrin-associated tumor or cancer, a level of a T cell-based immune response is higher in the subject at a relevant time post-administration than would have been present in the subject in the absence of the treatment. Agents that reduce or inhibit gastrin signaling via CCK-B receptors present on a gastrin-associated tumor or cancer include the agents disclosed herein that can interfere with an interaction of a gastrin peptide and a CCK-B receptor, and include but are not limited to gastrin peptides and/or immunogens, anti-gastrin antibodies, anti-CCK-B receptor antibodies, small molecule inhibitors of gastrin/CCK-B signaling, and combinations thereof.

VI.C. Methods for Sensitizing Tumors and/or Cancers to Inducers of Cellular Immune Responses In some embodiments, the presently disclosed subject matter also provides methods for sensitizing tumors and/or cancers associated with gastrin and/or CCK-B receptor signaling in a subject to inducers of cellular immune responses directed against the tumors and/or cancers. As used herein, the phrase "sensitizing tumors and/or cancers associated with gastrin and/or CCK-B receptor signaling in a subject to inducers of cellular immune responses" refers to treatments that result in levels of cellular immune responses in subjects when one or more inducers of a cellular immune response is administered to the subject as compared to levels of cellular immune responses in subjects when one or more inducers of a cellular immune response is administered to the subject in the absence of the treatment.

In some embodiments, the methods comprise administering to a subject a composition comprising a first agent that induces and/or provides an active and/or a passive humoral immune response against a gastrin peptide, and a second agent that induces and/or provides a cellular immune response against the tumor and/or the cancer, or a combination thereof, optionally wherein the first agent and the second agent are individually selected from the group consisting of a gastrin peptide and/or a fragment and/or a derivative thereof that induces a cellular immune response or production of neutralizing anti-gastrin antibodies in the subject and a neutralizing anti-gastrin antibody and/or a fragment and/or derivative thereof and; and/or a composition comprising a nucleic acid that inhibits expression of a gastrin gene product; and/or a composition comprising an agent that blocks the biological function of gastrin at the CCK-B receptor. In some embodiments, the anti-gastrin antibody is an antibody directed against an epitope present within gastrin-17 (G17).

Accordingly, in some embodiments the instant methods for sensitizing tumors and/or cancers associated with gastrin and/or CCK-B receptor signaling in a subject to inducers of cellular immune responses comprises administering to the subject a pharmaceutical composition as disclosed herein in order to induce and/or provide to the subject both an active and/or a passive humoral immune response against a gastrin peptide in the subject as well as to induce and/or provide a cellular immune response against the tumor and/or the cancer.

VI.D. Methods for Preventing, Reducing, and/or Eliminating Fibrosis Associated with Tumors and/or Cancers PC is also characterized by a dense fibrotic environment (Neesse et al., 2011), which helps promote angiogenesis and creates a physical barrier that could inhibit the penetration of chemotherapeutics and immunotherapeutics to the pancreatic tumor site (Templeton & Brentnall, 2013). Disclosed herein is the unexpected and surprising observation that that with PAS administration, optionally in combination with one or more immune checkpoint inhibitors, the fibrotic nature that is a hallmark of PC fibrosis can be reduced. While not wishing to be bound by any particular theory of operation, a reduction in fibrosis can facilitate greater penetration of other drugs, including but not limited to macromolecules like checkpoint mAbs. This could explain why check point inhibitors have to date been characterized by very modest efficacy, perhaps due to lack of penetration of the checkpoint mAbs to PDAC cells. Therefore, an aspect of the presently disclosed subject matter is that PAS plus immune checkpoint inhibitors have anti-PDAC-tumor activity separately when given as monotherapy, but when given as a combination therapy as disclosed herein, they have much greater activity.

Novel and innovative drug combinations with diverse but complementary or even synergistic mechanisms of action are provided in accordance with the presently disclosed subject matter to address the inherently fibrotic nature of PDAC and to be beneficial to allow greater access to the tumor environment of large monoclonal antibodies (mAbs), such as but not limited to anti-immune checkpoint inhibitor mAbs. While not wishing to be bound by any particular theory of operation, PAS plus immune checkpoint inhibitors when administered together as part of a combination therapy can provide a synergistic effect to make tumors more accessible to chemotherapeutics and immune checkpoint inhibitor drugs by reducing the fibrosis associated with PDAC, thereby allowing anti-tumor therapeutics to target the interaction of PD-1 and PD-L1 in order to induce a cellular immune response against a gastrin-associated tumor.

Treatment with PAS results in a humoral immunological response (i.e., an antibody response) to the autocrine and paracrine tumor/cancer growth factor gastrin. In so doing, PAS affects the tumor/cancer (e.g., PDAC) phenotype by affecting cell proliferation, apoptosis, angiogenesis, invasion, and metastasis. As disclosed herein, PAS is also effective in decreasing fibrosis associated with PDAC. While not wishing to be bound by any particular theory of operation, this is believed to enhance the ability of large molecules, such as but not limited to immune checkpoint inhibitory mAbs, to gain greater access to the pancreatic tumor site, which in turn would be expected to promote a much greater cellular immune effect. PAS also results in a cellular immune response to gastrin. Thus, disclosed herein are methods for treating tumors and/or cancers by PAS administration in conjunction with the administration of immune checkpoint inhibitors such as anti-PD-1, anti-PD-L1, and/or anti-CTLA-4 mAbs to address the inherent fibrotic as well as recalcitrant nature of PDAC in resistance to therapeutic agents that need access to the tumor for efficacy.

Therefore, in some embodiments the presently disclosed subject matter provides methods for preventing, reducing, and/or eliminating formation of fibrosis associated with a tumor and/or a cancer, optionally pancreatic cancer, by contacting cells of the tumor and/or the cancer with an agent that directly or indirectly inhibits one or more biological activities of gastrin in the tumor and/or cancer. Agents that directly or indirectly inhibit one or more biological activities of gastrin are disclosed herein above, and include agents that provide and/or induce humoral immune responses against gastrin peptides (such as but not limited to anti-gastrin antibodies, and/or fragments and/or derivatives thereof), and gastrin peptides that induce production of neutralizing anti-gastrin antibodies in the subject; inhibitory nucleic acids that inhibit expression of gastrin gene products; small molecule compounds that block the function of the gastrin hormone, and any combination thereof. In some embodiments, the anti-gastrin antibodies comprise an antibody directed against an epitope present within gastrin-17 (G17), which epitope is in some embodiments present within one or more of the amino acid sequences EGPWLEEEEE (SEQ ID NO: 1), EGPWLEEEE (SEQ ID NO: 2), EGPWLEEEEEAY (SEQ ID NO: 3), and EGPWLEEEEEAYGWMDF (SEQ ID NO: 4).

As with other immunogenic forms of gastrin and gastrin peptides disclosed herein, in some embodiments the gastrin peptides are conjugated to an immunogenic carrier, optionally an immunogenic carrier selected from the group consisting of diphtheria toxoid, tetanus toxoid, keyhole limpet hemocyanin, and bovine serum albumin.

In some embodiments, the methods for preventing, reducing, and/or eliminating formation of fibrosis associated with a tumor and/or a cancer, optionally pancreatic cancer further comprise contacting the tumor and/or the cancer with a second agent comprising a stimulator of a cellular immune response against the tumor and/or the cancer. Exemplary stimulators of cellular immune responses include immune checkpoint inhibitors such as those that inhibit a biological activity of a target polypeptide selected from the group consisting of cytotoxic T-lymphocyte antigen 4 (CTLA4), programmed cell death-1 receptor (PD-1), and programmed cell death 1 receptor ligand (PD-L1), including but not limited to Ipilimumab, Tremelimumab, Nivolumab, Pidilizumab, Pembrolizumab, AMP514, AUNP12, BMS-936559/MDX-1105, Atezolizumab, MPDL3280A, RG7446, RO5541267, MEDI4736, and Avelumab.

In some embodiments, the tumor and/or cancer for which preventing, reducing, and/or eliminating the formation of fibrosis therein is pancreatic cancer.

VI.E. Methods for Modulating T Cell Subpopulations in Subjects and Tumors Present Therein As disclosed herein, administration of the pharmaceutical compositions of the presently disclosed subject matter to subjects that have gastrin-associated tumors and/or cancers was observed to modify both the circulating T cell subpopulations present in subjects treated with gastrin-associated tumors and/or cancers as well as the T cell subpopulations present within the tumors and/or cancers per se.

In some embodiments, administration of the pharmaceutical compositions of the presently disclosed subject matter to subjects that have gastrin-associated tumors and/or cancers results in an enhancement of the number of $CD8^+$ tumor infiltrating lymphocytes (TILs) present in gastrin-associated tumors and/or cancers. It is recognized in the art that that TILs have anti-tumor and anti-cancer activity, and thus increasing the number of TILs in a tumor and/or a cancer can result in greater anti-tumor and/or anti-cancer efficacy of various treatment strategies with either the pharmaceutical compositions of the presently disclosed subject matter alone or in combination with other front-line an/d or secondary treatments.

In some embodiments, administration of the pharmaceutical compositions of the presently disclosed subject matter to subjects that have gastrin-associated tumors and/or cancers results in a reduction in the number of $FoxP3^+$ inhibitory T-regulatory cells ($T_{regs}$) present in gastrin-associated tumors and/or cancers. It is recognized in the art that that $T_{regs}$ have immunosuppressive activity, particularly tumor- and cancer-specific immunosuppressive activity, and thus reducing the number of $FoxP3^+$ inhibitory $T_{regs}$ in a tumor and/or a cancer can result in greater anti-tumor and/or anti-cancer efficacy of various treatment strategies with either the pharmaceutical compositions of the presently disclosed subject matter alone or in combination with other front-line an/d or secondary treatments. In some embodiments, reducing the number of $FoxP3^+$ inhibitory $T_{regs}$ in a tumor and/or a cancer can result in greater efficacy of front-line chemotherapeutics.

In some embodiments, administration of the pharmaceutical compositions of the presently disclosed subject matter to subjects that have gastrin-associated tumors and/or cancers results in an increase in anti-gastrin $T_{EMRA}$ cells in the subjects. $T_{EMRA}$ cells are effector memory T cells that are found in the peripheral circulation and tissues. $T_{EMRA}$ cells appear to have a sentinel activity in that they might be involved in recognizing metastases. As such, increasing anti-gastrin $T_{EMRA}$ cells in subjects could prevent, reduce, and/or eliminate metastasis associated with gastrin-associated tumors and/or cancers. Therefore, in some embodiments the presently disclosed subject matter relates to methods for increasing $T_{EMRA}$ cells that recognize gastrin-associated tumor and/or cancer antigens and cells expressing the same by treating subjects with the pharmaceutical compositions disclosed herein.

Summarily, in some embodiments the presently disclosed subject matter relates to uses of the presently disclosed compositions comprising immune checkpoint inhibitors and gastrin immunogens to treat gastrin-associated tumors and/or cancers, either alone as a front-line therapy, in combination with other front-line therapies, or in combination with any other therapy that would be appropriate for a subject who has a gastrin-associated tumor and/or cancer.

VII. Conclusion

The presently disclosed subject matter thus relates in some embodiments to combination therapies for the treatment of cancer using a combination of methods that individually or together generate both a humoral antibody immune response (using, for example, the gastrin cancer vaccine PAS) and a cellular T cell immune response (using, for example, the gastrin cancer vaccine PAS or an immune checkpoint inhibitor). More particularly, unexpected additive and/or synergistic efficacies in treating human and animal gastrointestinal tumors using the instantly described combination of drug classes that generate humoral and cellular immune anti-tumor responses in combination with cellular immune anti-tumor effects are described.

More particularly, the presently disclosed subject matter relates in some embodiments to using specific combinations of drugs that (i) induce humoral B cell immune responses to a tumor growth factor or circulating tumor growth factor; and (ii) induce and/or enhance cellular immune responses (i.e., anti-tumor and/or cancer T cell responses) directed against the tumor and/or cancer to elicit a cytotoxic T lymphocyte response.

As such, in some embodiments disclosed herein are methods for treating human and animal tumors and cancers using a combination of a gastrin cancer vaccine in combination with a second drug that overcomes immune checkpoint failure. Thus, in some embodiments the presently disclosed subject matter relates to treating specific human cancers with a cancer vaccine directed at eliciting a B cell and/or antibody immune response and a cellular immune response to the active form of the growth factor gastrin, with the unexpected observation that this vaccine treatment also resulted in making the tumor more responsive to treatment with an immune checkpoint inhibitor, thus creating an unexpected, additive, or even synergistic combination therapeutic effect that enhanced anti-tumor efficacy.

Additionally, the pharmaceutical compositions of the presently disclosed subject matter can be employed for preventing, reducing, and/or eliminating metastasis of a gastrin-associated tumor or cancer by administering to a subject having a gastrin-associated tumor or cancer an amount of the pharmaceutical composition of any one of claims 1-13 sufficient to enhance the number of CD8+ tumor infiltrating lymphocytes.

The use of claim 104, wherein the administering results in improves survival of the subject, reduced tumor growth, and/or enhanced efficacy of a chemotherapeutic agent and/or an immune checkpoint therapy in the subject as compared to that which would have occurred had the pharmaceutical composition not been administered.

Use of the pharmaceutical composition of any one of claims 1-13 for preventing, reducing, and/or eliminating metastasis of a gastrin-associated tumor or cancer by administering to a subject having a gastrin-associated tumor or cancer an amount of the pharmaceutical composition of any one of claims 1-13 sufficient to reduce the number of FoxP3+ inhibitory T-regulatory cells.

EXAMPLES

The following EXAMPLES provide illustrative embodiments. In light of the present disclosure and the general level of skill in the art, those of skill will appreciate that the following EXAMPLES are intended to be exemplary only and that numerous changes, modifications, and alterations can be employed without departing from the scope of the presently disclosed subject matter.

Materials and Methods for the Examples

Cell Line: Murine mT3 pancreatic cancer cells were obtained from the laboratory of Dr. David Tuveson (Cold Spring Harbor Laboratories, Cold Spring Harbor, New York, United States of America; see also Boj et al., 2015). These cells have been shown to express the CCK-B receptor and produce gastrin, and were used as the tumor model. These cells produce tumors in syngeneic C57BL/6 mice (Smith et al., 2018).

Study Design: All animal studies were performed in an ethical fashion under a protocol approved by the Institutional Animal Care and Use Committee (IACUC) of Georgetown University (Washington, D.C., United States of America). Forty male (6 weeks old) C57BL-6 mice were injected with 500,000 cells subcutaneously into the flank. On the $6^{th}$ day after inoculation 100% of the mice had a palpable tumor and were allocated into one of four (4) groups of n=10 mice each so that the baseline tumor volume was equal in all groups. The Groups were as follows:

1. PBS Control (PBS)
2. PAS 100 µg (PAS100)
3. PD-1 Ab 150 µg (PD-1)
4. PD-1 Ab (150 µg)+PAS 100 µg (PD-1+PAS100)

One week (7 days) after the mT3 cells were injected, non-control Groups of mice received administration of patent applications and/or PD-1 Ab as follows: if the mice were in a group that was to receive PAS, the PAS was injected starting at the time of randomization (baseline time=0) as an i.p. injection in 100 µl and again at week 1 and at week 3. PD-1 antibody (Bio X cell, West Lebanon, New Hampshire, United States of America) was given to appropriate mice at a dose of 150 µg i.p. five times during the study at t=0, 4, 8, 15, and 21 days). Control mice received PBS on the same days that PAS was administered. Tumor volumes were measured weekly by calipers and calculated as $L \times (w)^2 \times 0.5$.

Histology: After 31 days of growth the mice were ethically euthanized by $CO_2$ asphyxiation and cervical dislocation. Mice were weighed, pancreatic tumors were excised, and they were weighed. The tumors were divided and half of the tumor was fixed in 4% paraffin in formaldehyde for histology and half was flash frozen in liquid nitrogen. Tumor-associated fibrosis was assessed with Masson's trichrome staining. Analysis of Masson's trichrome was done by a technician blinded to the treatment using ImageJ image processing and analysis software (developed by Wayne Rasband of the United States National Institutes of Health (NIH), Bethesda, Maryland, United States of America; available through the website of the NIH).

For immunohistochemistry, tumors were sectioned from paraffin embedded blocks (10 µm) and fixed on slides. Tumor sections were stained with either anti-CD8 antibodies (1:75; EBIOSCIENCE™, San Diego, California, United States of America); or anti-Foxp3 antibodies (1:30; EBIOSCIENCE™). Immunoreactive cells were counted manually.

Spleen T-cell isolation. The spleen from each animal was removed, weighed, and placed in a 60 mm dish containing 5 ml RPMI1640 medium. The spleens were mechanically chopped using a razor blade. The medium containing the spleen tissue was filtered through a 100 µM cell strainer to a 50 ml tube and rinsed with medium a few times until the final volume was 40 ml. The spleen tissue was then filtered again using a 40 µM cell strainer to a 50 ml tube, and centrifuged to pellet down the cells at 1500 rpm for 5 minutes at 4° C. The supernatant was removed and the cell pellet resuspended in 40 ml PBS before the cells were repelleted by centrifugation at 1500 rpm for 5 minutes at 4° C. The supernatant was discarded, the cell pellet was resuspended in 3 ml Washing buffer (PBS with 2 mM EDTA and 0.5% bovine serum albumin), and then slowly added on the top of 5 ml Ficoll medium in a 15 ml tube. After centrifugation at 2100 rpm for 20 minutes with deceleration set to zero, the lymphocytes were collected from the white layer between buffer and the Ficoll. The lymphocytes were washed an additional two times, resuspended in medium, and counted.

Flow cytometry. One million lymphocytes were added to a 5 ml clear tube (Catalogue #352054; BD Falcon, Bedford, Massachusetts, United States of America), volumes were equalized with PBS, and the cells were pelleted at 1500 rpm for 5 minutes. After washing with PBS, 50 µl of pre-diluted ZOMBIE NIR™ brand fixable viability solution (BIOLEGEND®, San Diego, California, United States of America) was added to the cells, which were then incubated at room temperature in the dark for 20 minutes. The cells were washed and then blocked by adding 5 µl Purified Rat Anti-Mouse CD16/CD32 (Mouse BD Fc BLOCK™ brand reagent; BD Biosciences, San Jose, California, United States of America) and incubating for 20 minutes.

The antibodies listed in Table 1 were reacted to the lymphocytes and flow cytometry performed using a FACSARIA™ IIu brand cell sorter (BD Biosciences) with 375 nm, 405 nm, 488 nm and 633 nm laser lines.

TABLE 1

Antibodies Employed for T-cell Staining for Flow Cytometry

| Fluorescent Label | Antigen | Supplier |
| --- | --- | --- |
| PE | CD4 | EBIOSCIENCE ™ (San Diego, California, United States of America) |
| Fitc | CD3 | BIOLEGEND ® (San Diego, California, United States of America) |
| PE/Dazzle 594 | CD62L | BIOLEGEND ® |
| eFlour 450/BV421 | CD8a | EBIOSCIENCE ™ |
| APC | CD25 | BIOLEGEND ® |
| BV 605 | CD69 | BIOLEGEND ® |
| BV 510 | CD44 | BIOLEGEND ® |
| BV 650 | CD45 | BIOLEGEND ® |

For re-stimulation. 1 or 2 million isolated and washed lymphocytes were added to each well of a 6-well plate for two duplicate plates, and the volume was brought to the same for each (2 or 3 ml). Brefeldin A solution (BIOLEGEND®, 1000X Catalogue No. 420601) was added at 1 µl/ml to each well. 1 µM gastrin-14 (Sigma Aldrich Catalogue No. SCP0152, having the amino acid sequence pEGPWLEEEEEAYGW; SEQ ID NO: 5) was added to each well at 1 µl/ml for one plate for a final gastrin concentration of 1 nM. The other duplicate plate was not treated with gastrin-14 and served as a control. The 6-well plates were placed in the cell culture incubator at 37° C. for 6 hours. The cells were then removed, washed, and permeabilized using an Intracellular Fixation & Permeabilization Buffer Set (EBIOSCIENCE™ Catalogue No. 88-8824-00). A cytokine antibody master mix including the four (4) antibodies listed in Table 2 was added (4 antibodies for 8 samples, so 10 µl of each antibody to make the mastermix), and incubated at 4° C. overnight.

TABLE 2

Antibodies Employed for Re-stimulation Analyses

| Fluorescent Label | Target | Supplier |
| --- | --- | --- |
| PE/Dazzle594 | TNFα | EBIOSCIENCE ™ |
| APC | IFNγ | EBIOSCIENCE ™ |
| PE | Granzyme-B | EBIOSCIENCE ™ |
| FITC | Perforin | EBIOSCIENCE ™ |

Flow cytometry was performed to analyze for cytokines in cells that were re-stimulated with gastrin or with PBS. Analysis of flow cytometry data was done using FCSExpress-6 software (De Novo Software, Glendale, California, United States of America).

Example 1

Producing Tumors in Mice

To determine whether PAS treatment induced both a humoral and a cellular immune response and provided a synergistic effect on immune checkpoint antibody therapy, tumors were generated in immune competent mice (e.g., C57BL/6 mice that were syngeneic with murine mT3 pancreatic cancer cells) by introducing $5 \times 10^5$ murine mT3 pancreatic cancer cells in 0.1 ml PBS subcutaneously into the flank. After allowing for one week for the tumors to become established, mice were treated with PAS and one or more immune checkpoint inhibitors as depicted in FIG. 1.

Animals were treated starting one week after mT3 pancreatic cancer cell inoculation as this timeframe ensured that all animals in the study had a palpable subcutaneous tumor, and that treatment did not interfere with tumor initiation. The primary end points were tumor growth and survival. Growth of tumors was measured weekly with calipers and the volumes of the tumors were calculated as $L \times W^2 \times 0.5$. Tumors were excised and examined histologically by immunohistochemistry for immune cells, including but not limited to tumor-infiltrating lymphocytes (TILs), and T Regulatory cells ($T_{regs}$). Tumors were also examined for the presence and extent of fibrosis development typically associated with PDAC. Spleens were removed and T-cells isolated and re-stimulated with gastrin. The cells were labeled with a panel of relevant antibodies for cytokines and characterized by flow cytometry.

Figure 2:
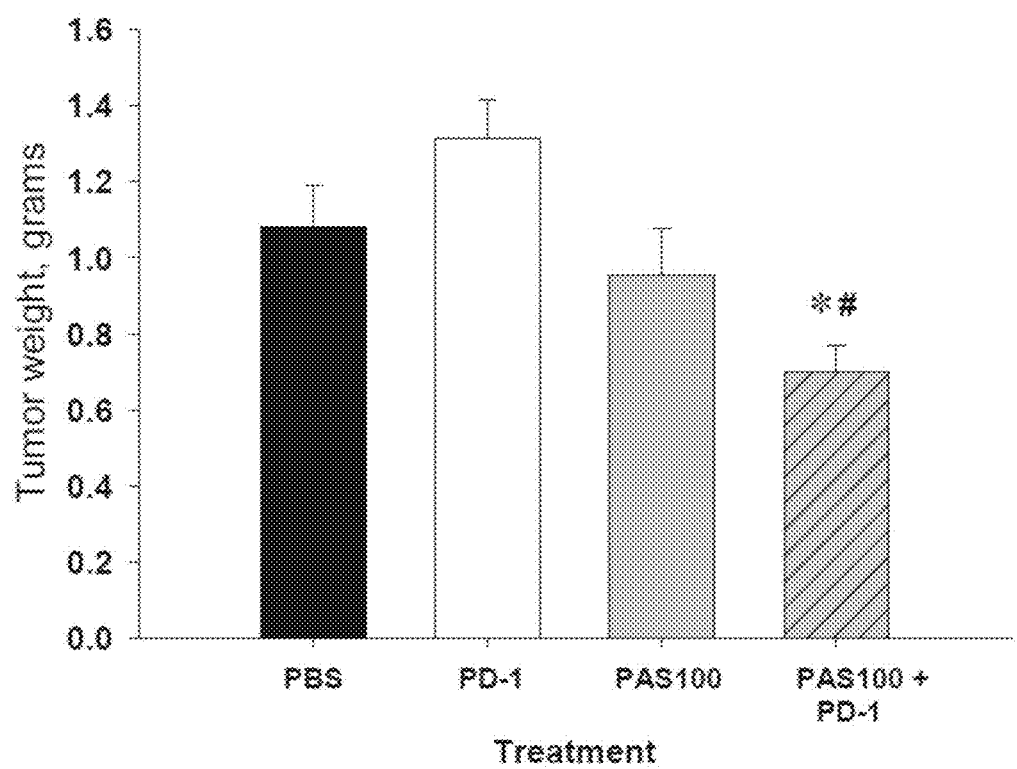
FIG. 2 is a bar graph showing mean tumor weights in grams in mT3-bearing mice following treatment with control (phosphate-buffered saline only; PBS), PAS alone (100 μg per administration; PAS100), PD-1 Ab alone (150 μg per administration; PD-1), or the combination of PAS (100 μg per administration) and PD-1 Ab (150 μg per administration; PAS100+PD-1). NS: $p \geq 0.05$ (i.e., not significant); $*p<0.05$ compared to PBS and compared to PAS100; $^\#p=0.0017$ as compared to PD-1. Error bars are ±SEM.

Each experiment employed 40 mice (n=10 per group; see FIG. 1), which were implanted with $5 \times 10^5$ pancreatic murine cancer cells. Groups of immune competent syngeneic mice bearing mT3 murine pancreatic tumors were treated with PBS (negative control), PAS monotherapy (100 µg per administration at 0, 1, 2, and 3 weeks after tumor cell inoculation), an anti-PD-1 antibody (PD1-1 Ab; Bio X cell, West Lebanon, New Hampshire, United States of America) as an immune checkpoint inhibitor (150 µg per administration at 0, 4, 8, 15, and 21 days after the first PAS vaccination), or a combination of both PAS vaccination (100 µg per administration at 0, 1, 2, and 3 weeks after tumor cell inoculation) and the immune checkpoint inhibitor (150 µg per administration at 0, 4, 8, 15, and 21 days after the first PAS vaccination). The immune checkpoint blockade antibody specific for programmed cell death protein 1 (PD1-1 Ab; Bio X cell, West Lebanon, New Hampshire, United States of America) was administered intraperitoneally. The data are summarized in Table 3 below and in FIG. 2.

TABLE 3

Mean Mouse Body Weight in Each Treatment Group

| Treatment Group | Mean Weight (g ± SEM) | p value |
| --- | --- | --- |
| PBS (negative control) | 27.500 ± 0.563 | — |
| PD-1 | 27.333 ± 0.645 | NS |
| PAS100 alone | 27.400 ± 0.499 | NS |
| PD-1 + PAS100 | 28.000 ± 0.577 | NS |

NS: not significant

There were no statistical differences in final tumor weights in grams between the PBS control mice and the weights of the tumors from mice in both the PD-1 and PAS100-treated groups. In contrast, the mice treated with the combination of PD-1 and PAS100 had significantly smaller tumors compared to PBS (p=0.014) and PD-1 controls (p=0.0017). Furthermore, the combination therapy with PD-1 and PAS100 resulted in tumors that were also significantly smaller than PAS100 monotherapy (p<0.05).

Example 2

Analyses of $T_{EMRA}$ CD4$^-$/CD8$^-$ Cells in the CD3 Terminally Differentiated T Cell Subpopulation Tumors were induced in mice as set forth in EXAMPLE 1. T lymphocytes were isolated from spleen peripheral blood mononuclear cells (PBMCs) that were isolated from mice that had been treated with PBS, PD-1 Ab, PAS100, or PAS100+PD-1 Ab. Various subpopulations of T cells were identified by flow cytometry using the antibodies listed in Table 1. In particular, a first T cell subpopulation was isolated that was CD3$^+$/CD4$^-$/CD8$^-$, and from this subpopulation a further subpopulation representing $T_{EMRA}$ cells that were CD3$^+$/CD4$^-$/CD8$^-$/CD44$^-$/CD62L$^-$ was isolated. The percentages and proportions of these various subpopulations present in mice that had been treated with PBS, PD-1 Ab, PAS100, or PAS100+PD-1 Ab were determined, and the results are presented in FIGS. 3A and 3B.

Figure 3A:
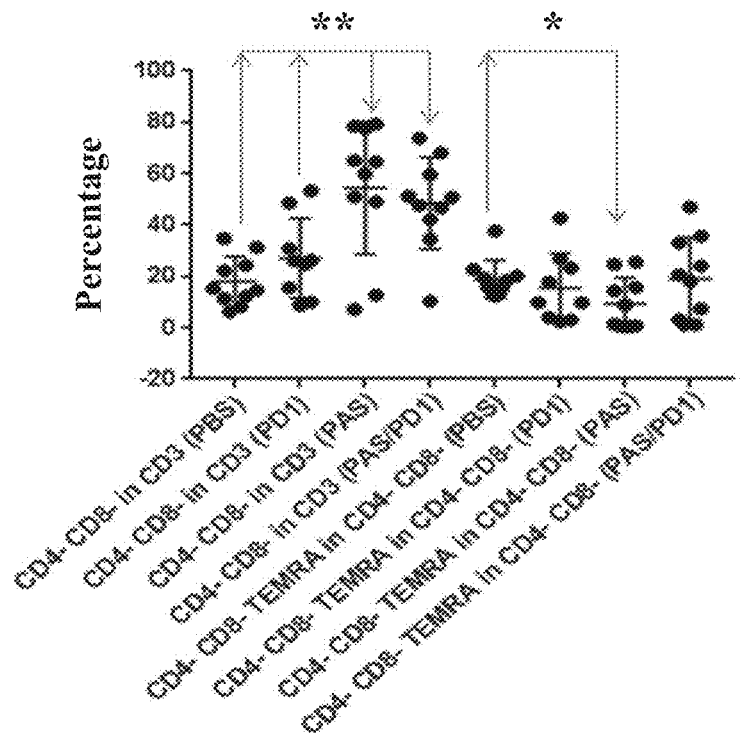
FIGS. 3A and 3B are a series of plots of $CD4^-/CD8^-$ and $CD4^-/CD8^-$ $T_{EMRA}$ cells present in CD3 terminally differentiated T cells after treatment with PBS, PD-1 Ab alone (150 μg per administration; PD1), PAS alone (100 μg per administration; PAS), or the combination of PAS (100 μg per administration) and PD-1 Ab (150 μg per administration; PAS/PD1).
Figure 3B:
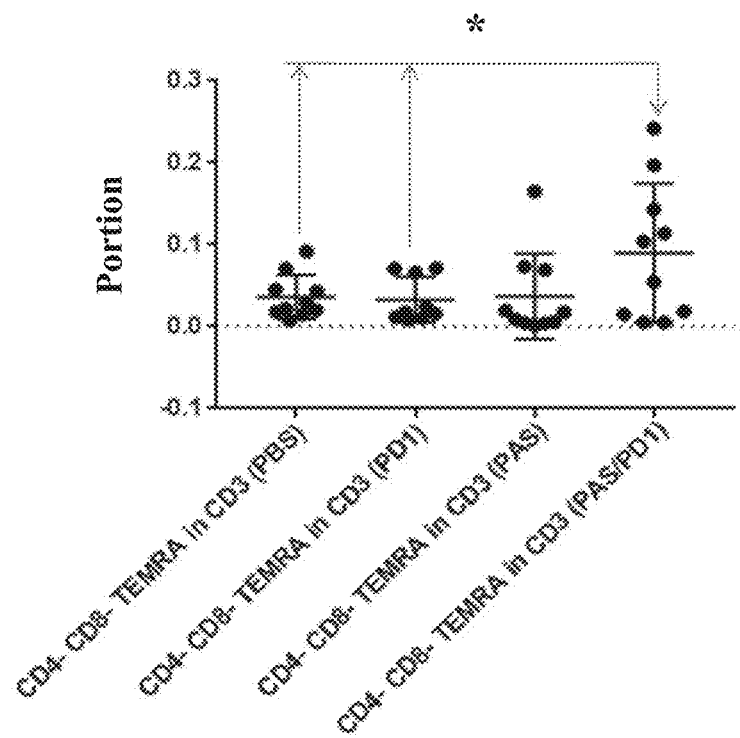

FIG. 3A shows the percentage of $T_{EMRA}$ cells (CD3$^+$/CD4$^-$/CD8$^-$/CD44$^-$/CD62L$^-$) in CD3$^+$ T cells in mice treated with PBS, PD-1 Ab, PAS100, or PAS100/PD-1. FIG. 3B shows the proportion of CD3$^+$/CD4$^-$/CD8$^-$ cells in each treatment group that were $T_{EMRA}$ cells.

The most significant differences among the treatment groups were that PAS100 had lower CD4$^-$/CD8$^-$ $T_{EMRA}$ cells than that of PBS, whereas PAS100+PD-1 treatment resulted in similar CD4$^-$/CD8$^-$ $T_{EMRA}$ cells as compared to that of PBS. The portion of $T_{EMRA}$ cells (CD3$^+$/CD4$^-$/CD8$^-$/CD44$^-$/CD62L$^-$) in T cells from mice treated with PAS100/PD1 was over 2-fold higher than that from mice treated with PBS or PAS100 alone, suggesting that $T_{EMRA}$ cells (CD3$^+$/CD4$^-$/CD8$^-$/CD44$^-$/CD62L$^-$) were good for defending against and fighting gastrin-associated tumors and cancers.

Example 3

Cytokine Activation Assay with PAS100

T lymphocytes were isolated from spleen peripheral blood mononuclear cells (PBMCs) that were isolated from mice that had been treated with PAS100. These cells were evaluated by flow cytometry to determine if they were indeed activated T-cells by cytokine activation to Interferon-γ (INFG), Granzyme-B (granzyme), Perforin, and tumor necrosis factor-α (TNFa). The results are provided in FIGS. 4A and 4B.

Figure 4A:
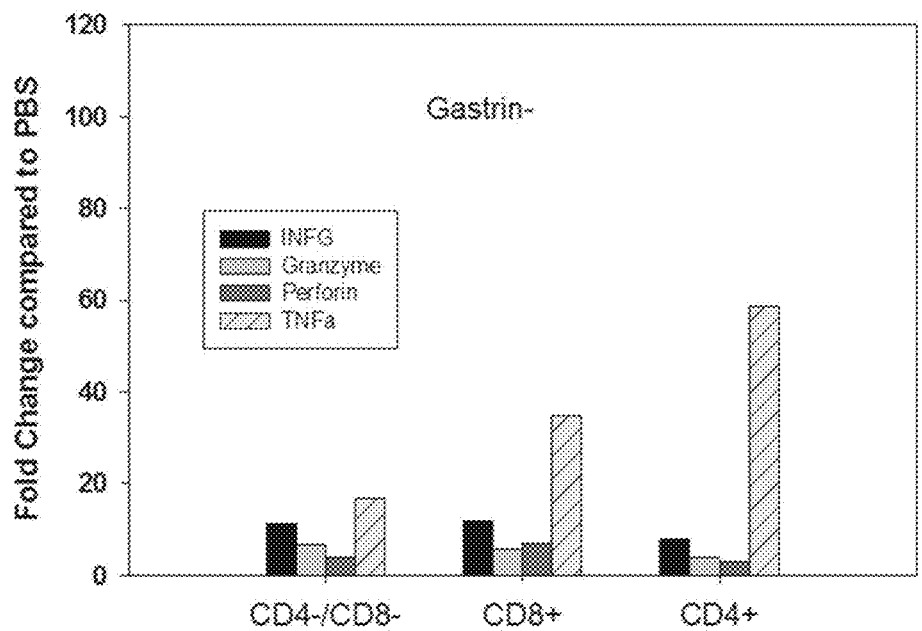
FIGS. 4A and 4B are a series of bar graphs summarizing a cytokine activation assay with respect to TNFα, Granzyme B, Perforin, and INFγ in various T cell subpopulations without (FIG. 4A) and with (FIG. 4B) re-stimulation with gastrin after treatment with PAS100.
Figure 4B:
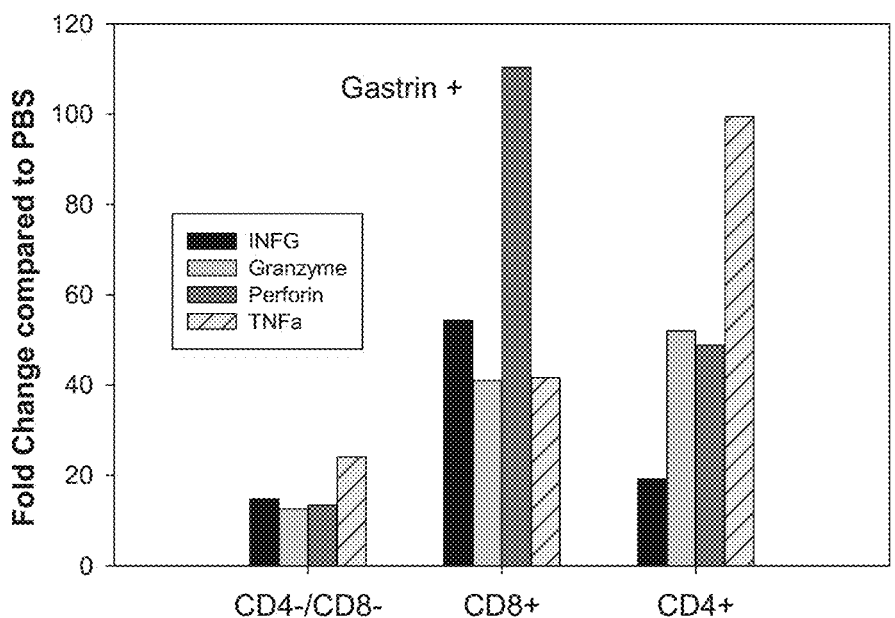

FIG. 4A shows that the T cells isolated from mice treated with PAS100 were indeed activated. When these same cells were re-stimulated with gastrin in culture for 6 hours (see FIG. 4B), they were re-stimulated and released more cytokines, confirming that vaccination with PAS100 stimulated T cells and further that these T cells specifically reacted to gastrin.

Example 4

Comparison of PAS100 to Combination Therapy with PAS & PD-1

T lymphocytes were isolated from spleen PBMC isolated from mice that had been treated with PAS100 or a combination of PAS100 and PD-1. Ccells were evaluated by flow cytometry to determine if they were indeed activated T cells by cytokine activation to Interferon-γ (INFG), Granzyme-B (granzyme), Perforin, and tumor necrosis factor-α (TNFa). The results are provided in FIGS. 5A and 5B.

Figure 5A:
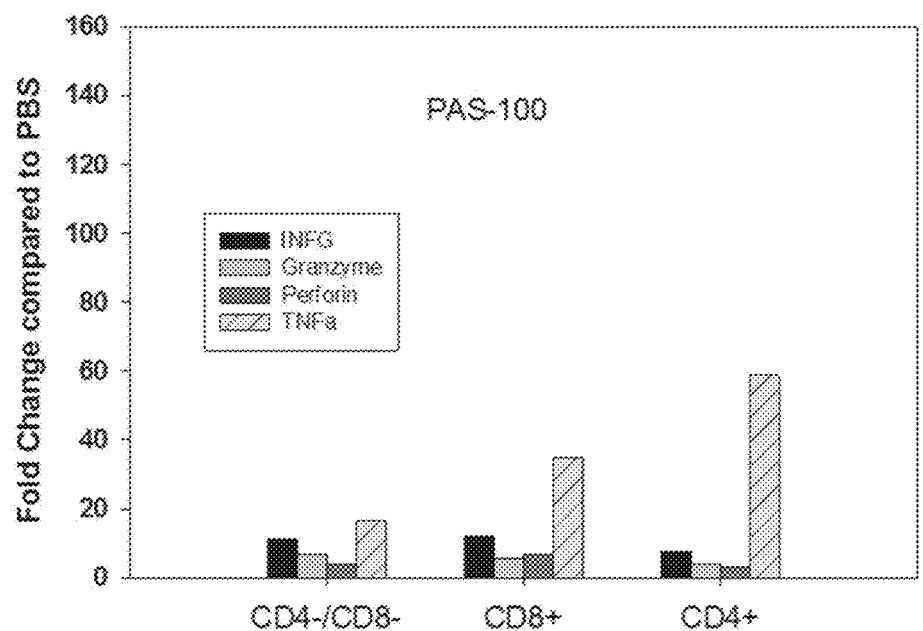
FIGS. 5A and 5B are a series of bar graphs comparing cytokine release with respect to TNFα, Granzyme B, Perforin, and INFγ in CD4−/CD8− (left group in each Figure), CD8+ (middle group in each Figure), and CD4+ (right group in each Figure) T cell subpopulations treated with PAS100 monotherapy (FIG. 5A) or PAS100+PD-1 combination therapy (FIG. 5B). Activated T lymphocytes released increased cytokines compared to lymphocytes from PBS treated mice. The lymphocytes from the combination treated mice released markedly higher levels of cytokines, suggesting that the combination therapy was better at stimulating activated T cells. TNFα in particular was increased greater than 2-fold with the PAS+PD-1 Ab combination therapy. Black bars: INFγ. Light gray bars: Granzyme B. Dark gray bars: Perforin. Hatched gray bars: TNFα.
Figure 5B:
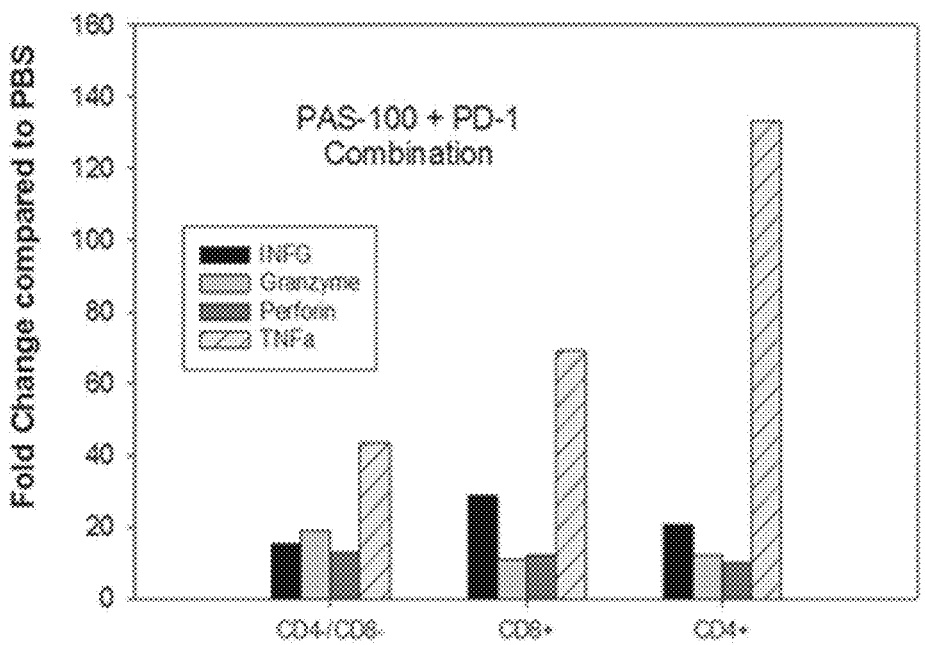

Activated T lymphocytes from mice treated with PAS100 alone released increased cytokines compared to lymphocytes from PBS treated mice (see FIG. 5A). The lymphocytes from the combination treated mice, however, released markedly more cytokines (see FIG. 5B), suggesting that the combination therapy was better at stimulating activated T cells. TNFα in particular was increased greater than 2-fold with the PAS100+PD-1 Ab combination therapy as compared to treatment with PAS100 alone (compare FIGS. 5A and 5B).

Example 5

Analysis of the Effect of PD-1 Monotherapy, PAS100 Monotherapy, and PD-1+PAS100 Combination Therapy on Fibrosis Tumors from mice treated with PBS, PD-1 alone, PAS100, or PAS100+PD-1 were fixed in 4% paraformaldehyde, paraffin embedded, and 8 μm sections were cut and mounted. Tissue sections were stained for fibrosis with Masson's trichrome.

Figure 6A:
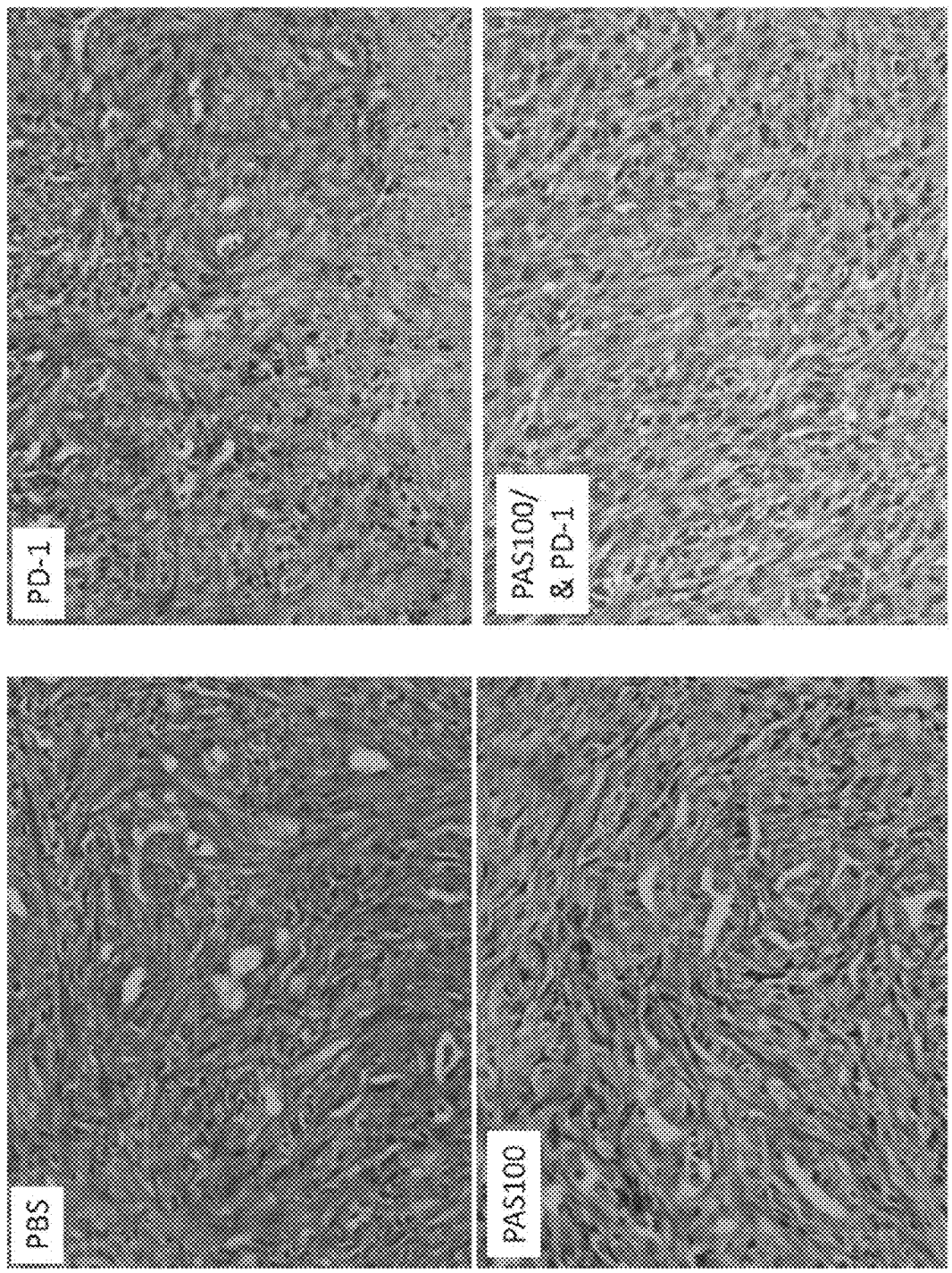
FIGS. 6A and 6B show the results of PBS control, PD-1 monotherapy, PAS100 monotherapy, and PAS100 & PD-1 combination therapy on the development of fibrosis in mT3 pancreatic cancer cell tumors in mice.
Figure 6B:
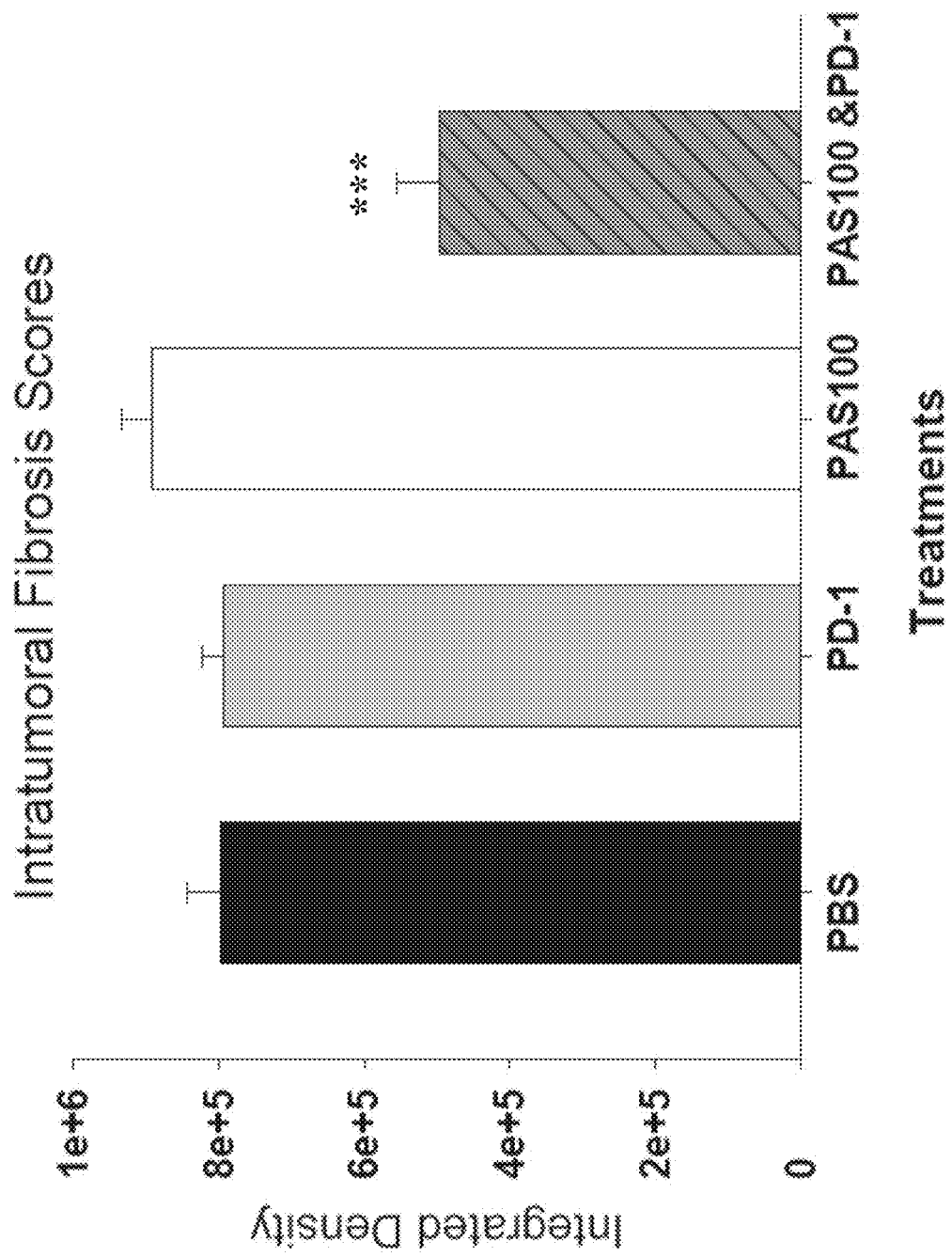

Representative sections stained with Masson's trichrome are shown in FIG. 6A. Fibrosis quantitative scores were analyzed by a computer program using ImageJ image processing and analysis software, and the results are presented in FIG. 6B. Of note is that whereas the integrated density of the tumors treated with PD-1 monotherapy and PAS100 monotherapy were insignificantly different the negative control PBS treatment, the PAS+PD-1 Ab combination therapy resulted in a decrease in density (and hence fibrosis) that was statistically significant as compared to PBS alone (p<0.005) and also PAS100 alone (p<0.001).

Example 6

Analysis of the Effect of PD-1 Monotherapy, PAS100 Monotherapy, and PD-1+PAS100 Combination Therapy on CD8$^+$ T Cell Infiltration Tumors were fixed in 4% paraformaldehyde, paraffin embedded, and 8 μm sections were cut and mounted. CD8$^+$ lymphocytes were stained in the tumor microenvironment with CD8 antibodies (1:75 titer; EBIOSCIENCE™, San Diego, California, U1SA) and CD8$^+$ cells were manually counted in a blinded fashion. The results are presented in FIGS. 7A and 7B.

Figure 7A:
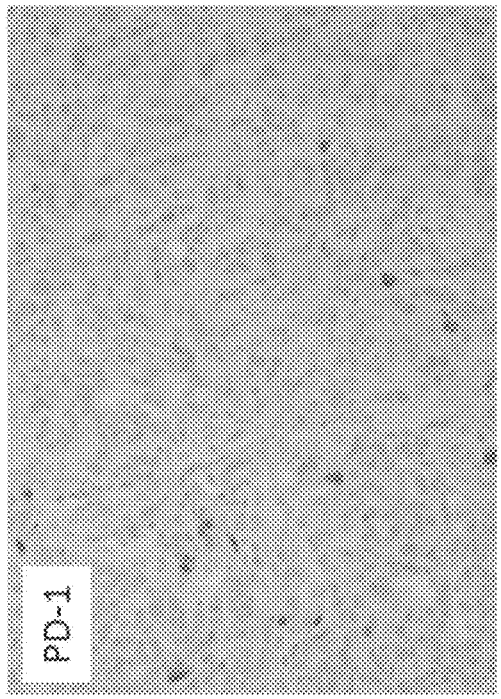
FIGS. 7A and 7B show the results of PBS control, PD-1 monotherapy, PAS100 monotherapy, and PAS100 & PD-1 combination therapy on infiltration of CD8+ cells into mT3 pancreatic cancer cell tumors in mice.
Figure 7A:
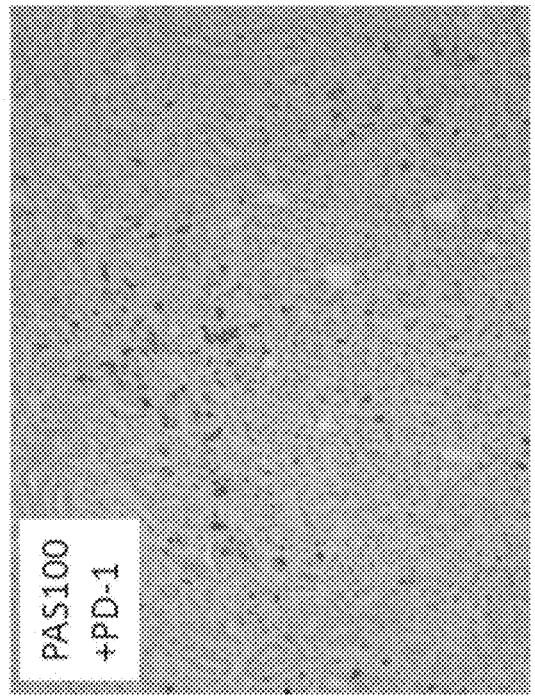
Figure 7A:
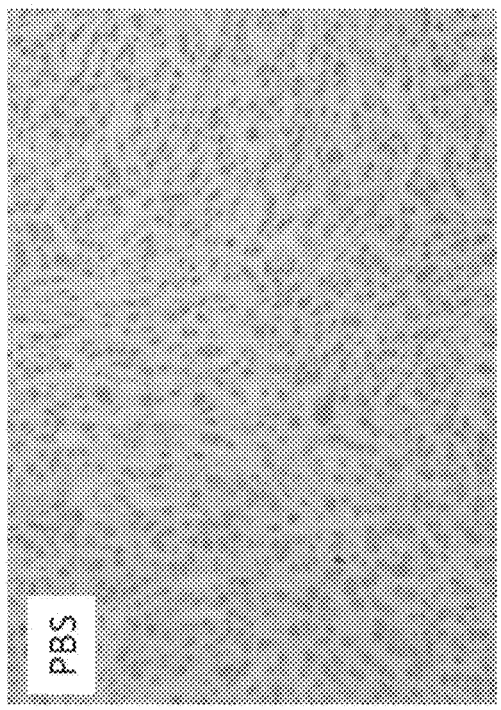
Figure 7A:
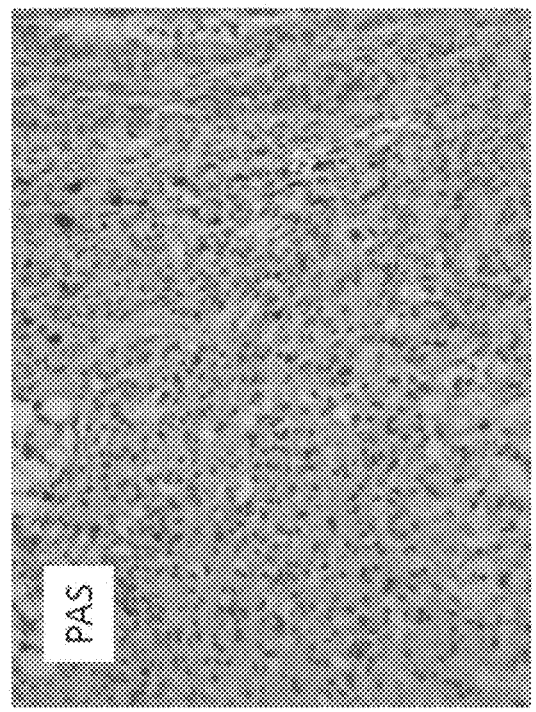
Figure 7B:
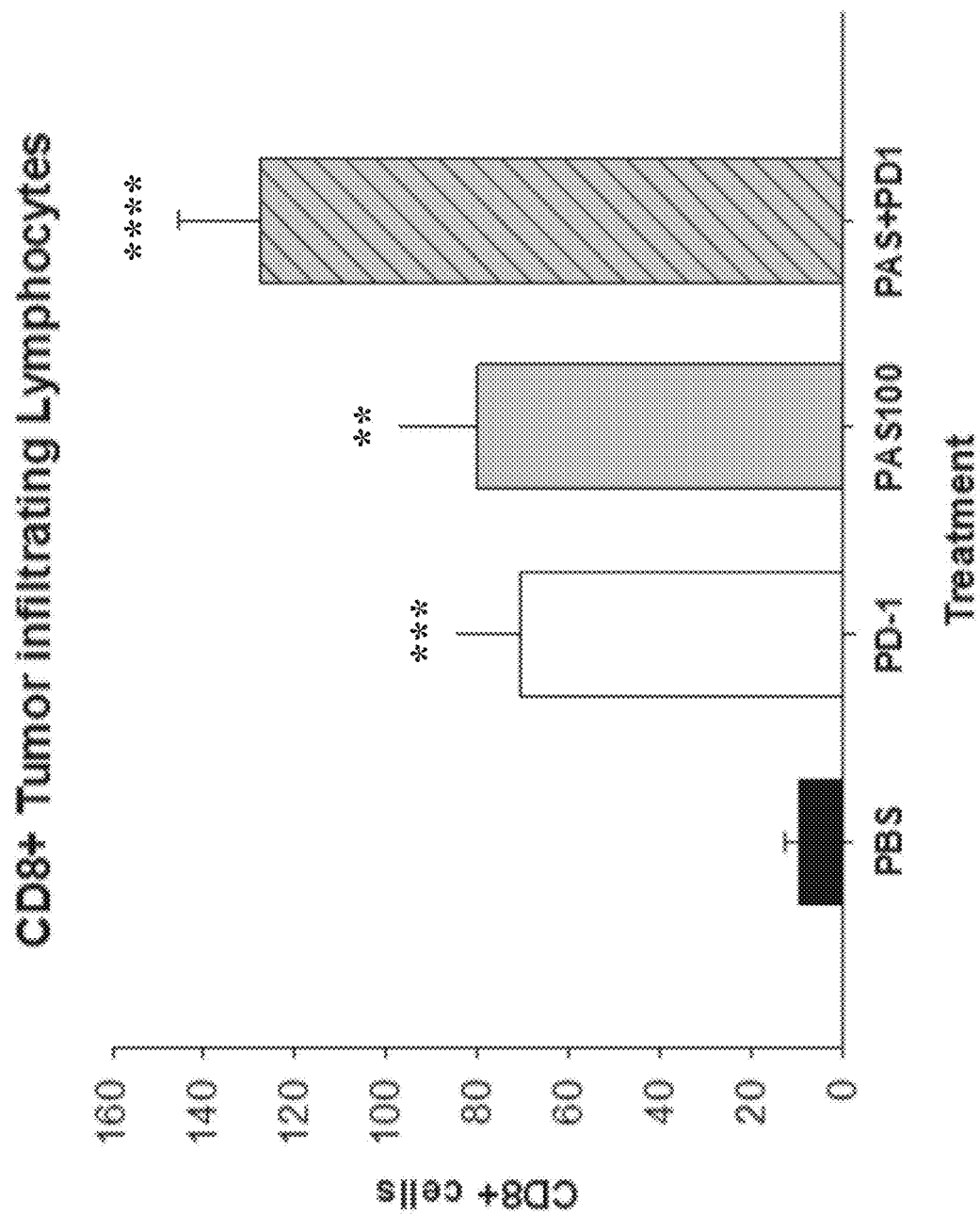

As shown in FIGS. 7A and 7B, CD8$^+$ tumor-infiltrating lymphocytes (TILs) increased with PAS100 and PD-1 alone, but were markedly increased with the combination therapy. The combination PAS100+PD-1 CD8$^+$ cells were significantly greater than PD-1 alone (p=0.042) and greater than PAS100 alone (p=0.039).

Example 7

Analysis of the Effect of PD-1 Monotherapy, PAS100 Monotherapy, and PD-1+PAS100 Combination Therapy on Foxp3$^+$ $T_{reg}$ Infiltration Tumors were fixed in 4% paraformaldehyde, paraffin embedded, and 8 μm sections were cut and mounted. Tumors were reacted with an anti-Foxp3 antibody (1:30;

EBIOSCIENCE™) and immunoreactive cells counted manually using ImageJ software. The results are presented in FIGS. 8A and 8B.

Figure 8A:
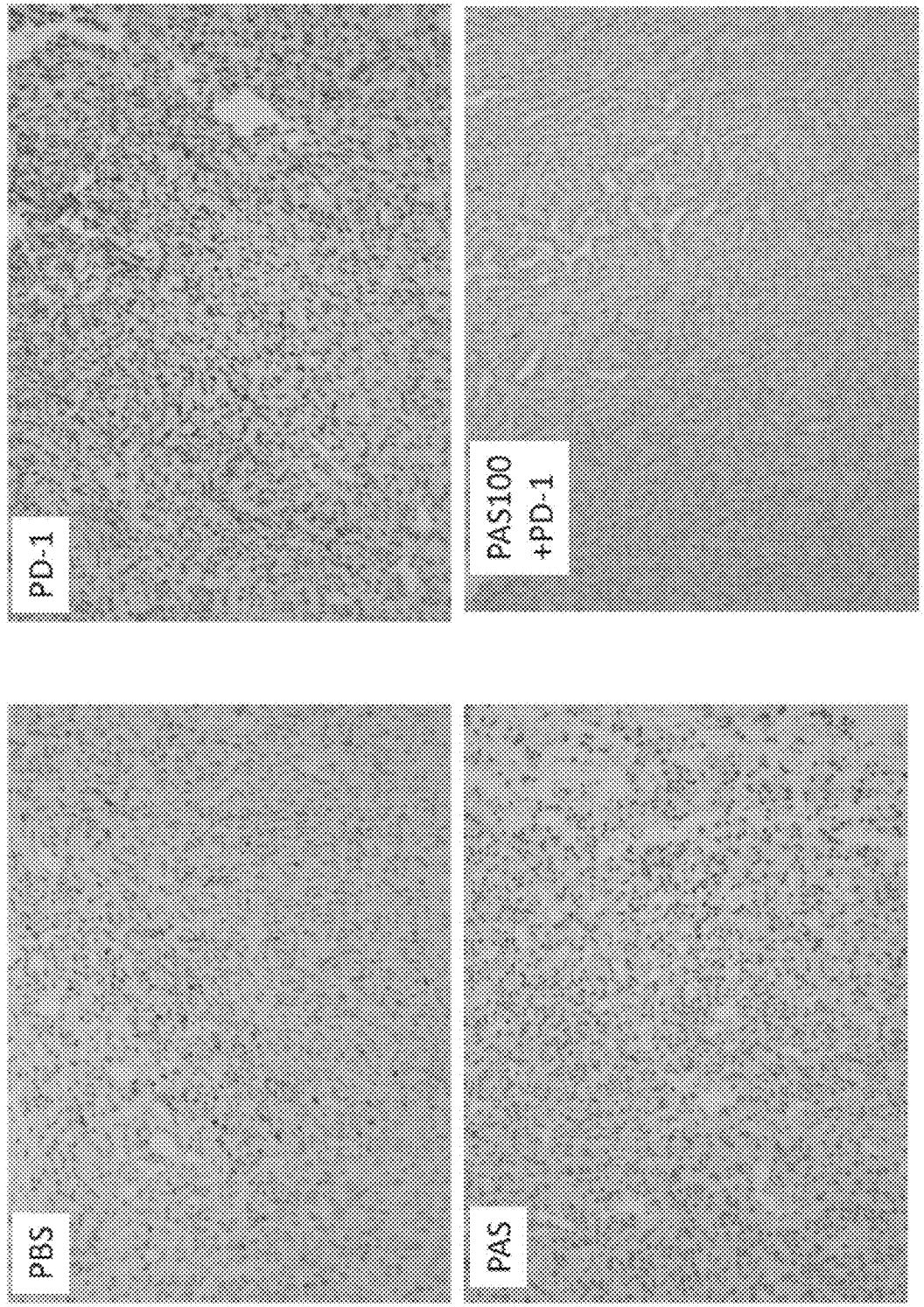
FIGS. 8A and 8B depict analyses of Foxp3+ cells in mT3 tumors.

FIG. 8A depicts exemplary mT3 tumors stained with an antibody that binds to the Foxp3 protein, a marker for $T_{regs}$. Comparison of the fields shows that as compared to PBS (upper left panel), PD-1 monotherapy (upper right panel), or PAS100 monotherapy (lower left panel), PAS100 & PD-1 combination therapy resulted in a decrease in the presence of intratumoral $T_{regs}$, suggesting that PAS100+PD-1 combination therapy might modify the intratumoral environment to an extent where the intratumoral microenvironment might be characterized by a lower degree of $T_{reg}$-based immunosuppression as compared to either monotherapy alone.

Figure 8B:
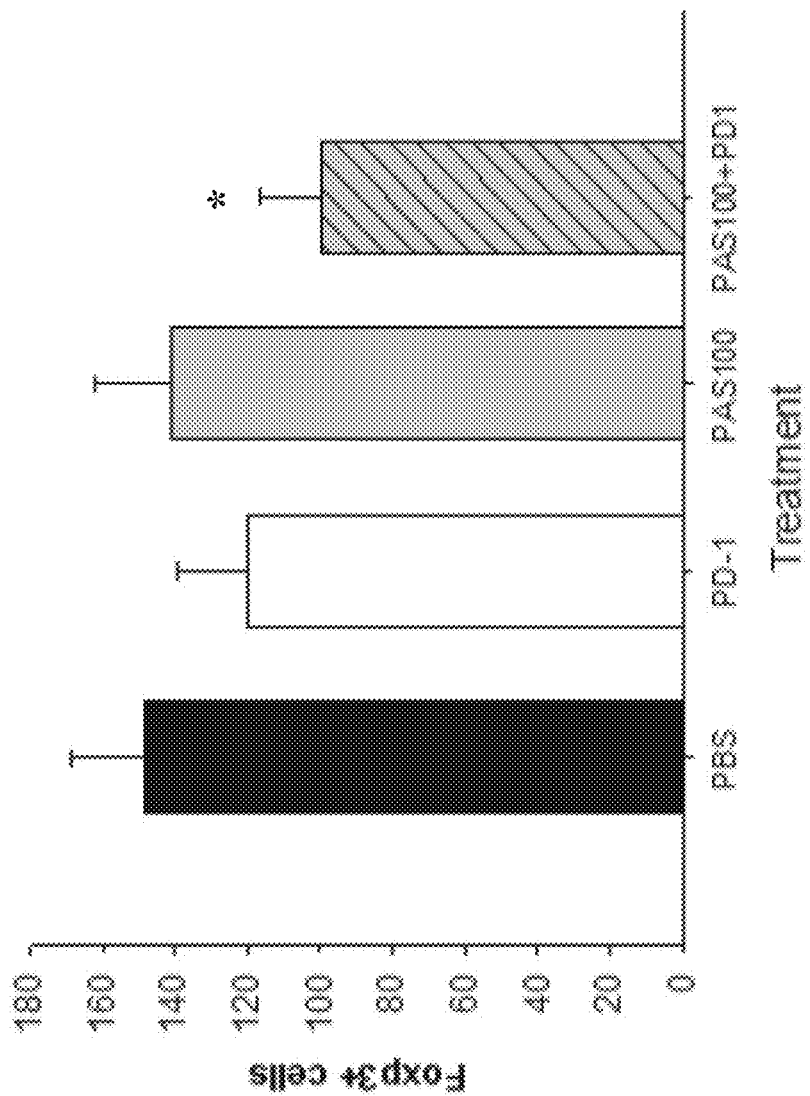

FIG. 8B is a bar graph summarizing the data exemplified by FIG. 8A. As compared to PBS, the number of Foxp3+ cells in tumors treated with PD-1 monotherapy or PAS100 monotherapy was not significantly different. Tumors treated with PAS100+PD-1 combination therapy had significantly fewer Foxp3+ cells that the negative control.

REFERENCES

All references listed in the instant disclosure, including but not limited to all patents, patent applications and publications thereof, scientific journal articles, and database entries (including but not limited to GENBANK® biosequence database entries and including all annotations available therein) are incorporated herein by reference in their entireties to the extent that they supplement, explain, provide a background for, and/or teach methodology, techniques, and/or compositions employed herein. The discussion of the references is intended merely to summarize the assertions made by their authors. No admission is made that any reference (or a portion of any reference) is relevant prior art. Applicants reserve the right to challenge the accuracy and pertinence of any cited reference.

Adams et al. (1993) Cancer Res 53:4026-4034.
Ajani et al. (2017) Nat Rev Dis Primers 3:17036.
Al-Attar et al. (2011) Biol Chem 392:277-289.
Alt et al. (1999) FEBS Lett 454:90-94.
Bass (2001) Nature 411:428-429.
Berkow et al. (1997) *The Merck Manual of Medical Information, Home ed.*, Merck Research Laboratories, Whitehouse Station, New Jersey, United States of America.
Berna & Jensen (2007) Curr Top Med Chem 7:1211-1231.
Berna et al. (2010) J Biol Chem 285:38905-38914.
Bernstein et al. (2001) Nature 409:363-366.
Bird et al. (1988) Science 242:423-426.
Boj et al. (2015) Cell 160:324-338.
Brahmer et al. (2012) N Engl J Med 366:2455-2465.
Brand & Fuller (1988) J Biol Chem 263:5341-5347.
Brett et al. (2002) J Clin Oncol 20:4225-4231.
Canadian Patent Application No. 2,359,180.
Carroll (2012) Mol Ther 20:1658-1660.
Clackson et al. (1991) Nature 352:624-628.
Coloma et al. (1997) Nature Biotechnol 15:159-163.
Duch et al. (1998) Toxicol Lett 100-101:255-263.
Ebadi (1998) *CRC Desk Reference of Clinical Pharmacology*. CRC Press, Boca Raton, Florida, United States of America.
Elbashir et al. (2001a) Nature 411:494-498.
Elbashir et al. (2001 b) Genes Dev 15:188-200.
Falconi et al. (2003) Dig Liver Dis 35:421-427.
Ferlay et al. (2013) Eur J Cancer 49:1374-1403.
Feig et al. (2012) Clin Cancer Res 18:4266-4276.
Fino et al. (2012) Am J Physiol Gastrointest Liver Physiol 302:G1244-G1252.
Fire (1999) Trends Genet 15:358-363.
Fire et al. (1998) Nature 391:806-811.
Freireich et al. (1966) Cancer Chemother Rep 50:219-244.
Gasiunas et al. (2012) Proc Nat Acad Sci USA 109: E2579-E2586.
GENBANK® biosequence database Accession Nos. NM_000805.4; NM_005018.2; NM_005214.4; NM_014143.3; NP_000796.1; NP_005009.2; NP_005205.2; NP_032824.1; NP_033973.2; NP_054862.1; NP_068693.1; NP_113862.1; NP_776722.1; NP_001003106.1; NP_001009236.1; NP_001076975.1; NP_001077358.1; NP_001100397.1; NP_001107830.1; NP_001138982.1; NP_001156884.1; NP_001178883.1; NP_001271065.1; NP_001278901.1; NP_001301026.1; XP_526000.1; XP_003776178.1; XP_004033133.1; XP_004033550.1; XP_005574073.1; XP_006939101.1; XP_009181095.2; XP_009454557.1; XP_015292694.1; XP_018889139.1.
Gerbino (2005) *Remington: The Science and Practice of Pharmacy*. 21st Edition. Lippincott Williams & Wilkins, Philadelphia, Pennsylvania, United States of America.
Gershoni et al. (2007) BioDrugs 21:145-156.
Gilliam et al. (2012) Pancreas 41:374-379.
Glockshuber et al. (1990) Biochemistry 29:1362-1367.
Goodman et al. (1996) *Goodman & Gilman's the Pharmacological Basis of Therapeutics*, 9th ed., McGraw-Hill Health Professions Division, New York, New York, United States of America.
Hale et al. (2012) Mol Cell 45:292-302.
Hammond et al. (2000) Nature 404:293-296.
Hanahan & Weinberg (2011) Cell 144:646-674.
Hidalgo (2010) N Engl J Med 362:1605-1617.
Holliger et al. (1993) Proc Natl Acad Sci USA 90:6444-6448.
Hruban et al. Int J Clin Exp Pathol 2008; 1: 306-316.
Hu et al. (1996) Cancer Res 56:3055-3061.
Huston et al. (1988) Proc Natl Acad Sci USA 85:5879-5883.
Huston et al. (1993) Int Rev Immunol 10:195-217.
Jinek et al. (2012) Science 337:816-821.
Katzung (2001) *Basic & Clinical Pharmacology*, 8th ed., Lange Medical Books/McGraw-Hill Medical Pub. Division, New York, New York, United States of America.
Kipriyanov et al. (1995) Cell Biophys 26:187-204.
Kipriyanov et al. (1998) Int J Cancer 77:763-772.
Kipriyanov et al. (1999) J Mol Biol 293:41-56.
Kohler et al. (1975) Nature 256:495.
Kontermann et al. (1999) J Immunol Meth 226:179-188.
Kortt et al. (1997) Protein Eng 10:423-433.
Kostelny et al. (1992), J Immunol 148:1547-1553.
Kurucz et al. (1995) J Immunol 154:4576-4582.
Le Cong et al. (2013) Science 339:819-823.
Le Gall et al. (1999) FEBS Lett 453:164-168.
Leach et al. (1996) Science 271:1734-1736.
Li et al. (2014) Vaccines 2:515-536.
Lutz et al. (2014) Oncoimmunology. 11:e962401.
Makarova et al. (2011) Nat Rev Microbiol 9:467-477.
Marks et al. (1991) J Mol Biol 222:581-597.
Matters et al. (2009) Pancreas 38:e151-e161.

McCartney et al. (1995) Protein Eng 8:301-314.
McWilliams et al. (1998) Gut 42:795-798.
Muller et al. (1998) FEBS Lett 432:45-49.
Neesse (2013) Onco Targets Ther 7:33-43.
Neesse et al. (2011) Gut 60:861-868.
Nykanen et al. (2001) Cell 107:309-321.
Nywening et al. (2016) Lancet Oncol 17:651-662.
Pack et al. (1992) Biochemistry 31:1579-1584.
Pardoll (2012) Nat Rev Cancer 12:252-264.
Paul (1993) *Fundamental Immunology*, Raven Press, New York, New York, United States of America.
PCT International Patent Application Publication Nos. WO 1992/22653; WO 1993/25521; WO 1999/07409; WO 1999/32619; WO 2000/01846; WO 2000/44895; WO 2000/44914; WO 2000/44914; WO 2000/63364; WO 2001/04313; WO 2001/29058; WO 2001/36646; WO 2001/36646; WO 2001/68836; WO 2001/75164; WO 2001/92513; WO 2002/055692; WO 2002/055693; WO 2002/044321; WO 2003/006477.
Pearson & Lipman (1988) Proc Natl Acad Sci USA 85:2444-2448.
Quante et al. (2013) Gastroenterology 145:63-78.
Rai et al. (2012) Surg Oncol 21:281-292.
Rehfeld et al. (1989) Cancer Res 49:2840-2843.
Remington et al. (1975) *Remington's Pharmaceutical Sciences*, 15th ed., Mack Pub. Co., Easton, Pennsylvania, United States of America.
Royal et al. (2010) J Immunother 33:828-33.
Ryan et al. (2014) N Engl J Med 371:1039-1049.
Saillan-Barreau et al. (1999) Diabetes 48:2015-2021.
Schally & Nagy (2004) Trends Endocrinol Metab 15:300-310.
Segal et al. (2014) J Clin Oncol 32(5 s):abstr 3002.
Seung Woo Cho et al. (2013a) Nat Biotechnol 31:1-10.
Seung Woo Cho et al. (2013b) Nat Biotechnol 31:230-232.
Shalaby et al. (1992) J Exp Med 175:217-225.
Siegel et al. (2014) CA Cancer J Clin 64:9-29.
Siegel et al. (2016) 66(1):7-30.
Singh et al. (1986) Cancer Res 46:1612-1616.
Singh et al. (1995) J Biol Chem 270:8429-8438.
Smith & Solomon (1988) Gastroenterology 95:1541-1548.
Smith & Solomon (2014) Am J Physiol Gastrointest Liver Physiol 306:G91-G101.
Smith et al. (1990) Dig Dis Sci 35:1377-1384.
Smith et al. (1991) Regul Pept 32:341-349.
Smith et al. (1994) Am J Physiol 266:R277-R283.
Smith et al. (1995) Am J Physiol 268:R135-R141.
Smith et al. (1996a) Am J Physiol 270:R1078-R1084.
Smith et al. (1996b) Am J Physiol 271:R797-R805.
Smith et al. (1998a) Int J Oncol 12:411-419.
Smith et al. (1998b) Intl J Mol Med 2:309-315.
Smith et al. (2004) Regul Pept 117:167-173.
Smith et al. (2014) Pancreas 43:1050-1059.
Smith et al. (2017) Cell Mol Gastroenterol Hepatol 4:75-83.
Smith et al. (2018) Cancer Immunol Immunother 67:195-207.
Soares et al. (2015) J Immunother 1:1-11.
Speight & Holford (eds.) (1997) *Avery's Drug Treatment: A Guide to the Properties, Choice, Therapeutic Use and Economic Value of Drugs in Disease Management*, 4th ed., Adis International, Philadelphia, Pennsylvania, United States of America.
Templeton & Brentnall (2013) Surg Clin North Am 93:629-645.
U.S. Patent Application Publication No. 2006/0188558.
U.S. Pat. Nos. 3,598,122; 4,816,567; 5,016,652; 5,234,933; 5,326,902; 5,935,975; 6,106,856; 6,162,459; 6,172,197; 6,172,197; 6,180,082; 6,248,516; 6,248,516; 6,291,158; 6,291,158; 6,495,605; 6,582,724; 8,945,839.
Upp et al. (1989) Cancer Res 49:488-492.
Vonderheide & Bayne (2013) Curr Opin Immunol 25:200-205.
Wagner et al. (2010) Cochrane Database Syst Rev 3:CD004064.
Watson et al. (1989) Br J Cancer 59:554-558.
Watson et al. (1995) Int J Cancer 61:233-240.
Watson et al. (1996) Cancer Res 56:880-885.
Watson et al. (1998) Int J Cancer 75:873-877.
Watson et al. (1999) Int J Cancer 81:248-254.
Watson et al. (2006) Nature Reviews Cancer 6:936-946.
Weiner & Lotze (2012) N Engl J Med 366:1156-1158.
Whitlow et al. (1991) Methods Companion Methods Enzymol 2:97-105.
Wianny & Zernicka-Goetz (1999) Nature Cell Biol 2:70-75.
Zhang et al. (2007) Cancer Biol Ther 6:218-227.
Zhang et al. (2014) Int Immunopharmacol 20:307-315.
Zhang et al. (2018) Cancers (Basel) 10(2):39.
Zheng et al. (2013) Gastroenterology 144:1230-1240.
Zhu et al. (1997) Protein Sci 6:781-788.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for preventing, reducing, and/or eliminating formation of fibrosis associated with a pancreatic tumor and/or a cancer, the method comprising contacting the pancreatic tumor and/or the cancer with a first composition comprising a gastrin peptide conjugated to an immunogenic carrier via a linker and a second composition comprising an immune checkpoint inhibitor, wherein the gastrin peptide comprises an amino acid sequence selected from the group consisting of EGPWLEEEEE (SEQ ID NO: 1), EGPWLEEEE (SEQ ID NO: 2), EGPWLEEEEEAY (SEQ ID NO: 3), and EGPWLEEEEEAYGWMDF (SEQ ID NO: 4) and the checkpoint inhibitor inhibits a biological activity of a target polypeptide selected from the group consisting of cytotoxic T-lymphocyte antigen 4 (CTLA4), programmed cell death-1 receptor (PD-1), and programmed cell death 1 receptor ligand (PD-L1).

2. The method of claim 1, wherein the immunogenic carrier is selected from the group consisting of diphtheria toxoid, tetanus toxoid, keyhole limpet hemocyanin, and bovine serum albumin.

3. The method of claim 1, wherein the linker comprises a ε-maleimido caproic acid N-hydroxysuccinamide ester.

4. The method of claim 3, wherein the linker and the gastrin peptide are separated by an amino acid spacer, optionally wherein the amino acid spacer is between 1 and 10 amino acids in length, further optionally wherein the amino acid spacer is 7 amino acids in length.

5. The method of claim 1, wherein the first composition further comprises an adjuvant, optionally an oil-based adjuvant.

6. The method of claim 1, wherein the immune checkpoint inhibitor is selected from the group consisting of Ipilimumab, Tremelimumab, Nivolumab, Pidilizumab, Pembrolizumab, AMP514, AUNP12, BMS-936559/MDX-1105, Atezolizumab, MPDL3280A, RG7446, RO5541267, MEDI4736, and Avelumab.

7. A method for increasing the number of TEMRA cells and/or CD8+ tumor infiltrating lymphocytes (TILs) in a subject, wherein the TEMRA cells and/or the CD8+ TILs respond to a gastrin-associated pancreatic tumor and/or cancer in the subject, the method comprising administering to a subject in need thereof an effective amount of a first composition comprising a gastrin peptide conjugated to an immunogenic carrier via a linker and a second composition comprising an immune checkpoint inhibitor, wherein the gastrin peptide comprises an amino acid sequence selected from the group consisting of EGPWLEEEEE (SEQ ID NO: 1), EGPWLEEEE (SEQ ID NO: 2), EGPWLEEEEEAY (SEQ ID NO: 3), and EGPWLEEEEEAYGWMDF (SEQ ID NO: 4) and the checkpoint inhibitor inhibits a biological activity of a target polypeptide selected from the group consisting of cytotoxic T-lymphocyte antigen 4 (CTLA4), programmed cell death-1 receptor (PD-1), and programmed cell death 1 receptor ligand (PD-L1), and further wherein the number of TEMRA cells and/or the number of CD8+ TILs that respond to the gastrin-associated pancreatic tumor and/or cancer is increased in the subject.

8. The method of claim 7, wherein the administering results in improves survival of the subject, reduced tumor growth, and/or enhanced efficacy of a chemotherapeutic agent and/or an immune checkpoint therapy in the subject as compared to that which would have occurred had the pharmaceutical composition not been administered.

9. A method for preventing, reducing, and/or eliminating metastasis of a gastrin-associated pancreatic tumor or cancer in a subject, the method comprising administering to a subject having a gastrin-associated tumor or cancer an effective amount of a first composition comprising a gastrin peptide conjugated to an immunogenic carrier via a linker and a second composition comprising an immune checkpoint inhibitor, wherein the gastrin peptide comprises an amino acid sequence selected from the group consisting of EGPWLEEEEE (SEQ ID NO: 1), EGPWLEEEE (SEQ ID NO: 2), EGPWLEEEEEAY (SEQ ID NO: 3), and EGPWLEEEEEAYGWMDF (SEQ ID NO: 4) and the checkpoint inhibitor inhibits a biological activity of a target polypeptide selected from the group consisting of cytotoxic T-lymphocyte antigen 4 (CTLA4), programmed cell death-1 receptor (PD-1), and programmed cell death 1 receptor ligand (PD-L1), and further wherein the effective amount is sufficient to reduce the number of FoxP3+ inhibitory T-regulatory cells in the subject.

* * * * *